(12) United States Patent
Nakai et al.

(10) Patent No.: US 9,487,508 B2
(45) Date of Patent: Nov. 8, 2016

(54) SGC STIMULATORS

(71) Applicants: Takashi Nakai, Newton, MA (US); Nicholas Robert Perl, Brookline, MA (US); Joel Moore, Lexington, MA (US)

(72) Inventors: Takashi Nakai, Newton, MA (US); Nicholas Robert Perl, Brookline, MA (US); Joel Moore, Lexington, MA (US)

(73) Assignee: IRONWOOD PHARMACEUTICALS, INC., Cambridge, MA (US)

( * ) Notice: Subject to any disclaimer, the term of this patent is extended or adjusted under 35 U.S.C. 154(b) by 0 days.

(21) Appl. No.: 14/429,028

(22) PCT Filed: Sep. 19, 2013

(86) PCT No.: PCT/US2013/060680
§ 371 (c)(1),
(2) Date: Mar. 18, 2015

(87) PCT Pub. No.: WO2014/047325
PCT Pub. Date: Mar. 27, 2014

(65) Prior Publication Data
US 2015/0232461 A1  Aug. 20, 2015

Related U.S. Application Data

(60) Provisional application No. 61/703,114, filed on Sep. 19, 2012.

(51) Int. Cl.
| | |
|---|---|
| *C07D 403/04* | (2006.01) |
| *C07D 413/14* | (2006.01) |
| *C07D 487/04* | (2006.01) |
| *A61K 31/4155* | (2006.01) |
| *A61K 31/513* | (2006.01) |
| *A61K 31/506* | (2006.01) |
| *A61K 31/5377* | (2006.01) |
| *A61K 31/519* | (2006.01) |

(52) U.S. Cl.
CPC ......... *C07D 413/14* (2013.01); *A61K 31/4155* (2013.01); *A61K 31/506* (2013.01); *A61K 31/513* (2013.01); *A61K 31/519* (2013.01); *A61K 31/5377* (2013.01); *C07D 403/04* (2013.01); *C07D 487/04* (2013.01)

(58) Field of Classification Search
CPC   C07D 403/04; C07D 413/14; C07D 487/04; A61K 31/4155
USPC ........................ 544/122, 280, 320, 324, 331; 514/235.8, 265.1, 272, 275
See application file for complete search history.

(56) References Cited

U.S. PATENT DOCUMENTS

| | | | | |
|---|---|---|---|---|
| 5,510,320 | A | * | 4/1996 | Tseng ..................... A01N 47/38 504/273 |
| 8,748,442 | B2 | | 6/2014 | Kim et al. |
| 9,061,030 | B2 | | 6/2015 | Kim et al. |
| 9,139,564 | B2 | | 9/2015 | Kim et al. |
| 9,309,235 | B2 | | 4/2016 | Im et al. |

(Continued)

FOREIGN PATENT DOCUMENTS

| | | |
|---|---|---|
| EP | 2006288 A1 | 12/2008 |
| WO | 9307138 A1 | 4/1993 |

(Continued)

OTHER PUBLICATIONS

Ivashchenko et al., CAPLUS Abstract No. 90:179375 (1979).*
Ivashchenko et al., CAPLUS Abstract No. 94:139737 (1981).*
Ivashchenko et al., CAPLUS Abstract No. 94:139736 (1981).*

(Continued)

*Primary Examiner* — Deepak Rao
(74) *Attorney, Agent, or Firm* — Heslin, Rothenberg, Farley & Mesiti, P.C.

(57) ABSTRACT

The present patent application discloses at least the compounds according to Formula I or Formula Ib shown below, or pharmaceutically acceptable salts thereof,

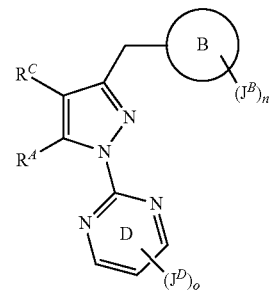

Formula I

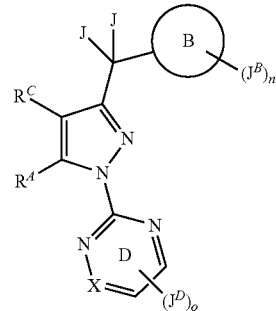

Formula Ib wherein ring B, $J^B$, n, $J^D$, J, o, X, $R^C$ and $R^A$ are as described herein.

24 Claims, No Drawings

(56) References Cited

U.S. PATENT DOCUMENTS

| | | | |
|---|---|---|---|
| 2006/0148858 A1* | 7/2006 | Maekawa | C07D 231/12 |
| | | | 514/341 |
| 2009/0042917 A1* | 2/2009 | Bessho | A01N 43/56 |
| | | | 514/273 |
| 2010/0144864 A1 | 6/2010 | Currie et al. | |
| 2010/0292236 A1* | 11/2010 | Li | C07D 231/14 |
| | | | 514/236.5 |
| 2012/0184516 A1 | 7/2012 | Kim et al. | |
| 2013/0178475 A1 | 7/2013 | Moore et al. | |
| 2015/0250795 A1 | 9/2015 | Kim et al. | |
| 2015/0342954 A1 | 12/2015 | Kim et al. | |
| 2016/0031903 A1 | 2/2016 | Nakai et al. | |

FOREIGN PATENT DOCUMENTS

| | | |
|---|---|---|
| WO | 9715570 A1 | 5/1997 |
| WO | 0027394 A1 | 5/2000 |
| WO | 2011119518 A1 | 9/2011 |
| WO | 2011147810 A1 | 12/2011 |
| WO | 2012064559 A1 | 5/2012 |
| WO | 2013101830 | 7/2013 |
| WO | 2014047111 | 3/2014 |
| WO | 2014047325 | 3/2014 |
| WO | 2015089182 | 6/2015 |
| WO | 2015106268 | 7/2015 |

OTHER PUBLICATIONS

Ghofrani et al., Soluble guanylate cyclase stimulation: an emerging option in pulmonary hypertension therapy, European Respiratory Review, vol. 18, No. 111, pp. 35-41, 2009.*

International Search Report for PCT/US2013/060680 dated Feb. 20, 2014.

Ivaschenko, A.V. et al; "Synthesis and study of 2-(1-pyrazolyl)purine derivatives," Khimiya Geterotsiklicheskikh Soedinenii (10), pp. 1404-1406, 1977.

Ivaschenko, A.V. et al; "Synthesis and study of derivatives of 2-(1-pyrazolyl)pyrirnadine," Khimiya Geterotsiklicheskikh Soedinenii (9), pp. 1255-1257, 1977.

David L. Selwood et al., "Synthesis and Biological Evaluation of Novel Pyrazoles and Indazoles as Activators of the Nitric Oxide Receptor, Soluble Guanylate Cyclase" Journal of Medical Chemistry, vol. 44, No. 1, pp. 78-93, Jan. 4, 2001.

Im et al., U.S. Appl. No. 15/054,448, filed Feb. 26, 2016.

* cited by examiner

SGC STIMULATORS

CROSS REFERENCE TO RELATED APPLICATIONS

This application is a 371 filing of PCT/US2013/060680, filed Sep. 19, 2013, which claims the priority of U.S. Provisional Application No. 61/703,114, filed Sep. 19, 2012, the disclosures of which applications are herein incorporated by reference.

FIELD OF THE INVENTION

The present disclosure relates to stimulators of soluble guanylate cyclase (sGC), pharmaceutical formulations comprising thereof and their uses, alone or in combination with one or more additional agents, for treating and/or preventing various diseases, wherein an increase in the concentration of nitric oxide (NO) or an increase in the concentration of cyclic Guanosine Monophosphate (cGMP) might be desirable.

BACKGROUND OF THE INVENTION

Soluble guanylate cyclase (sGC) is the primary receptor for nitric oxide (NO) in vivo. sGC can be activated via both NO-dependent and NO-independent mechanisms. In response to this activation, sGC converts GTP into the secondary messenger cyclic GMP (cGMP). The increased level of cGMP, in turn, modulates the activity of downstream effectors including protein kinases, phosphodiesterases (PDEs) and ion channels.

In the body, NO is synthesized from arginine and oxygen by various nitric oxide synthase (NOS) enzymes and by sequential reduction of inorganic nitrate. Three distinct isoforms of NOS have been identified: inducible NOS (iNOS or NOS II) found in activated macrophage cells; constitutive neuronal NOS (nNOS or NOS I), involved in neurotransmission and long term potentiation; and constitutive endothelial NOS (eNOS or NOS III) which regulates smooth muscle relaxation and blood pressure.

Experimental and clinical evidence indicates that reduced bioavailability and/or responsiveness to endogenously produced NO contributes to the development of cardiovascular, endothelial, renal and hepatic disease, as well as erectile dysfunction and other sexual disorders (e.g. female sexual disorder or vaginal atrophy), wound healing. In particular, the NO signaling pathway is altered in cardiovascular diseases, including, for instance, systemic and pulmonary hypertension, portal hypertension, heart failure, angina, stroke, thrombosis, obstructive thromboanginitis and other thromboembolic diseases, peripheral vascular disease, peripheral arterial disease, fibrosis of the liver, lung or kidney and atherosclerosis.

sGC stimulators are also useful in the treatment of lipid related disorders such as e.g., dyslipidemia, hypercholesterolemia, hypertriglyceridemia, sitosterolemia, fatty liver disease, and hepatitis.

Pulmonary hypertension (PH) is a disease characterized by sustained elevation of blood pressure in the pulmonary vasculature (pulmonary artery, pulmonary vein and pulmonary capillaries), which results in right heart hypertrophy, eventually leading to right heart failure and death. In PH, the bioactivity of NO and other vasodilators such as prostacyclin is reduced, whereas the production of endogenous vasoconstrictors such as endothelin is increased, resulting in excessive pulmonary vasoconstriction. sGC stimulators have been used to treat PH because they promote smooth muscle relaxation, which leads to vasodilation.

Treatment with NO-independent sGC stimulators also promoted smooth muscle relaxation in the corpus cavernosum of healthy rabbits, rats and humans, causing penile erection, indicating that sGC stimulators are useful for treating erectile dysfunction.

NO-independent, heme-dependent, sGC stimulators, such as those disclosed herein, have several important differentiating characteristics, including crucial dependency on the presence of the reduced prosthetic heme moiety for their activity, strong synergistic enzyme activation when combined with NO and stimulation of the synthesis of cGMP by direct stimulation of sGC, independent of NO. The benzylindazole compound YC-1 was the first sGC stimulator to be identified. Additional sGC stimulators with improved potency and specificity for sGC have since been developed. These compounds have been shown to produce anti-aggregatory, anti-proliferative and vasodilatory effects.

Since compounds that stimulate sGC in an NO-independent manner offer considerable advantages over other current alternative therapies, there is a need to develop novel stimulators of sGC. They are potentially useful in the prevention, management and treatment of disorders such as pulmonary hypertension, arterial hypertension, portal hypertension, heart failure, atherosclerosis, inflammation, thrombosis, thrombogenic disorders, obstructive thromboanginitis, renal fibrosis and failure, liver cirrhosis, lung fibrosis, erectile dysfunction, female sexual arousal disorder and vaginal atrophy, wound healing and other cardiovascular disorders; they are also potentially useful for the prevention, management and treatment of lipid related disorders. Compounds that stimulate sGC in an NO-independent manner are also useful for the treatment of shock and related complications.

SUMMARY OF THE INVENTION

A compound according to Formula Ib, or a pharmaceutically acceptable salt thereof,

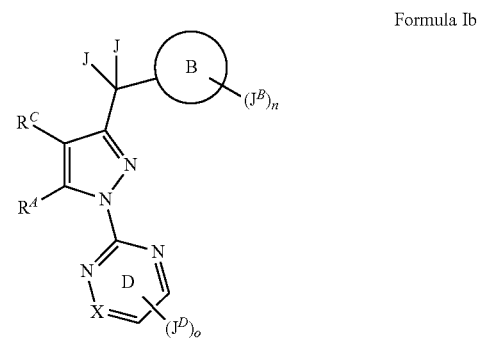

Formula Ib wherein X is either carbon or nitrogen;
wherein either
i) ring B is absent with $J^B$ connected directly to the carbon atom bearing two J groups, each J is independently selected from hydrogen, methyl or fluorine, n is 1 and $J^B$ is a $C_{1-6}$ alkyl chain optionally substituted by up to 6 instances of fluorine; or
ii) ring B is a phenyl or a 5 or 6-membered heteroaryl ring, containing 1 or 2 ring heteroatoms selected from N, O or S; wherein with ring B being the phenyl or 5 or 6-membered heteroaryl ring; each J is hydrogen; n is an integer selected from 0 to 3; and each $J^B$ is independently selected from halogen, —CN, a $C_{1-6}$ aliphatic, —$OR^B$ or a $C_{3-8}$ cycloaliphatic group; wherein each said $C_{1-6}$ aliphatic and each said $C_{3-8}$ cycloaliphatic group is optionally and independently substituted with up to 3 instances of $R^3$; each $R^B$ is independently selected from hydrogen, a $C_{1-6}$ aliphatic or a $C_{3-8}$ cycloaliphatic; wherein each said $C_{1-6}$ aliphatic and each said $C_{3-8}$ cycloaliphatic ring is optionally and independently substituted with up to 3 instances of $R^{3a}$;

each $R^3$ is independently selected from halogen, —CN, $C_{1-4}$ alkyl, $C_{1-4}$ haloalkyl, —$O(C_{1-4}$ alkyl) or —$O(C_{1-4}$ haloalkyl);

each $R^{3a}$ is independently selected from halogen, —CN, $C_{1-4}$ alkyl, $C_{1-4}$ haloalkyl, —$O(C_{1-4}$ alkyl) or —$O(C_{1-4}$ haloalkyl);

o is an integer selected from 0 to 3;

each $J^D$ is independently selected from halogen, —CN, —$OR^D$, —$SR^D$, —$C(O)R^D$, —$C(O)OR^D$, —$OC(O)R^D$, —$C(O)N(R^D)_2$, —$N(R^D)_2$, —$N(R^d)C(O)R^D$, —$N(R^d)C(O)OR^D$, —$N(R^d)C(O)N(R^D)_2$, —$OC(O)N(R^D)_2$, —$SO_2R^D$, —$SO_2N(R^D)_2$, —$N(R^d)SO_2R^D$, a $C_{1-6}$ aliphatic, —$(C_{1-6}$ aliphatic)-$R^f$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocyclic ring and each said 5 to 10-membered heteroaryl ring contains between 1 and 3 heteroatoms independently selected from O, N or S; and wherein each said $C_{1-6}$ aliphatic, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 3 instances of $R^5$;

each $R^D$ is independently selected from hydrogen, a $C_{1-6}$ aliphatic, —$(C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocylic ring and each said 5 to 6-membered heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted with up to 3 instances of Rya;

each $R^d$ is independently selected from hydrogen, a $C_{1-6}$ aliphatic, —$(C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said heterocyclic ring and each said heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^{5b}$;

each $R^f$ is independently selected from a $C_{3-8}$ cycloaliphatic ring, a 4 to 8-membered heterocyclic ring, phenyl or a 5 to 6-membered heteroaryl ring; wherein each said heterocyclic ring and each said heteroaryl ring contains between 1 and 3 heteroatoms independently selected from O, N or S; and wherein each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^{5c}$;

when $J^D$ is —$C(O)N(R^D)_2$, —$N(R^D)_2$, —$OC(O)N(R^D)_2$ or —$SO_2N(R^D)_2$, the two $R^D$ groups together with the nitrogen atom attached to the two $R^D$ groups may form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S; and wherein each said 4 to 8-membered heterocyclic ring and each said 5-membered heteroaryl ring is optionally and independently substituted by up to 3 instances of $R^{5d}$;

when $J^D$ is $N(R^d)C(O)R^D$ the $R^D$ group together with the carbon atom attached to the $R^D$ group, with the nitrogen atom attached to the $R^d$ group, and with the $R^d$ group may form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^{5d}$;

when $J^D$ is $N(R^d)C(O)OR^D$ or $N(R^d)C(O)N(R^D)_2$, the $R^D$ group together with the oxygen atom attached to the $R^D$ group, with the carbon atom of the —C(O)— portion of the —$N(R^d)C(O)OR^D$ group, with the nitrogen atom attached to the $R^d$ group, or, alternatively one of the $R^D$ groups attached to the nitrogen atom, together with said nitrogen atom, and with the N atom attached to the $R^d$ group and said $R^d$ group may form a 4 to 8-membered heterocyclic ring; wherein said 4 to 8-membered heterocyclic ring optionally contains up to 2 additional heteroatoms independently selected from N, O or S, and is optionally and independently substituted by up to 3 instances of $R^{5d}$;

when $J^D$ is —$N(R^d)SO_2R^D$, the $R^D$ group together with the sulfur atom attached to the $R^D$ group, with the nitrogen atom attached to the $R^d$ group, and with the $R^d$ group may combine to form a 4 to 8-membered heterocyclic ring; wherein said 4 to 8-membered heterocyclic ring optionally contains up to 2 additional heteroatoms independently selected from N, O or S, and is optionally and independently substituted by up to 3 instances of $R^{5d}$;

each $R^5$ is independently selected from halogen, —CN, $C_{1-4}$ alkyl, —$(C_{1-4}$ alkyl)-$R^6$, a $C_{7-12}$ aralkyl, $C_{3-8}$ cycloalkyl ring, $C_{1-4}$ cyanoalkyl, —$OR^6$, —$SR^6$, —$OCOR^6$, —$COR^E$, —$C(O)OR^6$, —$C(O)N(R^6)_2$, —$N(R^6)C(O)R^6$, —$N(R^6)_2$, —$SO_2R^6$, —$SO_2N(R^6)_2$, —$N(R^6)SO_2R^6$, phenyl or an oxo group; wherein each said phenyl group is optionally and independently substituted with up to 3 instances of halogen, —OH, —$NH_2$, —$NH(C_{1-4}$ alkyl), —$N(C_{1-4}$ alkyl)$_2$, —$NO_2$, —CN, $C_{1-4}$ alkyl, $C_{1-4}$ haloalkyl, —$O(C_{1-4}$ alkyl) or —$O(C_{1-4}$ haloalkyl); and wherein each said $C_{7-12}$ aralkyl, each said $C_{1-4}$ alkyl chain and each said $C_{3-8}$ cycloalkyl group is optionally and independently substituted with up to 3 instances of halogen;

each $R^{5b}$ is independently selected from halogen, —CN, $C_{1-4}$ alkyl, —$(C_{1-4}$ alkyl)-$R^6$, a $C_{7-12}$ aralkyl, $C_{3-8}$ cycloalkyl ring, $C_{1-4}$ cyanoalkyl, —$OR^6$, —$SR^6$, —$OCOR^6$, —$COR^E$, —$C(O)OR^6$, —$C(O)N(R^6)_2$, —$N(R^6)C(O)R^6$, —$N(R^6)_2$, —$SO_2R^6$, —$SO_2N(R^6)_2$, —$N(R^6)SO_2R^6$, phenyl or an oxo group; wherein each said phenyl group is optionally and independently substituted with up to 3 instances of halogen, —OH, —$NH_2$, —$NH(C_{1-4}$ alkyl), —$N(C_{1-4}$ alkyl)$_2$, —$NO_2$, —CN, $C_{1-4}$ alkyl, $C_{1-4}$ haloalkyl, —$O(C_{1-4}$ alkyl) or —$O(C_{1-4}$ haloalkyl); and wherein each said $C_{7-12}$ aralkyl, each said $C_{1-4}$ alkyl chain and each said $C_{3-8}$ cycloalkyl group is optionally and independently substituted with up to 3 instances of halogen;

each $R^{5b}$ is independently selected from halogen, —CN, $C_{1-4}$ alkyl, —$(C_{1-4}$ alkyl)-$R^6$, a $C_{7-12}$ aralkyl, $C_{3-8}$ cycloalkyl ring, $C_{1-4}$ cyanoalkyl, —$OR^6$, —$SR^6$, —$OCOR^6$, —$COR^E$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl, each said C$_{1-4}$ alkyl chain and each said C$_{3-8}$ cycloalkyl group is optionally and independently substituted with up to 3 instances of halogen;

each R$^{5c}$ is independently selected from halogen, —CN, C$_{1-4}$ alkyl, —(C$_{1-4}$ alkyl)-R$^6$, a C$_{7-12}$ aralkyl, C$_{3-8}$ cycloalkyl ring, C$_{1-4}$ cyanoalkyl, —OR$^6$, —SR$^6$, —OCOR$^6$, —COR$^E$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl, each said C$_{1-4}$ alkyl chain and each said C$_{3-8}$ cycloalkyl group is optionally and independently substituted with up to 3 instances of halogen;

each R$^{5d}$ is independently selected from halogen, —CN, C$_{1-4}$ alkyl, —(C$_{1-4}$ alkyl)-R$^6$, a C$_{7-12}$ aralkyl, C$_{3-8}$ cycloalkyl ring, C$_{1-4}$ cyanoalkyl, —OR$^6$, —SR$^6$, —OCOR$^6$, —COR$^E$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl, each said C$_{1-4}$ alkyl chain and each said C$_{3-8}$ cycloalkyl group is optionally and independently substituted with up to 3 instances of halogen;

each R$^6$ is independently selected from hydrogen, a C$_{1-4}$ alkyl, a C$_{2-4}$ alkenyl, phenyl, a C$_{7-12}$ aralkyl or a C$_{3-8}$ cycloalkyl ring; wherein each said C$_{1-4}$ alkyl, each said C$_{2-4}$ alkenyl, each said phenyl, each said C$_{7-12}$ aralkyl and each said cycloalkyl group is optionally and independently substituted with up to 3 instances of halogen;

alternatively, two instances of R$^6$ linked to the same nitrogen atom of R$^5$, R$^{5a}$, R$^{5b}$, R$^{5c}$ or R$^{5d}$, together with said nitrogen atom of R$^5$, R$^{5a}$, R$^{5b}$, R$^{5c}$ or R$^{5d}$, respectively, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; or alternatively, one instance of R$^6$ linked to a nitrogen atom of R$^5$, R$^{5a}$, R$^{5b}$, R$^{5c}$ or R$^{5d}$ and one instance of R$^6$ linked to a carbon or sulfur atom of the same R$^5$, R$^{5a}$, R$^{5b}$, R$^{5c}$ or R$^{5d}$, respectively, together with said nitrogen and said carbon or sulfur atom of the same R$^5$, R$^{5a}$, R$^{5b}$, R$^{5c}$ or R$^{5d}$, respectively, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

alternatively, two J$^D$ groups attached to two vicinal ring D atoms, taken together with said two vicinal ring D atoms, form a 5 to 7-membered heterocycle or a 5-membered heteroaryl ring that is fused to ring D; wherein said 5 to 7-membered heterocycle or said 5-membered ring heteroaryl contains from 1 to 3 heteroatoms independently selected from N, O or S; and wherein said 5 to 7-membered heterocycle or said 5-membered heteroaryl ring is optionally and independently substituted by up to 3 instances of oxo or —(Y)—R$^9$;

wherein Y is either absent or is a linkage in the form of a C$_{1-6}$ alkyl chain, optionally substituted by up to 6 instances of fluoro;

each R$^9$ is independently selected from hydrogen, —CN, —OR$^{10}$, —COR$^{10}$, —OC(O)R$^{10}$, —C(O)OR$^{10}$, —C(O)N(R$^{10}$)$_2$, —C(O)N(R$^{10}$)SO$_2$R$^{10}$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —N(R$^{10}$)SO$_2$R$^{10}$, a C$_{3-6}$ cycloalkyl ring, a 4-8-membered heterocyclic ring, a phenyl ring or a 5-6 membered heteroaroaryl ring; wherein each said 4 to 8-membered heterocyclic ring or 5 to 6-membered heteroaryl ring contains up to 4 ring heteroatoms independently selected from N, O or S; and wherein each of said C$_{3-6}$ cycloalkyl rings, each of said 4 to 8-membered heterocyclic rings, each of said phenyl and each of said 5 to 6-membered heteroaryl rings is optionally substituted with up to 3 instances of Rica;

wherein each R$^{10}$ is independently selected from hydrogen, a C$_{1-6}$ alkyl, phenyl, benzyl, a C$_{3-6}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said C$_{1-6}$ alkyl, each said phenyl, each said benzyl, each said C$_{3-8}$ cycloalkyl group, each said 4 to 7-membered heterocyclic ring and each 5 or 6-membered heteroaryl ring is optionally and independently substituted with up to 3 instances of R$^{11b}$;

each R$^{11a}$ is independently selected from halogen, C$_{1-6}$ alkyl, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ or —N(R$^{12}$)SO$_2$R$^{12}$; wherein each of said C$_{1-6}$ alkyl is optionally and independently substituted by up to 6 instances of fluoro and/or 3 instances of R$^{12}$;

each R$^{11b}$ is independently selected from halogen, C$_{1-6}$ alkyl, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ or —N(R$^{12}$)SO$_2$R$^{12}$; wherein each of said C$_{1-6}$ alkyl is optionally and independently substituted by up to 6 instances of fluoro and/or 3 instances of R$^{12}$;

each R$^{12}$ is selected from C$_{1-4}$ alkyl, C$_{1-4}$ (fluoroalkyl), —OH, —NH$_2$, —NH(C$_{1-4}$ alkyl), —N(C$_{1-4}$ alkyl)$_2$, —CN, —COOH, —COO(C$_{1-4}$ alkyl), —O(C$_{1-4}$ alkyl), —O(C$_{1-4}$ fluoroalkyl) or oxo;

R$^C$ is either
i) a ring C; or
ii) R$^C$ is selected from halogen, —CN, C$_{1-6}$ alkyl, —(C$_{1-6}$ alkyl)-R$^N$, —OR$^K$, —COR$^K$, —OC(O)R$^K$, —C(O)OR$^K$, —C(O)N(R$^K$)$_2$, —N(R$^k$)C(O)R$^K$, —N(R$^k$)C(O)OR$^K$, —N(R$^k$)C(O)N(R$^K$)$_2$, —N(R$^K$)$_2$, —SO$_2$R$^K$, —SO$_2$N(R$^K$)$_2$ or —N(R$^k$)SO$_2$R$^K$; wherein said R$^C$ that is a C$_{1-6}$ alkyl is optionally and independently substituted with up to 6 instances of fluoro and/or up to 3 instances of R$^{7c}$1;

each R$^k$ is independently selected from hydrogen or a C$_{1-6}$ alkyl;

each R$^K$ is independently selected from hydrogen, a C$_{1-6}$ alkyl, a phenyl ring, a monocyclic 5 or 6-membered heteroaryl ring, a monocyclic C$_{3-6}$ cycloaliphatic ring, or a monocyclic 4 to 6-membered heterocycle; wherein said monocyclic 5 or 6-membered heteroaryl ring or said monocyclic 4 to 6-membered heterocycle contain between 1 and 4 heteroatoms selected from N, O or S; wherein said monocyclic 5 or 6-membered heteroaryl ring is not a 1,3,5-triazinyl ring; and wherein said phenyl, said monocyclic 5 to 6-membered heteroaryl ring, said monocyclic $C_{3-6}$ cycloaliphatic ring, or said monocyclic 4 to 6-membered heterocycle is optionally and independently substituted with up to 6 instances of fluoro and/or up to 3 instances of $J^M$; and wherein each $R^K$ that is a $C_{1-6}$ alkyl is optionally and independently substituted by up to 3 instances of $R^{7d}$;

each $R^N$ is independently selected from a phenyl ring, a monocyclic 5 or 6-membered heteroaryl ring, a monocyclic $C_{3-6}$ cycloaliphatic ring, or a monocyclic 4 to 6-membered heterocycle; wherein said monocyclic 5 or 6-membered heteroaryl ring or said monocyclic 4 to 6-membered heterocycle contain between 1 and 4 heteroatoms selected from N, O or S; wherein said monocyclic 5 or 6-membered heteroaryl ring is not a 1,3,5-triazinyl ring; and wherein said phenyl, said monocyclic 5 to 6-membered heteroaryl ring, said monocyclic $C_{3-6}$ cycloaliphatic ring, or said monocyclic 4 to 6-membered heterocycle is optionally and independently substituted with up to 6 instances of fluoro and/or up to 3 instances of $J^M$;

each $J^M$ is independently selected from —CN, a $C_{1-6}$ aliphatic, —$OR^M$, —$SR^M$, —$N(R^M)_2$, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^{7c}$;

each $R^M$ is independently selected from hydrogen, a $C_{1-6}$ aliphatic, a $C_{3-8}$ cycloaliphatic ring or a 4 to 8-membered heterocyclic ring; wherein each said 4 to 8-membered heterocylic ring contains between 1 and 3 heteroatoms independently selected from O, N or S; and wherein each said $C_{1-6}$ aliphatic, each said $C_{3-8}$ cycloaliphatic ring and each said 4 to 8-membered heterocyclic ring, is optionally and independently substituted with up to 3 instances of $R^{7e}$;

ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6-membered heteroaryl ring is not a 1,3,5-triazinyl ring; and wherein said phenyl, monocyclic 5 to 6-membered heteroaryl ring, bicyclic 8 to 10-membered heteroaryl ring, monocyclic 3 to 10-membered cycloaliphatic ring, or monocyclic 4 to 10-membered heterocycle is optionally and independently substituted with up to 3 instances of $J^C$;

each $J^C$ is independently selected from halogen, —CN, —$NO_2$, a $C_{1-6}$ aliphatic, —$OR^H$, —$SR^H$, —$N(R^H)_2$, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^7$; or alternatively, two $J^C$ groups attached to two vicinal ring C atoms, taken together with said two vicinal ring C atoms, form a 5 to 7-membered heterocycle that is a new ring fused to ring C; wherein said 5 to 7-membered heterocycle contains from 1 to 2 heteroatoms independently selected from N, O or S;

each $R^H$ is independently selected from hydrogen, a $C_{1-6}$ aliphatic, a $C_{3-8}$ cycloaliphatic ring or a 4 to 8-membered heterocyclic ring; wherein each said 4 to 8-membered heterocylic ring contains between 1 and 3 heteroatoms independently selected from O, N or S; and wherein each said $C_{1-6}$ aliphatic, each said $C_{3-8}$ cycloaliphatic ring and each said 4 to 8-membered heterocyclic ring, is optionally and independently substituted with up to 3 instances of $R^{7a}$;

alternatively, two instances of $R^H$ linked to the same nitrogen atom of —$N(R^H)_2$, together with said nitrogen atom of —$N(R^H)_2$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^{7b}$;

each $R^7$ is independently selected from halogen, —CN, —$NO_2$, $C_{1-4}$ alkyl, $C_{1-4}$ haloalkyl, $C_{3-8}$ cycloalkyl ring, $C_{3-8}$ (halocycloalkyl) ring, —$OR^8$, —$SR^8$, —$N(R^8)_2$, or an oxo group;

each $R^{7a}$ is independently selected from halogen, —CN, —$NO_2$, $C_{1-4}$ alkyl, $C_{1-4}$ haloalkyl, $C_{3-8}$ cycloalkyl ring, $C_{3-8}$ (halocycloalkyl) ring, —$OR^8$, —$SR^8$, —$N(R^8)_2$, or an oxo group;

each $R^{7b}$ is independently selected from halogen, —CN, —$NO_2$, $C_{1-4}$ alkyl, $C_{1-4}$ haloalkyl, $C_{3-8}$ cycloalkyl ring, $C_{3-8}$ (halocycloalkyl) ring, —$OR^8$, —$SR^8$, —$N(R^8)_2$, or an oxo group;

each $R^{7c}$ is independently selected from hydrogen, halogen, —CN, —$NO_2$, $C_{1-4}$ alkyl, $C_{1-4}$ haloalkyl, $C_{3-8}$ cycloalkyl ring, —$OR^8$, —$SR^8$, —$N(R^8)_2$, or an oxo group; wherein each said cycloalkyl group is optionally and independently substituted with up to 3 instances of halogen;

each $R^{7d}$ is independently selected from hydrogen, halogen, —CN, —$NO_2$, $C_{1-4}$ alkyl, $C_{1-4}$ haloalkyl, $C_{3-8}$ cycloalkyl ring, —$OR^8$, —$SR^8$, —$N(R^8)_2$, or an oxo group; wherein each said cycloalkyl group is optionally and independently substituted with up to 3 instances of halogen;

each $R^{7e}$ is independently selected from hydrogen, halogen, —CN, —$NO_2$, $C_{1-4}$ alkyl, $C_{1-4}$ haloalkyl, $C_{3-8}$ cycloalkyl ring, —$OR^8$, —$SR^8$, —$N(R^8)_2$, or an oxo group; wherein each said cycloalkyl group is optionally and independently substituted with up to 3 instances of halogen;

each $R^8$ is independently selected from hydrogen, a $C_{1-4}$ alkyl, $C_{1-4}$ haloalkyl or a $C_{3-8}$ cycloalkyl ring, $C_{3-8}$ (halocycloalkyl) ring alternatively, two instances of $R^8$ linked to the same nitrogen atom of $R^7$, $R^{7a}$, $R^{7b}$, $R^{7c}$, $R^{7d}$ or $R^{7e}$, together with said nitrogen atom of $R^7$, $R^{7a}$, $R^{7b}$, $R^{7c}$, $R^{7d}$ or $R^{7e}$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; and $R^A$ is selected from hydrogen, halogen, $C_{1-4}$ alkyl or $C_{1-4}$ haloalkyl.

The present invention is also directed to compounds according to Formula I, or pharmaceutically acceptable salts thereof, Formula I

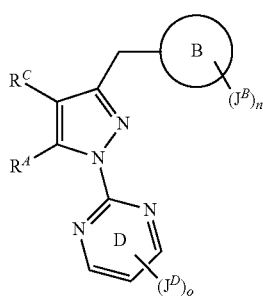

wherein, ring B is a phenyl or a 5 or 6-membered heteroaryl ring, containing 1 or 2 ring heteroatoms selected from N, O or S;
n is an integer selected from 0 to 3;
each $J^B$ is independently selected from halogen, —CN, a $C_{1-6}$ aliphatic, —OR$^B$ or a $C_{3-8}$ cycloaliphatic group; wherein each said $C_{1-6}$ aliphatic and each said $C_{3-8}$ cycloaliphatic group is optionally and independently substituted with up to 3 instances of $R^3$;
each $R^B$ is independently selected from hydrogen, a $C_{1-6}$ aliphatic or a $C_{3-8}$ cycloaliphatic; wherein each said $C_{1-6}$ aliphatic and each said $C_{3-8}$ cycloaliphatic ring is optionally and independently substituted with up to 3 instances of $R^{3a}$;
each $R^3$ is independently selected from halogen, —CN, $C_{1-4}$ alkyl, $C_{1-4}$ haloalkyl, —O($C_{1-4}$ alkyl) or —O($C_{1-4}$ haloalkyl);
each $R^{3a}$ is independently selected from halogen, —CN, $C_{1-4}$ alkyl, $C_{1-4}$ haloalkyl, —O($C_{1-4}$ alkyl) or —O($C_{1-4}$ haloalkyl);
is an integer selected from 0 to 3;
each $J^D$ is independently selected from halogen, —NO$_2$, —OR$^D$, —SR$^D$, —C(O)R$^D$, —C(O)OR$^D$, —C(O)N(R$^D$)$_2$, —CN, —N(R$^D$)$_2$, —N(R$^d$)C(O)R$^D$, —N(R$^d$)C(O)OR$^D$, —SO$_2$R$^D$, —SO$_2$N(R$^D$)$_2$, —N(R$^d$)SO$_2$R$^D$, a $C_{1-6}$ aliphatic, —(C$_{1-6}$ aliphatic)-R$^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocylic ring and each said 5 to 10-membered heteroaryl ring contains between 1 and 3 heteroatoms independently selected from O, N or S; and wherein each said $C_{1-6}$ aliphatic, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 3 instances of $R^5$;
each $R^D$ is independently selected from hydrogen, a $C_{1-6}$ aliphatic, —(C$_{1-6}$ aliphatic)-R$^f$, a $C_{3-8}$ cycloaliphatic ring, a 4 to 8-membered heterocyclic ring, phenyl or a 5 to 6-membered heteroaryl ring; wherein each said 4 to 8-membered heterocylic ring and each said 5 to 6-membered heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted with up to 3 instances of $R^{5a}$;
each $R^d$ is independently selected from hydrogen, a $C_{1-6}$ aliphatic, —(C$_{1-6}$ aliphatic)-R$^f$, a $C_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^{5b}$;
each $R^f$ is independently selected from a $C_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^{5c}$;
when $J^D$ is —C(O)N(R$^D$)$_2$, —N(R$^D$)$_2$ or —SO$_2$N(R$^D$)$_2$, the two R$^D$ groups together with the nitrogen atom attached to the R$^D$ groups alternatively form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;
when $J^D$ is —N(R$^d$)C(O)R$^D$, the R$^D$ group together with the carbon atom attached to the R$^D$ group, with the nitrogen atom attached to the R$^d$ group, and with the R$^d$ group alternatively form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;
when $J^D$ is —N(R$^d$)C(O)OR$^D$, the R$^D$ group together with the oxygen atom attached to the R$^D$ group, with the carbon atom of the —C(O)— portion of the —N(R$^d$)C(O)OR$^D$ group, with the nitrogen atom attached to the R$^d$ group, and with the R$^d$ group alternatively form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;
when $J^D$ is —N(R$^d$)SO$_2$R$^D$, the R$^D$ group together with the oxygen atom attached to the R$^D$ group, with the sulfur atom attached to said oxygen atom in the —SO$_2$R$^D$ portion of the —N(R$^d$)SO$_2$R$^D$ group, with the nitrogen atom attached to the R$^d$ group, and with the R$^d$ group alternatively form a 4 to 8-membered heterocyclic ring or a 5-membered heteroaryl ring;
wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;
each $R^5$ is independently selected from halogen, —CN, —NO$_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, —OR$^6$, —SR$^6$, —OCOR$^6$, —COR$^6$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl and each said cycloalkyl group is optionally and independently substituted with up to 3 instances of halogen;

each R$^{5a}$ is independently selected from halogen, —CN, —NO$_2$, C$_{1-4}$ alkyl, a C$_{7-12}$ aralkyl, C$_{3-8}$ cycloalkyl ring, C$_{1-4}$ haloalkyl, C$_{1-4}$ cyanoalkyl, —OR$^6$, —SR$^6$, —OCOR$^6$, —COR$^6$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl and each said cycloalkyl group is optionally and independently substituted with up to 3 instances of halogen;

each R$^{5b}$ is independently selected from halogen, —CN, —NO$_2$, C$_{1-4}$ alkyl, a C$_{7-12}$ aralkyl, C$_{3-8}$ cycloalkyl ring, C$_{1-4}$ haloalkyl, C$_{1-4}$ cyanoalkyl, —OR$^6$, —SR$^6$, —OCOR$^6$, —COR$^6$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl and each said cycloalkyl group is optionally and independently substituted with up to 3 instances of halogen;

each R$^{5c}$ is independently selected from halogen, —CN, —NO$_2$, C$_{1-4}$ alkyl, a C$_{7-12}$ aralkyl, C$_{3-8}$ cycloalkyl ring, C$_{1-4}$ haloalkyl, C$_{1-4}$ cyanoalkyl, —OR$^6$, —SR$^6$, —OCOR$^6$, —COR$^6$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl and each said cycloalkyl group is optionally and independently substituted with up to 3 instances of halogen;

each R$^6$ is independently selected from hydrogen, a C$_{1-4}$ alkyl, a C$_{2-4}$ alkenyl, phenyl, a C$_{7-12}$ aralkyl or a C$_{3-8}$ cycloalkyl ring; wherein each said C$_{1-4}$ alkyl, each said C$_{2-4}$ alkenyl, each said phenyl, each said C$_{7-12}$ aralkyl and each said cycloalkyl group is optionally and independently substituted with up to 3 instances of halogen;

alternatively, two instances of R$^6$ linked to the same nitrogen atom of R$^5$, together with said nitrogen atom of R$^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; or alternatively, one instance of R$^6$ linked to a nitrogen atom of R$^5$ and one instance of R$^6$ linked to a carbon or sulfur atom of the same R$^5$, together with said nitrogen and said carbon or sulfur atom of the same R$^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

or, alternatively, two J$^D$ groups attached to two vicinal ring D atoms, taken together with said two vicinal ring D atoms, form a 5 to 7-membered heterocycle resulting in a fused ring D wherein said 5 to 7-membered heterocycle contains from 1 to 3 heteroatoms independently selected from N, O or S; and wherein said 5 to 7-membered heterocycle is optionally and independently substituted by up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl), —O(C$_{1-4}$ haloalkyl), oxo or phenyl; wherein said phenyl is optionally and independently substituted by up to three instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl);

R$^C$ is a ring C; ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6-membered heteroaryl ring is not a 1,3,5-triazinyl ring; and wherein said phenyl, monocyclic 5 to 6-membered heteroaryl ring, bicyclic 8 to 10-membered heteroaryl ring, monocyclic 3 to 10-membered cycloaliphatic ring, or monocyclic 4 to 10-membered heterocycle is optionally and independently substituted with up to 3 instances of J$^C$.

each J$^C$ is independently selected from halogen, —CN, —NO$_2$, a C$_{1-6}$ aliphatic, —OR$^H$, —SR$^H$, —N(R$^H$)$_2$, a C$_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said C$_{1-6}$ aliphatic, each said C$_{3-8}$ cycloaliphatic ring and each said 4 to 8-membered heterocyclic ring, is optionally and independently substituted with up to 3 instances of R$^7$; or alternatively, two J$^C$ groups attached to two vicinal ring C atoms, taken together with said two vicinal ring C atoms, form a 5 to 7-membered heterocycle resulting in a fused ring C; wherein said 5 to 7-membered heterocycle contains from 1 to 2 heteroatoms independently selected from N, O or S;

each R$^H$ is independently selected from hydrogen, a C$_{1-6}$ aliphatic, a C$_{3-8}$ cycloaliphatic ring or a 4 to 8-membered heterocyclic ring; wherein each said 4 to 8-membered heterocylic ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, is optionally and independently substituted with up to 3 instances of R$^{7a}$;

alternatively, two instances of R$^H$ linked to the same nitrogen atom of J$^C$, together with said nitrogen atom of J$^C$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of R$^{7b}$;

each R$^7$ is independently selected from halogen, —CN, —NO$_2$, C$_{1-4}$ alkyl, C$_{1-4}$ haloalkyl, C$_{3-8}$ cycloalkyl ring, —OR, —SR$^8$, —N(R$^8$)$_2$, or an oxo group; wherein each said cycloalkyl group is optionally and independently substituted with up to 3 instances of halogen;

each R$^{7a}$ is independently selected from halogen, —CN, —NO$_2$, C$_{1-4}$ alkyl, C$_{1-4}$ haloalkyl, C$_{3-8}$ cycloalkyl ring, —OR, —SR$^8$, —N(R$^8$)$_2$, or an oxo group; wherein each said cycloalkyl group is optionally and independently substituted with up to 3 instances of halogen;

each $R^{7b}$ is independently selected from halogen, —CN, —NO$_2$, C$_{1-4}$ alkyl, C$_{1-4}$ haloalkyl, C$_{3-8}$ cycloalkyl ring, —OR, —SR$^8$, —N(R$^8$)$_2$, or an oxo group; wherein each said cycloalkyl group is optionally and independently substituted with up to 3 instances of halogen;

each $R^8$ is independently selected from hydrogen, a C$_{1-4}$ alkyl, C$_{1-4}$ haloalkyl or a C$_{3-8}$ cycloalkyl ring; wherein each said cycloalkyl group is optionally and independently substituted with up to 3 instances of halogen;

alternatively, two instances of R$^8$ linked to the same nitrogen atom of R$^7$, R$^{7a}$ or R$^{7b}$, together with said nitrogen atom of R$^7$, R$^{7a}$ or R$^{7b}$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; and $R^4$ is selected from hydrogen, halogen, C$_{1-4}$ alkyl or C$_{1-4}$ haloalkyl.

The invention also provides a method of treating or preventing a disease, health condition or disorder in a subject in need thereof, comprising administering, alone or in combination therapy, a therapeutically or prophylactically effective amount of a compound of Formula I or Formula Ib or a pharmaceutically acceptable salt thereof to the subject; wherein the disease, health condition or disorder is a peripheral, pulmonary, hepatic, liver, cardiac or cerebral vascular/endothelial disorder or condition, a urogenital-gynecological disorder or condition, a thromboembolic disease, a fibrotic disorder, or other pulmonary or respiratory disorder, renal or hepatic disorder, metabolic disorder, atherosclerosis or a lipid related disorder that can benefit from sGC stimulation or from an increase in the concentration of NO or cGMP.

DETAILED DESCRIPTION

Reference will now be made in detail to certain embodiments of the invention, examples of which are illustrated in the accompanying structures and formulae. While the invention will be described in conjunction with the enumerated embodiments, it will be understood that they are not intended to limit the invention to those embodiments. Rather, the invention is intended to cover all alternatives, modifications and equivalents that may be included within the scope of the present invention as defined by the claims. The present invention is not limited to the methods and materials described herein but include any methods and materials similar or equivalent to those described herein that could be used in the practice of the present invention. In the event that one or more of the incorporated literature references, patents or similar materials differ from or contradict this application, including but not limited to defined terms, term usage, described techniques or the like, this application controls.

Definitions and General Terminology

For purposes of this disclosure, the chemical elements are identified in accordance with the Periodic Table of the Elements, CAS version, and the Handbook of Chemistry and Physics, 75$^{th}$ Ed. 1994. Additionally, general principles of organic chemistry are described in "Organic Chemistry", Thomas Sorrell, University Science Books, Sausalito: 1999, and "March's Advanced Organic Chemistry", 5$^{th}$ Ed., Smith, M. B. and March, J., eds. John Wiley & Sons, New York: 2001, which are herein incorporated by reference in their entirety.

As described herein, compounds of Formula I or Formula Ib may be optionally substituted with one or more substituents, such as illustrated generally below, or as exemplified by particular classes, subclasses and species of the invention. The phrase "optionally substituted" is used interchangeably with the phrase "substituted or unsubstituted." In general, the term "substituted" refers to the replacement of one or more hydrogen radicals in a given structure with the radical of a specified substituent. Unless otherwise indicated, an optionally substituted group may have a substituent at each substitutable position of the group. When more than one position in a given structure can be substituted with more than one substituent selected from a specified group, the substituent may be either the same or different at each position unless otherwise specified. As will be apparent to one of ordinary skill in the art, groups such as —H, halogen, —NO$_2$, —CN, —OH, —NH$_2$ or —OCF$_3$ would not be substitutable groups.

The phrase "up to", as used herein, refers to zero or any integer number that is equal or less than the number following the phrase. For example, "up to 3" means any one of 0, 1, 2, or 3. As described herein, a specified number range of atoms includes any integer therein. For example, a group having from 1-4 atoms could have 1, 2, 3 or 4 atoms. When any variable occurs more than one time at any position, its definition on each occurrence is independent from every other occurrence.

Selection of substituents and combinations envisioned by this disclosure are only those that result in the formation of stable or chemically feasible compounds. Such choices and combinations will be apparent to those of ordinary skill in the art and may be determined without undue experimentation. The term "stable", as used herein, refers to compounds that are not substantially altered when subjected to conditions to allow for their production, detection, and, in some embodiments, their recovery, purification, and use for one or more of the purposes disclosed herein. In some embodiments, a stable compound or chemically feasible compound is one that is not substantially altered when kept at a temperature of 25° C. or less, in the absence of moisture or other chemically reactive conditions, for at least a week. A chemically feasible compound is a compound that can be prepared by a person skilled in the art based on the disclosures herein supplemented, if necessary, relevant knowledge of the art.

A compound, such as the compounds of Formula I or Formula Ib or other compounds herein disclosed, may be present in its free form (e.g. an amorphous form, or a crystalline form or a polymorph). Under certain conditions, compounds may also form co-forms. As used herein, the term co-form is synonymous with the term multi-component crystalline form. When one of the components in the co-form has clearly transferred a proton to the other component, the resulting co-form is referred to as a "salt". The formation of a salt is determined by how large the difference is in the pKas between the partners that form the mixture.

Unless only one of the isomers is drawn or named specifically, structures depicted herein are also meant to include all stereoisomeric (e.g., enantiomeric, diastereomeric, atropoisomeric and cis-trans isomeric) forms of the structure; for example, the R and S configurations for each asymmetric center, Ra and Sa configurations for each asymmetric axis, (Z) and (E) double bond configurations, and cis and trans conformational isomers. Therefore, single stereochemical isomers as well as racemates, and mixtures of enantiomers, diastereomers, and cis-trans isomers (double bond or conformational) of the present compounds are within the scope of the present disclosure. Unless otherwise stated, all tautomeric forms of the compounds of the present disclosure are also within the scope of the invention.

The present disclosure also embraces isotopically-labeled compounds which are identical to those recited herein, but for the fact that one or more atoms are replaced by an atom having an atomic mass or mass number different from the atomic mass or mass number usually found in nature. All isotopes of any particular atom or element as specified are contemplated within the scope of the compounds of the invention, and their uses. Exemplary isotopes that can be incorporated into compounds of the invention include isotopes of hydrogen, carbon, nitrogen, oxygen, phosphorus, sulfur, fluorine, chlorine, and iodine, such as $^2$H, $^3$H, $^{11}$C, $^{13}$C, $^{14}$C, $^{13}$N, $^{15}$N, $^{15}$O, $^{17}$O, $^{18}$O, $^{32}$P, $^{33}$P, $^{35}$S, $^{18}$F, $^{36}$Cl, $^{123}$I, and $^{125}$I, respectively. Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are useful for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

The term "aliphatic" or "aliphatic group", as used herein, means a straight-chain (i.e., unbranched) or branched, substituted or unsubstituted hydrocarbon chain that is completely saturated or that contains one or more units of unsaturation. Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms. In other embodiments, aliphatic groups contain 1-4 aliphatic carbon atoms and in yet other embodiments, aliphatic groups contain 1-3 aliphatic carbon atoms. Suitable aliphatic groups include, but are not limited to, linear or branched, substituted or unsubstituted alkyl, alkenyl, or alkynyl groups. Specific examples of aliphatic groups include, but are not limited to: methyl, ethyl, propyl, butyl, isopropyl, isobutyl, vinyl, sec-butyl, tert-butyl, butenyl, propargyl, acetylene and the like.

The term "alkyl", as used herein, refers to a saturated linear or branched-chain monovalent hydrocarbon radical. Unless otherwise specified, an alkyl group contains 1-20 carbon atoms (e.g., 1-20 carbon atoms, 1-10 carbon atoms, 1-8 carbon atoms, 1-6 carbon atoms, 1-4 carbon atoms or 1-3 carbon atoms). Examples of alkyl groups include, but are not limited to, methyl, ethyl, n-propyl, isopropyl, n-butyl, isobutyl, s-butyl, t-butyl, pentyl, hexyl, heptyl, octyl and the like.

The term "alkenyl" refers to a linear or branched-chain monovalent hydrocarbon radical with at least one site of unsaturation, i.e., a carbon-carbon, sp$^2$ double bond, wherein the alkenyl radical includes radicals having "cis" and "trans" orientations, or alternatively, "E" and "Z" orientations. Unless otherwise specified, an alkenyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, vinyl, allyl and the like.

The term "alkynyl" refers to a linear or branched monovalent hydrocarbon radical with at least one site of unsaturation, i.e., a carbon-carbon sp triple bond. Unless otherwise specified, an alkynyl group contains 2-20 carbon atoms (e.g., 2-20 carbon atoms, 2-10 carbon atoms, 2-8 carbon atoms, 2-6 carbon atoms, 2-4 carbon atoms or 2-3 carbon atoms). Examples include, but are not limited to, ethynyl, propynyl, and the like.

The term "carbocyclic" refers to a ring system formed only by carbon and hydrogen atoms. Unless otherwise specified, throughout this disclosure, carbocycle is used as a synonym of "non-aromatic carbocycle" or "cycloaliphatic". In some instances the term can be used in the phrase "aromatic carbocycle", and in this case it refers to an "aryl group" as defined below.

The term "cycloaliphatic" (or "non-aromatic carbocycle", "non-aromatic carbocyclyl", "non-aromatic carbocyclic") refers to a cyclic hydrocarbon that is completely saturated or that contains one or more units of unsaturation but which is not aromatic, and which has a single point of attachment to the rest of the molecule. Unless otherwise specified, a cycloaliphatic group may be monocyclic, bicyclic, tricyclic, fused, spiro or bridged. In one embodiment, the term "cycloaliphatic" refers to a monocyclic $C_3$-$C_{12}$ hydrocarbon or a bicyclic $C_7$-$C_{12}$ hydrocarbon. In some embodiments, any individual ring in a bicyclic or tricyclic ring system has 3-7 members. Suitable cycloaliphatic groups include, but are not limited to, cycloalkyl, cycloalkenyl, and cycloalkynyl. Examples of aliphatic groups include cyclopropyl, cyclobutyl, cyclopentyl, cyclopentenyl, cyclohexyl, cyclohexenyl, cycloheptyl, cycloheptenyl, norbornyl, cyclooctyl, cyclononyl, cyclodecyl, cycloundecyl, cyclododecyl, and the like.

The term "cycloaliphatic" also includes polycyclic ring systems in which the non-aromatic carbocyclic ring can be "fused" to one or more aromatic or non-aromatic carbocyclic or heterocyclic rings or combinations thereof, as long as the radical or point of attachment is on the non-aromatic carbocyclic ring.

"Heterocycle" (or "heterocyclyl" or "heterocyclic), as used herein, refers to a ring system in which one or more ring members are an independently selected heteroatom, which is completely saturated or that contains one or more units of unsaturation but which is not aromatic, and which has a single point of attachment to the rest of the molecule. Unless otherwise specified, through this disclosure, heterocycle is used as a synonym of "non-aromatic heterocycle". In some instances the term can be used in the phrase "aromatic heterocycle", and in this case it refers to a "heteroaryl group" as defined below. The term heterocycle also includes fused, spiro or bridged heterocyclic ring systems. Unless otherwise specified, a heterocycle may be monocyclic, bicyclic or tricyclic. In some embodiments, the heterocycle has 3-18 ring members in which one or more ring members is a heteroatom independently selected from oxygen, sulfur or nitrogen, and each ring in the system contains 3 to 7 ring members. In other embodiments, a heterocycle may be a monocycle having 3-7 ring members (2-6 carbon atoms and 1-4 heteroatoms) or a bicycle having 7-10 ring members (4-9 carbon atoms and 1-6 heteroatoms). Examples of bicyclic heterocyclic ring systems include, but are not limited to: adamantanyl, 2-oxa-bicyclo[2.2.2]octyl, 1-aza-bicyclo[2.2.2]octyl.

As used herein, the term "heterocycle" also includes polycyclic ring systems wherein the heterocyclic ring is fused with one or more aromatic or non-aromatic carbocyclic or heterocyclic rings, or with combinations thereof, as long as the radical or point of attachment is on the heterocyclic ring.

Examples of heterocyclic rings include, but are not limited to, the following monocycles: 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl; and the following bicycles: 3-1H-benzimidazol-2-one, 3-(1-alkyl)-benzimidazol-2-one, indolinyl, tetrahydroquinolinyl, tetrahydroisoquinolinyl, benzothiolane, benzodithiane, and 1,3-dihydro-imidazol-2-one.

As used herein, the term "aryl" (as in "aryl ring" or "aryl group"), used alone or as part of a larger moiety, as in "aralkyl", "aralkoxy", "aryloxyalkyl", refers to a carbocyclic ring system wherein at least one ring in the system is aromatic and has a single point of attachment to the rest of the molecule. Unless otherwise specified, an aryl group may be monocyclic, bicyclic or tricyclic and contain 6-18 ring members. The term also includes polycyclic ring systems where the aryl ring is fused with one or more aromatic or non-aromatic carbocyclic or heterocyclic rings, or with combinations thereof, as long as the radical or point of attachment is in the aryl ring. Examples of aryl rings include, but are not limited to, phenyl, naphthyl, indanyl, indenyl, tetralin, fluorenyl, and anthracenyl.

The term "aralkyl" refers to a radical having an aryl ring substituted with an alkylene group, wherein the open end of the alkylene group allows the aralkyl radical to bond to another part of the compound of Formula I or Formula Ib. The alkylene group is a bivalent, straight-chain or branched, saturated hydrocarbon group. As used herein, the term "$C_{7-12}$ aralkyl" means an aralkyl radical wherein the total number of carbon atoms in the aryl ring and the alkylene group combined is 7 to 12. Examples of "aralkyl" include, but are not limited to, a phenyl ring substituted by a $C_{1-6}$ alkylene group, e.g., benzyl and phenylethyl, and a naphthyl group substituted by a $C_{1-2}$ alkylene group.

The term "heteroaryl" (or "heteroaromatic" or "heteroaryl group" or "aromatic heterocycle") used alone or as part of a larger moiety as in "heteroaralkyl" or "heteroarylalkoxy" refers to a ring system wherein at least one ring in the system is aromatic and contains one or more heteroatoms, wherein each ring in the system contains 3 to 7 ring members and which has a single point of attachment to the rest of the molecule. Unless otherwise specified, a heteroaryl ring system may be monocyclic, bicyclic or tricyclic and have a total of five to fourteen ring members. In one embodiment, all rings in a heteroaryl system are aromatic. Also included in this definition are heteroaryl radicals where the heteroaryl ring is fused with one or more aromatic or non-aromatic carbocyclic or heterocyclic rings, or combinations thereof, as long as the radical or point of attachment is in the heteroaryl ring. Bicyclic 6, 5 heteroaromatic system, as used herein, for example, is a six membered heteroaromatic ring fused to a second five membered ring wherein the radical or point of attachment is on the six-membered ring.

Heteroaryl rings include, but are not limited to the following monocycles: 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, pyrazinyl, 1,3,5-triazinyl, and the following bicycles: benzimidazolyl, benzofuryl, benzothiophenyl, benzopyrazinyl, benzopyranonyl, indolyl (e.g., 2-indolyl), purinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

As used herein, "cyclo" (or "cyclic", or "cyclic moiety") encompasses mono-, bi- and tri-cyclic ring systems including cycloaliphatic, heterocyclic, aryl or heteroaryl, each of which has been previously defined.

"Fused" bicyclic ring systems comprise two rings which share two adjoining ring atoms.

"Bridged" bicyclic ring systems comprise two rings which share three or four adjacent ring atoms. As used herein, the term "bridge" refers to an atom or a chain of atoms connecting two different parts of a molecule. The two atoms that are connected through the bridge (usually but not always, two tertiary carbon atoms) are referred to as "bridgeheads". In addition to the bridge, the two bridgeheads are connected by at least two individual atoms or chains of atoms. Examples of bridged bicyclic ring systems include, but are not limited to, adamantanyl, norbornanyl, bicyclo[3.2.1]octyl, bicyclo[2.2.2]octyl, bicyclo[3.3.1]nonyl, bicyclo[3.2.3]nonyl, 2-oxa-bicyclo[2.2.2]octyl, 1-aza-bicyclo[2.2.2]octyl, 3-aza-bicyclo[3.2.1]octyl, and 2,6-dioxatricyclo[3.3.1.03,7]nonyl. "Spiro" bicyclic ring systems share only one ring atom (usually a quaternary carbon atom) between the two rings.

The term "ring atom" refers to an atom such as C, N, O or S that is part of the ring of an aromatic ring, a cycloaliphatic ring, a heterocyclic or a heteroaryl ring. A "substitutable ring atom" is a ring carbon or nitrogen atom bonded to at least one hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to one or more moiety other than hydrogen and no hydrogens are available for substitution.

"Heteroatom" refers to one or more of oxygen, sulfur, nitrogen, phosphorus, or silicon, including any oxidized form of nitrogen, sulfur, phosphorus, or silicon, the quaternized form of any basic nitrogen, or a substitutable nitrogen of a heterocyclic or heteroaryl ring, for example N (as in 3,4-dihydro-2H-pyrrolyl), NH (as in pyrrolidinyl) or $NR^+$ (as in N-substituted pyrrolidinyl).

In some embodiments, two independent occurrences of a variable may be taken together with the atom(s) to which each variable is bound to form a 5-8-membered, heterocyclyl, aryl, or heteroaryl ring or a 3-8-membered cycloaliphatic ring. Exemplary rings that are formed when two independent occurrences of a substituent are taken together with the atom(s) to which each variable is bound include, but are not limited to the following: a) two independent occurrences of a substituent that are bound to the same atom and are taken together with that atom to form a ring, where both occurrences of the substituent are taken together with the atom to which they are bound to form a heterocyclyl, heteroaryl, cycloaliphatic or aryl ring, wherein the group is attached to the rest of the molecule by a single point of attachment; and b) two independent occurrences of a substituent that are bound to different atoms and are taken together with both of those atoms to form a heterocyclyl, heteroaryl, cycloaliphatic or aryl ring, wherein the ring that is formed has two points of attachment with the rest of the molecule. For example, where a phenyl group is substituted with two occurrences of —OR° as in Formula D1:

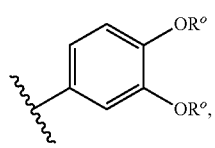

these two occurrences of —OR° are taken together with the carbon atoms to which they are bound to form a fused 6-membered oxygen containing ring as in Formula D2:

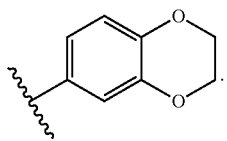

It will be appreciated that a variety of other rings can be formed when two independent occurrences of a substituent are taken together with the atom(s) to which each substituent is bound and that the examples detailed above are not intended to be limiting.

In some embodiments, an alkyl or aliphatic chain can be optionally interrupted with another atom or group. This means that a methylene unit of the alkyl or aliphatic chain can optionally be replaced with said other atom or group. Unless otherwise specified, the optional replacements form a chemically stable compound. Optional interruptions can occur both within the chain and/or at either end of the chain; i.e. both at the point of attachment(s) to the rest of the molecule and/or at the terminal end. Two optional replacements can also be adjacent to each other within a chain so long as it results in a chemically stable compound. Unless otherwise specified, if the replacement or interruption occurs at a terminal end of the chain, the replacement atom is bound to an H on the terminal end. For example, if —CH$_2$CH$_2$CH$_3$ were optionally interrupted with —O—, the resulting compound could be —OCH$_2$CH$_3$, —CH$_2$OCH$_3$, or —CH$_2$CH$_2$OH. In another example, if the divalent linker —CH$_2$CH$_2$CH$_2$— were optionally interrupted with —O—, the resulting compound could be —OCH$_2$CH$_2$—, —CH$_2$OCH$_2$—, or —CH$_2$CH$_2$O—. The optional replacements can also completely replace all of the carbon atoms in a chain. For example, a C$_3$ aliphatic can be optionally replaced by —N(R')—, —C(O)—, and —N(R')— to form —N(R')C(O)N(R')—(a urea).

In general, the term "vicinal" refers to the placement of substituents on a group that includes two or more carbon atoms, wherein the substituents are attached to adjacent carbon atoms.

In general, the term "geminal" refers to the placement of substituents on a group that includes two or more carbon atoms, wherein the substituents are attached to the same carbon atom.

The terms "terminally" and "internally" refer to the location of a group within a substituent. A group is terminal when the group is present at the end of the substituent not further bonded to the rest of the chemical structure. Carboxyalkyl, i.e., R$^X$O(O)C-alkyl is an example of a carboxy group used terminally. A group is internal when the group is present in the middle of a substituent at the end of the substituent bound to the rest of the chemical structure. Alkylcarboxy (e.g., alkyl-C(O)O— or alkyl-O(CO)—) and alkylcarboxyaryl (e.g., alkyl-C(O)O-aryl- or alkyl-O(CO)-aryl-) are examples of carboxy groups used internally.

As described herein, a bond drawn from a substituent to the center of one ring within a multiple-ring system (as shown below), represents substitution of the substituent at any substitutable position in any of the rings within the multiple ring system. For example, formula D3 represents possible substitution in any of the positions shown in formula D4:

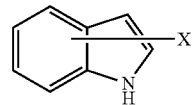

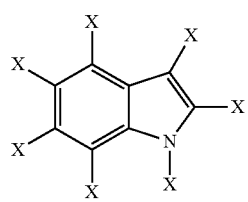

This also applies to multiple ring systems fused to optional ring systems (which would be represented by dotted lines). For example, in Formula D5, X is an optional substituent both for ring A and ring B.

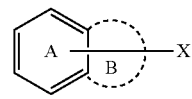

If, however, two rings in a multiple ring system each have different substituents drawn from the center of each ring, then, unless otherwise specified, each substituent only represents substitution on the ring to which it is attached. For example, in Formula D6, Y is an optional substituent for ring A only, and X is an optional substituent for ring B only.

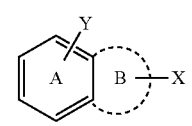

As used herein, the terms "alkoxy" or "alkylthio" refer to an alkyl group, as previously defined, attached to the molecule, or to another chain or ring, through an oxygen ("alkoxy" i.e., —O-alkyl) or a sulfur ("alkylthio" i.e., —S-alkyl) atom.

The terms $C_{n\text{-}m}$ "alkoxyalkyl", $C_{n\text{-}m}$ "alkoxyalkenyl", $C_{n\text{-}m}$ "alkoxyaliphatic", and $C_{n\text{-}m}$ "alkoxyalkoxy" mean alkyl, alkenyl, aliphatic or alkoxy, as the case may be, substituted with one or more alkoxy groups, wherein the combined total number of carbons of the alkyl and alkoxy groups, alkenyl and alkoxy groups, aliphatic and alkoxy groups or alkoxy and alkoxy groups, combined, as the case may be, is between the values of n and m. For example, a $C_{4\text{-}6}$ alkoxyalkyl has a total of 4-6 carbons divided between the alkyl and alkoxy portion; e.g. it can be —CH$_2$OCH$_2$CH$_2$CH$_3$, —CH$_2$CH$_2$OCH$_2$CH$_3$ or —CH$_2$CH$_2$CH$_2$OCH$_3$.

When the moieties described in the preceding paragraph are optionally substituted, they can be substituted in either or both of the portions on either side of the oxygen or sulfur. For example, an optionally substituted $C_4$ alkoxyalkyl could be, for instance, —CH$_2$CH$_2$OCH$_2$(Me)CH$_3$ or —CH$_2$(OH)OCH$_2$CH$_2$CH$_3$; a $C_5$ alkoxyalkenyl could be, for instance, —CH═CHOCH$_2$CH$_2$CH$_3$ or —CH═CH—CH$_2$OCH$_2$CH$_3$.

The terms aryloxy, arylthio, benzyloxy or benzylthio, refer to an aryl or benzyl group attached to the molecule, or to another chain or ring, through an oxygen ("aryloxy", benzyloxy e.g., —O-Ph, —OCH$_2$Ph) or sulfur ("arylthio" e.g., —S-Ph, —S—CH$_2$Ph) atom. Further, the terms "aryloxyalkyl", "benzyloxyalkyl" "aryloxyalkenyl" and "aryloxyaliphatic" mean alkyl, alkenyl or aliphatic, as the case may be, substituted with one or more aryloxy or benzyloxy groups, as the case may be. In this case, the number of atoms for each aryl, aryloxy, alkyl, alkenyl or aliphatic will be indicated separately. Thus, a 5-6-membered aryloxy($C_{1\text{-}4}$ alkyl) is a 5-6 membered aryl ring, attached via an oxygen atom to a $C_{1\text{-}4}$ alkyl chain which, in turn, is attached to the rest of the molecule via the terminal carbon of the $C_{1\text{-}4}$ alkyl chain.

As used herein, the terms "halogen" or "halo" mean F, Cl, Br, or I.

The terms "haloalkyl", "haloalkenyl", "haloaliphatic", and "haloalkoxy" mean alkyl, alkenyl, aliphatic or alkoxy, as the case may be, substituted with one or more halogen atoms. For example a $C_{1\text{-}3}$ haloalkyl could be —CFHCH$_2$CHF$_2$ and a $C_{1\text{-}2}$ haloalkoxy could be —OC(Br)HCHF$_2$. This term includes perfluorinated alkyl groups, such as —CF$_3$ and —CF$_2$CF$_3$.

As used herein, the term "cyano" refers to —CN or —C≡N.

The terms "cyanoalkyl", "cyanoalkenyl", "cyanoaliphatic", and "cyanoalkoxy" mean alkyl, alkenyl, aliphatic or alkoxy, as the case may be, substituted with one or more cyano groups. For example a $C_{1\text{-}3}$ cyanoalkyl could be —C(CN)$_2$CH$_2$CH$_3$ and a $C_{1\text{-}2}$ cyanoalkenyl could be ═CHC(CN)H$_2$.

As used herein, an "amino" group refers to —NH$_2$.

The terms "aminoalkyl", "aminoalkenyl", "aminoaliphatic", and "aminoalkoxy" mean alkyl, alkenyl, aliphatic or alkoxy, as the case may be, substituted with one or more amino groups. For example a $C_{1\text{-}3}$ aminoalkyl could be —CH(NH$_2$)CH$_2$CH$_2$NH$_2$ and a $C_{1\text{-}2}$ aminoalkoxy could be —OCH$_2$CH$_2$NH$_2$.

The term "hydroxyl" or "hydroxy" refers to —OH.

The terms "hydroxyalkyl", "hydroxyalkenyl", "hydroxyaliphatic", and "hydroxyalkoxy" mean alkyl, alkenyl, aliphatic or alkoxy, as the case may be, substituted with one or more —OH groups. For example a $C_{1\text{-}3}$ hydroxyalkyl could be —CH$_2$(CH$_2$OH)CH$_3$ and a $C_4$ hydroxyalkoxy could be —OCH$_2$C(CH$_3$)(OH)CH$_3$.

As used herein, a "carbonyl", used alone or in connection with another group refers to —C(O)— or —C(O)H. For example, as used herein, an "alkoxycarbonyl," refers to a group such as —C(O)O(alkyl).

As used herein, an "oxo" refers to ═O, wherein oxo is usually, but not always, attached to a carbon atom (e.g., it can also be attached to a sulfur atom). An aliphatic chain can be optionally interrupted by a carbonyl group or can optionally be substituted by an oxo group, and both expressions refer to the same: e.g. —CH$_2$—C(O)—CH$_3$.

As used herein, in the context of resin chemistry (e.g. using solid resins or soluble resins or beads), the term "linker" refers to a bifunctional chemical moiety attaching a compound to a solid support or soluble support.

In all other situations, a "linker", as used herein, refers to a divalent group in which the two free valences are on different atoms (e.g. carbon or heteroatom) or are on the same atom but can be substituted by two different substituents. For example, a methylene group can be $C_1$ alkyl linker (—CH$_2$—) which can be substituted by two different groups, one for each of the free valences (e.g. as in Ph-CH$_2$-Ph, wherein methylene acts as a linker between two phenyl rings). Ethylene can be $C_2$ alkyl linker (—CH$_2$CH$_2$—) wherein the two free valences are on different atoms. The amide group, for example, can act as a linker when placed in an internal position of a chain (e.g. —CONH—). A linker can be the result of interrupting an aliphatic chain by certain functional groups or of replacing methylene units on said chain by said functional groups. E.g. a linker can be a $C_{1\text{-}6}$ aliphatic chain in which up to two methylene units are substituted by —C(O)— or —NH— (as in —CH$_2$—NH—CH$_2$—C(O)—CH$_2$— or —CH$_2$—NH—C(O)—CH$_2$—). An alternative way to define the same —CH$_2$—NH—CH$_2$—C(O)—CH$_2$— and —CH$_2$—NH—C(O)—CH$_2$— groups is as a $C_3$ alkyl chain optionally interrupted by up to two —C(O)— or —NH— moieties. Cyclic groups can also form linkers: e.g. a 1,6-cyclohexanediyl can be a linker between two R groups, as in

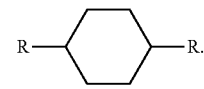

A linker can additionally be optionally substituted in any portion or position.

Divalent groups of the type R—CH═ or R$_2$C═, wherein both free valences are in the same atom and are attached to the same substituent, are also possible. In this case, they will be referred to by their IUPAC accepted names. For instance an alkylidene (such as, for example, a methylidene (═CH$_2$) or an ethylidene (═CH—CH$_3$)) would not be encompassed by the definition of a linker in this disclosure.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W. et al., "Protective Groups in Organic Synthesis", Third Edition, John Wiley & Sons, New York: 1999, the entire contents of which is hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are detailed in Chapter 7 in Greene, T. W., Wuts, P. G in "Protective Groups in Organic Synthesis", Third Edition, John Wiley & Sons, New York: 1999, the entire contents of which are hereby incorporated by reference.

As used herein, the term "displaceable moiety" or "leaving group" refers to a group that is associated with an aliphatic or aromatic group as defined herein and is subject to being displaced by nucleophilic attack by a nucleophile.

As used herein, "amide coupling agent" or "amide coupling reagent" means a compound that reacts with the hydroxyl moiety of a carboxy moiety thereby rendering it susceptible to nucleophilic attack. Exemplary amide coupling agents include DIC (diisopropylcarbodiimide), EDCI (1-ethyl-3-(3-dimethylaminopropyl)carbodiimide), DCC (dicyclohexylcarbodiimide), BOP (benzotriazol-1-yloxy-tris (dimethylamino)-phosphonium hexafluorophosphate), pyBOP ((benzotriazol-1-yloxy)tripyrrolidinophosphonium hexafluorophosphate), etc.

The compounds of the invention are defined herein by their chemical structures and/or chemical names. Where a compound is referred to by both a chemical structure and a chemical name, and the chemical structure and chemical name conflict, the chemical structure is determinative of the compound's identity.

Compound Embodiments

The present invention includes compounds of Formula I or Formula Ib, or pharmaceutically acceptable salts thereof,

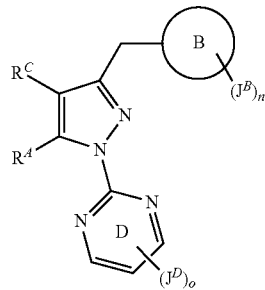

Formula I

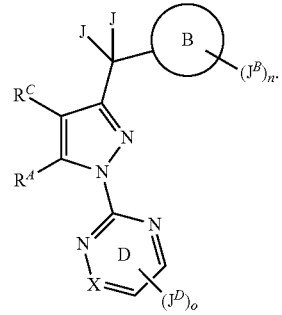

Formula Ib

In the compounds of Formula Ib:
X is either carbon or nitrogen;
wherein either
i) ring B is absent with $J^B$ connected directly to the carbon atom bearing two J groups, each J is independently selected from hydrogen, methyl or fluorine, n is 1 and $J^B$ is a $C_{1-6}$ alkyl chain optionally substituted by up to 6 instances of fluorine; or ii) ring B is a phenyl or a 5 or 6-membered heteroaryl ring, containing 1 or 2 ring heteroatoms selected from N, O or S; wherein with ring B being the phenyl or 5 or 6-membered heteroaryl ring; each J is hydrogen; n is an integer selected from 0 to 3; and each $J^B$ is independently selected from halogen, —CN, a $C_{1-6}$ aliphatic, —$OR^B$ or a $C_{3-8}$ cycloaliphatic group; wherein each said $C_{1-6}$ aliphatic and each said $C_{3-8}$ cycloaliphatic group is optionally and independently substituted with up to 3 instances of $R^3$; each $R^B$ is independently selected from hydrogen, a $C_{1-6}$ aliphatic or a $C_{3-8}$ cycloaliphatic; wherein each said $C_{1-6}$ aliphatic and each said $C_{3-8}$ cycloaliphatic ring is optionally and independently substituted with up to 3 instances of $R^{3a}$;

each $R^3$ is independently selected from halogen, —CN, $C_{1-4}$ alkyl, $C_{1-4}$ haloalkyl, —O($C_{1-4}$ alkyl) or —O($C_{1-4}$ haloalkyl);

each $R^{3a}$ is independently selected from halogen, —CN, $C_{1-4}$ alkyl, $C_{1-4}$ haloalkyl, —O($C_{1-4}$ alkyl) or —O($C_{1-4}$ haloalkyl);

o is an integer selected from 0 to 3;

each $J^D$ is independently selected from halogen, —CN, —$OR^D$, —$SR^D$, —C(O)$R^D$, —C(O)O$R^D$, —OC(O)$R^D$, —C(O)N($R^D$)$_2$, —N($R^D$)$_2$, —N($R^d$)C(O)$R^D$, —N($R^d$)C(O)O$R^D$, —N($R^d$)C(O)N($R^D$)$_2$, —OC(O)N($R^D$)$_2$, —SO$_2R^D$, —SO$_2$N($R^D$)$_2$, —N($R^d$)SO$_2R^D$, a $C_{1-6}$ aliphatic, —($C_{1-6}$ aliphatic)-$R^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocyclic ring and each said 5 to 10-membered heteroaryl ring contains between 1 and 3 heteroatoms independently selected from O, N or S; and wherein each said $C_{1-6}$ aliphatic, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 3 instances of $R^5$;

each $R^D$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocyclic ring and each said 5 to 6-membered heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted with up to 3 instances of $R^{5a}$;

each $R^d$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said heterocyclic ring and each said heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^{5b}$;

each $R^f$ is independently selected from a $C_{3-8}$ cycloaliphatic ring, a 4 to 8-membered heterocyclic ring, phenyl or a 5 to 6-membered heteroaryl ring; wherein each said heterocyclic ring and each said heteroaryl ring contains between 1 and 3 heteroatoms independently selected from O, N or S; and wherein each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^{5c}$;

when $J^D$ is —C(O)N($R^D$)$_2$, —N($R^D$)$_2$, —N($R^d$)C(O)N($R^D$)$_2$, —OC(O)N($R^D$)$_2$ or —SO$_2$N($R^D$)$_2$, the two $R^D$ groups together with the nitrogen atom attached to the two $R^D$ groups may form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S; and wherein each said 4 to 8-membered heterocyclic ring and each said 5-membered heteroaryl ring is optionally and independently substituted by up to 3 instances of $R^{5d}$;

when $J^D$ is —N($R^d$)C(O)$R^D$ the $R^D$ group together with the carbon atom attached to the $R^D$ group, with the nitrogen atom attached to the $R^d$ group, and with the $R^d$ group may form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^{5d}$;

when $J^D$ is —N($R^d$)C(O)O$R^D$ or —N($R^d$)C(O)N($R^D$)$_2$, the $R^D$ group together with the oxygen atom attached to the $R^D$ group, with the carbon atom of the —C(O)— portion of the —N($R^d$)C(O)O$R^D$ group, with the nitrogen atom attached to the $R^d$ group, or, alternatively one of the $R^D$ groups attached to the nitrogen atom, together with said nitrogen atom, and with the N atom attached to the $R^d$ group and said $R^d$ group may form a 4 to 8-membered heterocyclic ring; wherein said 4 to 8-membered heterocyclic ring optionally contains up to 2 additional heteroatoms independently selected from N, O or S, and is optionally and independently substituted by up to 3 instances of $R^{5d}$;

when $J^D$ is —N($R^d$)SO$_2$$R^D$, the $R^D$ group together with the sulfur atom attached to the $R^D$ group, with the nitrogen atom attached to the $R^d$ group, and with the $R^d$ group may combine to form a 4 to 8-membered heterocyclic ring; wherein said 4 to 8-membered heterocyclic ring optionally contains up to 2 additional heteroatoms independently selected from N, O or S, and is optionally and independently substituted by up to 3 instances of $R^{5d}$;

each $R^5$ is independently selected from halogen, —CN, C$_{1-4}$ alkyl, —(C$_{1-4}$ alkyl)-R$^6$, a C$_{7-12}$ aralkyl, C$_{3-8}$ cycloalkyl ring, C$_{1-4}$ cyanoalkyl, —OR$^6$, —SR$^6$, —OCOR$^6$, —COR$^6$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl, each said C$_{1-4}$ alkyl chain and each said C$_{3-8}$ cycloalkyl group is optionally and independently substituted with up to 3 instances of halogen;

each $R^{5a}$ is independently selected from halogen, —CN, C$_{1-4}$ alkyl, —(C$_{1-4}$ alkyl)-R$^6$, a C$_{7-12}$ aralkyl, C$_{3-8}$ cycloalkyl ring, C$_{1-4}$ cyanoalkyl, —OR$^6$, —SR$^6$, —OCOR$^6$, —COR$^6$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl, each said C$_{1-4}$ alkyl chain and each said C$_{3-8}$ cycloalkyl group is optionally and independently substituted with up to 3 instances of halogen;

each $R^{5b}$ is independently selected from halogen, —CN, C$_{1-4}$ alkyl, —(C$_{1-4}$ alkyl)-R$^6$, a C$_{7-12}$ aralkyl, C$_{3-8}$ cycloalkyl ring, C$_{1-4}$ cyanoalkyl, —OR$^6$, —SR$^6$, —OCOR$^6$, —COR$^6$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl, each said C$_{1-4}$ alkyl chain and each said C$_{3-8}$ cycloalkyl group is optionally and independently substituted with up to 3 instances of halogen;

each $R^{5c}$ is independently selected from halogen, —CN, C$_{1-4}$ alkyl, —(C$_{1-4}$ alkyl)-R$^6$, a C$_{7-12}$ aralkyl, C$_{3-8}$ cycloalkyl ring, C$_{1-4}$ cyanoalkyl, —OR$^6$, —SR$^6$, —OCOR$^6$, —COR$^6$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl, each said C$_{1-4}$ alkyl chain and each said C$_{3-8}$ cycloalkyl group is optionally and independently substituted with up to 3 instances of halogen;

each $R^{5d}$ is independently selected from halogen, —CN, C$_{1-4}$ alkyl, —(C$_{1-4}$ alkyl)-R$^6$, a C$_{7-12}$ aralkyl, C$_{3-8}$ cycloalkyl ring, C$_{1-4}$ cyanoalkyl, —OR$^6$, —SR$^6$, —OCOR$^6$, —COR$^6$, —C(O)OR$^6$, —C(O)N(R$^6$)$_2$, —N(R$^6$)C(O)R$^6$, —N(R$^6$)$_2$, —SO$_2$R$^6$, —SO$_2$N(R$^6$)$_2$, —N(R$^6$)SO$_2$R$^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl, each said C$_{1-4}$ alkyl chain and each said C$_{3-8}$ cycloalkyl group is optionally and independently substituted with up to 3 instances of halogen;

each R$^6$ is independently selected from hydrogen, a C$_{1-4}$ alkyl, a C$_{2-4}$ alkenyl, phenyl, a C$_{7-12}$ aralkyl or a C$_{3-8}$ cycloalkyl ring; wherein each said C$_{1-4}$ alkyl, each said C$_{2-4}$ alkenyl, each said phenyl, each said C$_{7-12}$ aralkyl and each said cycloalkyl group is optionally and independently substituted with up to 3 instances of halogen;

alternatively, two instances of R$^6$ linked to the same nitrogen atom of $R^5$, $R^{5a}$, $R^{5b}$, $R^{5c}$ or $R^{5d}$ together with said nitrogen atom of $R^5$, $R^{5a}$, $R^{5b}$, $R^{5c}$ or $R^{5d}$, respectively, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; or alternatively, one instance of R$^6$ linked to a nitrogen atom of $R^5$, $R^{5a}$, $R^{5b}$, $R^{5c}$ or $R^{5d}$ and one instance of R$^6$ linked to a carbon or sulfur atom of the same $R^5$, $R^{5a}$, $R^{5b}$, $R^{5c}$ or $R^{5d}$, respectively, together with said nitrogen and said carbon or sulfur atom of the same $R^5$, $R^{5a}$, $R^{5b}$, $R^{5c}$ or $R^{5d}$, respectively, may form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

alternatively, two $J^D$ groups attached to two vicinal ring D atoms, taken together with said two vicinal ring D atoms, form a 5 to 7-membered heterocycle or a 5-membered heteroaryl ring that is fused to ring D; wherein said 5 to 7-membered heterocycle or said 5-membered ring heteroaryl contains from 1 to 3 heteroatoms independently selected from N, O or S; and wherein said 5 to 7-membered heterocycle or said 5-membered heteroaryl ring is optionally and independently substituted by up to 3 instances of oxo or —(Y)—R$^9$;

wherein Y is either absent or is a linkage in the form of a $C_{1-6}$ alkyl chain, optionally substituted by up to 6 instances of fluoro;

each R$^9$ is independently selected from hydrogen, —CN, —OR$^{10}$, —COR$^{10}$, —OC(O)R$^{10}$, —C(O)OR$^{10}$, —C(O)N(R$^{10}$)$_2$, —C(O)N(R$^{10}$)SO$_2$R$^{10}$, —N(R$^{10}$)C(O)R$^{10}$, —N(R$^{10}$)C(O)OR$^{10}$, —N(R$^{10}$)C(O)N(R$^{10}$)$_2$, —N(R$^{10}$)$_2$, —SO$_2$R$^{10}$, —SO$_2$N(R$^{10}$)$_2$, —SO$_2$N(R$^{10}$)COOR$^{10}$, —SO$_2$N(R$^{10}$)C(O)R$^{10}$, —N(R$^{10}$)SO$_2$R$^{10}$, a $C_{3-6}$ cycloalkyl ring, a 4-8-membered heterocyclic ring, a phenyl ring or a 5-6 membered heteroaroaryl ring; wherein each said 4 to 8-membered heterocyclic ring or 5 to 6-membered heteroaryl ring contains up to 4 ring heteroatoms independently selected from N, O or S; and wherein each of said $C_{3-6}$ cycloalkyl rings, each of said 4 to 8-membered heterocyclic rings, each of said phenyl and each of said 5 to 6-membered heteroaryl rings is optionally substituted with up to 3 instances of R$^{11a}$;

wherein each R$^{10}$ is independently selected from hydrogen, a $C_{1-6}$ alkyl, phenyl, benzyl, a $C_{3-6}$ cycloalkyl ring, a 4 to 7-membered heterocyclic ring or a 5 or 6-membered heteroaryl ring, wherein each 5 or 6-membered heteroaryl ring or 4 to 7-membered heterocyclic ring contains up to 4 ring heteroatoms independently selected from N, O and S; and wherein each of said $C_{1-6}$ alkyl, each said phenyl, each said benzyl, each said $C_{3-8}$ cycloalkyl group, each said 4 to 7-membered heterocyclic ring and each 5 or 6-membered heteroaryl ring is optionally and independently substituted with up to 3 instances of R$^{11b}$;

each R$^{11a}$ is independently selected from halogen, $C_{1-6}$ alkyl, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ or —N(R$^{12}$)SO$_2$R$^{12}$; wherein each of said $C_{1-6}$ alkyl is optionally and independently substituted by up to 6 instances of fluoro, and/or 3 instances of R$^{12}$;

each R$^{11b}$ is independently selected from halogen, $C_{1-6}$ alkyl, —CN, —OR$^{12}$, —COR$^{12}$, —C(O)OR$^{12}$, —C(O)N(R$^{12}$)$_2$, —N(R$^{12}$)C(O)R$^{12}$, —N(R$^{12}$)C(O)OR$^{12}$, —N(R$^{12}$)C(O)N(R$^{12}$)$_2$, —N(R$^{12}$)$_2$, —SO$_2$R$^{12}$, —SO$_2$N(R$^{12}$)$_2$ or —N(R$^{12}$)SO$_2$R$^{12}$; wherein each of said $C_{1-6}$ alkyl is optionally and independently substituted by up to 6 instances of fluoro and/or 3 instances of R$^{12}$;

each R$^{12}$ is selected from $C_{1-4}$ alkyl, $C_{1-4}$ (fluoroalkyl), —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ fluoroalkyl) or oxo;

R$^C$ is either
i) a ring C; or
ii) R$^C$ is selected from halogen, —CN, $C_{1-6}$ alkyl, —($C_{1-6}$ alkyl)-R$^N$, —OR$^K$, —COR$^K$, —OC(O)R$^K$, —C(O)OR$^K$, —C(O)N(R$^K$)$_2$, —N(R$^k$)C(O)R$^K$, —N(R$^k$)C(O)OR$^K$, —N(R$^k$)C(O)N(R$^K$)$_2$, —N(R$^K$)$_2$, —SO$_2$R$^K$, —SO$_2$N(R$^K$)$_2$ or —N(R$^k$)SO$_2$R$^K$; wherein said R$^C$ that is a $C_{1-6}$ alkyl is optionally and independently substituted with up to 6 instances of fluoro and/or up to 3 instances of R$^{7c}$];

each R$^k$ is independently selected from hydrogen or a $C_{1-6}$ alkyl;

each R$^K$ is independently selected from hydrogen, a $C_{1-6}$ alkyl, a phenyl ring, a monocyclic 5 or 6-membered heteroaryl ring, a monocyclic $C_{3-6}$ cycloaliphatic ring, or a monocyclic 4 to 6-membered heterocycle; wherein said monocyclic 5 or 6-membered heteroaryl ring or said monocyclic 4 to 6-membered heterocycle contain between 1 and 4 heteroatoms selected from N, O or S; wherein said monocyclic 5 or 6-membered heteroaryl ring is not a 1,3,5-triazinyl ring; and wherein said phenyl, said monocyclic 5 to 6-membered heteroaryl ring, said monocyclic $C_{3-6}$ cycloaliphatic ring, or said monocyclic 4 to 6-membered heterocycle is optionally and independently substituted with up to 6 instances of fluoro and/or up to 3 instances of J$^M$; and wherein each R$^K$ that is a $C_{1-6}$ alkyl is optionally and independently substituted by up to 3 instances of R$^{7d}$;

each R$^N$ is independently selected from a phenyl ring, a monocyclic 5 or 6-membered heteroaryl ring, a monocyclic $C_{3-6}$ cycloaliphatic ring, or a monocyclic 4 to 6-membered heterocycle; wherein said monocyclic 5 or 6-membered heteroaryl ring or said monocyclic 4 to 6-membered heterocycle contain between 1 and 4 heteroatoms selected from N, O or S; wherein said monocyclic 5 or 6-membered heteroaryl ring is not a 1,3,5-triazinyl ring; and wherein said phenyl, said monocyclic 5 to 6-membered heteroaryl ring, said monocyclic $C_{3-6}$ cycloaliphatic ring, or said monocyclic 4 to 6-membered heterocycle is optionally and independently substituted with up to 6 instances of fluoro and/or up to 3 instances of J$^M$;

each J$^M$ is independently selected from —CN, a $C_{1-6}$ aliphatic, —OR$^M$, —SR$^M$, —N(R$^M$)$_2$, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of R$^{7c}$;

each R$^M$ is independently selected from hydrogen, a $C_{1-6}$ aliphatic, a $C_{3-8}$ cycloaliphatic ring or a 4 to 8-membered heterocyclic ring; wherein each said 4 to 8-membered heterocyclic ring contains between 1 and 3 heteroatoms independently selected from O, N or S; and wherein each said $C_{1-6}$ aliphatic, each said $C_{3-8}$ cycloaliphatic ring and each said 4 to 8-membered heterocyclic ring, is optionally and independently substituted with up to 3 instances of R$^{7e}$;

ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6-membered heteroaryl ring is not a 1,3,5-triazinyl ring; and wherein said phenyl, monocyclic 5 to 6-membered heteroaryl ring, bicyclic 8 to 10-membered heteroaryl ring, monocyclic 3 to 10-membered cycloaliphatic ring, or monocyclic 4 to 10-membered heterocycle is optionally and independently substituted with up to 3 instances of J$^C$;

each J$^C$ is independently selected from halogen, —CN, —NO$_2$, a $C_{1-6}$ aliphatic, —OR$^H$, —SR$^H$, —N(R$^H$)$_2$, a $C_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said $C_{1-6}$ aliphatic, each said $C_{3-8}$ cycloaliphatic ring and each said 4 to 8-membered heterocyclic ring, is optionally and independently substituted with up to 3 instances of $R^7$; or alternatively, two $J^C$ groups attached to two vicinal ring C atoms, taken together with said two vicinal ring C atoms, form a 5 to 7-membered heterocycle that is a new ring fused to ring C;

wherein said 5 to 7-membered heterocycle contains from 1 to 2 heteroatoms independently selected from N, O or S;

each $R^H$ is independently selected from hydrogen, a $C_{1-6}$ aliphatic, a $C_{3-8}$ cycloaliphatic ring or a 4 to 8-membered heterocyclic ring; wherein each said 4 to 8-membered heterocylic ring contains between 1 and 3 heteroatoms independently selected from O, N or S; and wherein each said $C_{1-6}$ aliphatic, each said $C_{3-8}$ cycloaliphatic ring and each said 4 to 8-membered heterocyclic ring, is optionally and independently substituted with up to 3 instances of $R^{7a}$;

alternatively, two instances of $R^H$ linked to the same nitrogen atom of $-N(R^H)_2$, together with said nitrogen atom of $-N(R^H)_2$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^{7b}$;

each $R^7$ is independently selected from halogen, —CN, —NO$_2$, $C_{1-4}$ alkyl, $C_{1-4}$ haloalkyl, $C_{3-8}$ cycloalkyl ring, $C_{3-8}$ (halocycloalkyl) ring, —OR$^8$, —SR$^8$, —N(R$^8$)$_2$, or an oxo group;

each $R^{7a}$ is independently selected from halogen, —CN, —NO$_2$, $C_{1-4}$ alkyl, $C_{1-4}$ haloalkyl, $C_{3-8}$ cycloalkyl ring, $C_{3-8}$ (halocycloalkyl) ring, —OR$^8$, —SR$^8$, —N(R$^8$)$_2$, or an oxo group;

each $R^{7b}$ is independently selected from halogen, —CN, —NO$_2$, $C_{1-4}$ alkyl, $C_{1-4}$ haloalkyl, $C_{3-8}$ cycloalkyl ring, $C_{3-8}$ (halocycloalkyl) ring, —OR$^8$, —SR$^8$, —N(R$^8$)$_2$, or an oxo group;

each $R^{7c}$ is independently selected from hydrogen, halogen, —CN, —NO$_2$, $C_{1-4}$ alkyl, $C_{1-4}$ haloalkyl, $C_{3-8}$ cycloalkyl ring, —OR$^8$, —SR$^8$, —N(R$^8$)$_2$, or an oxo group; wherein each said cycloalkyl group is optionally and independently substituted with up to 3 instances of halogen;

each $R^{7d}$ is independently selected from hydrogen, halogen, —CN, —NO$_2$, $C_{1-4}$ alkyl, $C_{1-4}$ haloalkyl, $C_{3-8}$ cycloalkyl ring, —OR$^8$, —SR$^8$, —N(R$^8$)$_2$, or an oxo group; wherein each said cycloalkyl group is optionally and independently substituted with up to 3 instances of halogen;

each $R^{7e}$ is independently selected from hydrogen, halogen, —CN, —NO$_2$, $C_{1-4}$ alkyl, $C_{1-4}$ haloalkyl, $C_{3-8}$ cycloalkyl ring, —OR$^8$, —SR$^8$, —N(R$^8$)$_2$, or an oxo group; wherein each said cycloalkyl group is optionally and independently substituted with up to 3 instances of halogen;

each $R^8$ is independently selected from hydrogen, a $C_{1-4}$ alkyl, $C_{1-4}$ haloalkyl or a $C_{3-8}$ cycloalkyl ring, $C_{3-8}$ (halocycloalkyl) ring alternatively, two instances of $R^8$ linked to the same nitrogen atom of $R^7$, $R^{7a}$, $R^{7b}$, $R^{7c}$, $R^{7d}$ or $R^{7e}$, together with said nitrogen atom of $R^7$, $R^{7a}$, $R^{7b}$, $R^{7c}$, $R^{7d}$ or $R^{7e}$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; and $R^A$ is selected from hydrogen, halogen, $C_{1-4}$ alkyl or $C_{1-4}$ haloalkyl.

In the compounds of Formula I:

ring B is a phenyl or a 5 or 6-membered heteroaryl ring, containing 1 or 2 ring heteroatoms selected from N, O or S;

n is an integer selected from 0 to 3;

each $J^B$ is independently selected from halogen, —CN, a $C_{1-6}$ aliphatic, —OR$^B$ or a $C_{3-8}$ cycloaliphatic group; wherein each said $C_{1-6}$ aliphatic and each said $C_{3-8}$ cycloaliphatic group is optionally and independently substituted with up to 3 instances of $R^3$;

each $R^B$ is independently selected from hydrogen, a $C_{1-6}$ aliphatic or a $C_{3-8}$ cycloaliphatic; wherein each said $C_{1-6}$ aliphatic and each said $C_{3-8}$ cycloaliphatic ring is optionally and independently substituted with up to 3 instances of $R^{3a}$;

each $R^3$ is independently selected from halogen, —CN, $C_{1-4}$ alkyl, $C_{1-4}$ haloalkyl, —O($C_{1-4}$ alkyl) or —O($C_{1-4}$ haloalkyl);

each $R^{3a}$ is independently selected from halogen, —CN, $C_{1-4}$ alkyl, $C_{1-4}$ haloalkyl, —O($C_{1-4}$ alkyl) or —O($C_{1-4}$ haloalkyl);

o is an integer selected from 0 to 3;

each $J^D$ is independently selected from halogen, —NO$_2$, —OR$^D$, —SR$^D$, —C(O)R$^D$, —C(O)OR$^D$, —C(O)N(R$^D$)$_2$, —CN, —N(R$^D$)$_2$, —N(R$^d$)C(O)R$^D$, —N(R$^d$)C(O)OR$^D$, —SO$_2$R$^D$, —SO$_2$N(R$^D$)$_2$, —N(R$^d$)SO$_2$R$^D$, a $C_{1-6}$ aliphatic, —($C_{1-6}$ aliphatic)-R$^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocyclic ring and each said 5 to 10-membered heteroaryl ring contains between 1 and 3 heteroatoms independently selected from O, N or S; and wherein each said $C_{1-6}$ aliphatic, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 3 instances of $R^5$;

each $R^D$ is independently selected from hydrogen, a $C_{1-6}$ aliphatic, —($C_{1-6}$ aliphatic)-R$^f$, a $C_{3-8}$ cycloaliphatic ring, a 4 to 8-membered heterocyclic ring, phenyl or a 5 to 6-membered heteroaryl ring; wherein each said 4 to 8-membered heterocylic ring and each said 5 to 6-membered heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted with up to 3 instances of $R^{5a}$;

each $R^d$ is independently selected from hydrogen, a $C_{1-6}$ aliphatic, —($C_{1-6}$ aliphatic)-R$^f$, a $C_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^{5b}$;

each $R^f$ is independently selected from a $C_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^{5c}$;

when $J^D$ is —C(O)N($R^D$)$_2$, —N($R^D$)$_2$ or —SO$_2$N($R^D$)$_2$, the two $R^D$ groups together with the nitrogen atom attached to the $R^D$ groups alternatively form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;

when $J^D$ is —N($R^d$)C(O)$R^D$, the $R^D$ group together with the carbon atom attached to the $R^D$ group, with the nitrogen atom attached to the $R^d$ group, and with the $R^d$ group alternatively form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;

when $J^D$ is —N($R^d$)C(O)O$R^D$, the $R^D$ group together with the oxygen atom attached to the $R^D$ group, with the carbon atom of the —C(O)— portion of the —N($R^d$)C(O)O$R^D$ group, with the nitrogen atom attached to the $R^d$ group, and with the $R^d$ group alternatively form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;

when $J^D$ is —N($R^d$)SO$_2$$R^D$, the $R^D$ group together with the oxygen atom attached to the $R^D$ group, with the sulfur atom attached to said oxygen atom in the —SO$_2$$R^D$ portion of the —N($R^d$)SO$_2$$R^D$ group, with the nitrogen atom attached to the $R^d$ group, and with the $R^d$ group alternatively form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;

each $R^5$ is independently selected from halogen, —CN, —NO$_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, —O$R^6$, —S$R^6$, —OCO$R^6$, —CO$R^6$, —C(O)O$R^6$, —C(O)N($R^6$)$_2$, —N($R^6$)C(O)$R^6$, —N($R^6$)$_2$, —SO$_2$$R^6$, —SO$_2$N($R^6$)$_2$, —N($R^6$)SO$_2$$R^6$, phenyl or an oxo group; wherein each said phenyl group is optionally and independently substituted with up to 3 instances of halogen, —OH, —NH$_2$, —NH($C_{1-4}$ alkyl), —N($C_{1-4}$ alkyl)$_2$, —NO$_2$, —CN, $C_{1-4}$ alkyl, $C_{1-4}$ haloalkyl, —O($C_{1-4}$ alkyl) or —O($C_{1-4}$ haloalkyl); and wherein each said $C_{7-12}$ aralkyl and each said cycloalkyl group is optionally and independently substituted with up to 3 instances of halogen;

each $R^{5a}$ is independently selected from halogen, —CN, —NO$_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, —O$R^6$, —S$R^6$, —OCO$R^6$, —CO$R^6$, —C(O)O$R^6$, —C(O)N($R^6$)$_2$, —N($R^6$)C(O)$R^6$, —N($R^6$)$_2$, —SO$_2$$R^6$, —SO$_2$N($R^6$)$_2$, —N($R^6$)SO$_2$$R^6$, phenyl or an oxo group; wherein each said phenyl group is optionally and independently substituted with up to 3 instances of halogen, —OH, —NH$_2$, —NH($C_{1-4}$ alkyl), —N($C_{1-4}$ alkyl)$_2$, —NO$_2$, —CN, $C_{1-4}$ alkyl, $C_{1-4}$ haloalkyl, —O($C_{1-4}$ alkyl) or —O($C_{1-4}$ haloalkyl); and wherein each said $C_{7-12}$ aralkyl and each said cycloalkyl group is optionally and independently substituted with up to 3 instances of halogen;

each $R^{5b}$ is independently selected from halogen, —CN, —NO$_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, —O$R^6$, —S$R^6$, —OCO$R^6$, —CO$R^6$, —C(O)O$R^6$, —C(O)N($R^6$)$_2$, —N($R^6$)C(O)$R^6$, —N($R^6$)$_2$, —SO$_2$$R^6$, —SO$_2$N($R^6$)$_2$, —N($R^6$)SO$_2$$R^6$, phenyl or an oxo group; wherein each said phenyl group is optionally and independently substituted with up to 3 instances of halogen, —OH, —NH$_2$, —NH($C_{1-4}$ alkyl), —N($C_{1-4}$ alkyl)$_2$, —NO$_2$, —CN, $C_{1-4}$ alkyl, $C_{1-4}$ haloalkyl, —O($C_{1-4}$ alkyl) or —O($C_{1-4}$ haloalkyl); and wherein each said $C_{7-12}$ aralkyl and each said cycloalkyl group is optionally and independently substituted with up to 3 instances of halogen;

each $R^{5c}$ is independently selected from halogen, —CN, —NO$_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, —O$R^6$, —S$R^6$, —OCO$R^6$, —CO$R^6$, —C(O)O$R^6$, —C(O)N($R^6$)$_2$, —N($R^6$)C(O)$R^6$, —N($R^6$)$_2$, —SO$_2$$R^6$, —SO$_2$N($R^6$)$_2$, —N($R^6$)SO$_2$$R^6$, phenyl or an oxo group; wherein each said phenyl group is optionally and independently substituted with up to 3 instances of halogen, —OH, —NH$_2$, —NH($C_{1-4}$ alkyl), —N($C_{1-4}$ alkyl)$_2$, —NO$_2$, —CN, $C_{1-4}$ alkyl, $C_{1-4}$ haloalkyl, —O($C_{1-4}$ alkyl) or —O($C_{1-4}$ haloalkyl); and wherein each said $C_{7-12}$ aralkyl and each said cycloalkyl group is optionally and independently substituted with up to 3 instances of halogen;

each $R^6$ is independently selected from hydrogen, a $C_{1-4}$ alkyl, a $C_{2-4}$ alkenyl, phenyl, a $C_{7-12}$ aralkyl or a $C_{3-8}$ cycloalkyl ring; wherein each said $C_{1-4}$ alkyl, each said $C_{2-4}$ alkenyl, each said phenyl, each said $C_{7-12}$ aralkyl and each said cycloalkyl group is optionally and independently substituted with up to 3 instances of halogen;

alternatively, two instances of $R^6$ linked to the same nitrogen atom of $R^5$, together with said nitrogen atom of $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; or alternatively, one instance of $R^6$ linked to a nitrogen atom of $R^5$ and one instance of $R^6$ linked to a carbon or sulfur atom of the same $R^5$, together with said nitrogen and said carbon or sulfur atom of the same $R^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

or, alternatively, two $J^D$ groups attached to two vicinal ring D atoms, taken together with said two vicinal ring D atoms, form a 5 to 7-membered heterocycle resulting in a fused ring D wherein said 5 to 7-membered heterocycle contains from 1 to 3 heteroatoms independently selected from N, O or S; and wherein said 5 to 7-membered heterocycle is optionally and independently substituted by up to 3 instances of halogen, —OH, —NH$_2$, —NH($C_{1-4}$ alkyl), —N($C_{1-4}$ alkyl)$_2$, —CN, $C_{1-4}$ alkyl, $C_{1-4}$ haloalkyl, —O($C_{1-4}$ alkyl), —O($C_{1-4}$ haloalkyl), oxo or phenyl; wherein said phenyl is optionally and independently substituted by up to three instances of halogen, —OH, —NH$_2$, —NH($C_{1-4}$ alkyl), —N($C_{1-4}$ alkyl)$_2$, —NO$_2$, —CN, $C_{1-4}$ alkyl, $C_{1-4}$ haloalkyl, —O($C_{1-4}$ alkyl) or —O($C_{1-4}$ haloalkyl);

$R^C$ is a ring C; ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle;

wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6-membered heteroaryl ring is not a 1,3, 5-triazinyl ring; and wherein said phenyl, monocyclic 5 to 6-membered heteroaryl ring, bicyclic 8 to 10-membered heteroaryl ring, monocyclic 3 to 10-membered cycloaliphatic ring, or monocyclic 4 to 10-membered heterocycle is optionally and independently substituted with up to 3 instances of $J^C$;

each $J^C$ is independently selected from halogen, —CN, —NO$_2$, a C$_{1-6}$ aliphatic, —OR$^H$, —SR$^H$, —N(R$^H$)$_2$, a C$_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said C$_{1-6}$ aliphatic, each said C$_{3-8}$ cycloaliphatic ring and each said 4 to 8-membered heterocyclic ring, is optionally and independently substituted with up to 3 instances of R$^7$; or alternatively, two $J^C$ groups attached to two vicinal ring C atoms, taken together with said two vicinal ring C atoms, form a 5 to 7-membered heterocycle resulting in a fused ring C; wherein said 5 to 7-membered heterocycle contains from 1 to 2 heteroatoms independently selected from N, O or S;

each R$^H$ is independently selected from hydrogen, a C$_{1-6}$ aliphatic, a C$_{3-8}$ cycloaliphatic ring or a 4 to 8-membered heterocyclic ring; wherein each said 4 to 8-membered heterocylic ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, is optionally and independently substituted with up to 3 instances of R$^{7a}$;

alternatively, two instances of R$^H$ linked to the same nitrogen atom of $J^C$, together with said nitrogen atom of $J^C$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of R$^{7b}$;

each R$^7$ is independently selected from halogen, —CN, —NO$_2$, C$_{1-4}$ alkyl, C$_{1-4}$ haloalkyl, C$_{3-8}$ cycloalkyl ring, —OR, —SR$^8$, —N(R$^8$)$_2$, or an oxo group; wherein each said cycloalkyl group is optionally and independently substituted with up to 3 instances of halogen;

each R$^{7a}$ is independently selected from halogen, —CN, —NO$_2$, C$_{1-4}$ alkyl, C$_{1-4}$ haloalkyl, C$_{3-8}$ cycloalkyl ring, —OR, —SR$^8$, —N(R$^8$)$_2$, or an oxo group; wherein each said cycloalkyl group is optionally and independently substituted with up to 3 instances of halogen;

each R$^{7b}$ is independently selected from halogen, —CN, —NO$_2$, C$_{1-4}$ alkyl, C$_{1-4}$ haloalkyl, C$_{3-8}$ cycloalkyl ring, —OR, —SR$^8$, —N(R$^8$)$_2$, or an oxo group; wherein each said cycloalkyl group is optionally and independently substituted with up to 3 instances of halogen;

each R$^8$ is independently selected from hydrogen, a C$_{1-4}$ alkyl, C$_{1-4}$ haloalkyl or a C$_{3-8}$ cycloalkyl ring; wherein each said cycloalkyl group is optionally and independently substituted with up to 3 instances of halogen;

alternatively, two instances of R$^8$ linked to the same nitrogen atom of R$^7$, R$^{7a}$ or R$^{7b}$, together with said nitrogen atom of R$^7$, R$^{7a}$ or R$^{7b}$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; and R$^A$ is selected from hydrogen, halogen, C$_{1-4}$ alkyl or C$_{1-4}$ haloalkyl.

In some of the embodiments of the compounds of Formula Ib, or pharmaceutically acceptable salts thereof, ring B is absent. In some of the embodiments, R$^A$ is hydrogen.

In some of the embodiments of the compounds of Formula Ib, or pharmaceutically acceptable salts thereof, the compounds are represented by Formula IIb:

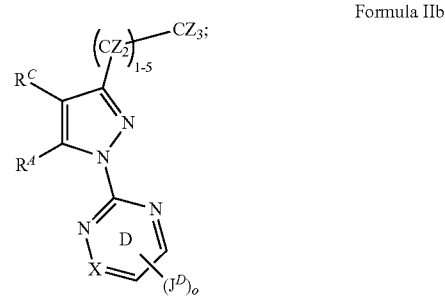

Formula IIb wherein each instance of Z is independently selected from fluorine or hydrogen; the (CZ$_2$)$_{1-5}$ group is linked to the 3-position of the pyrazolyl group via a terminal carbon atom with a single bond; each of the CZ$_2$ in the (CZ$_2$)$_{1-5}$ group is linked to the adjacent CZ$_2$ or CZ$_3$ groups via a single bond attached to the adjacent carbon atoms; and the CZ$_3$ group is linked to the adjacent CZ$_2$ group via a single bond attached to the adjacent carbon atoms.

In some of the embodiments of the compounds of Formula IIb, or pharmaceutically acceptable salts thereof, up to 5 instances of Z are fluorine and the remaining instances of Z are hydrogen. In some of these embodiments, R$^A$ is hydrogen.

In some of the embodiments of the compounds of Formula Ib or IIb, or pharmaceutically acceptable salts thereof, R$^C$ is not a ring. In some of these embodiments, or pharmaceutically acceptable salts thereof, R$^C$ can be selected from halogen, —CN, C$_{1-6}$ alkyl, —(C$_{1-6}$ alkyl)-R$^N$, —OR$^K$, —COR$^K$, —C(O)OR$^K$, —C(O)N(R$^K$)$_2$, —N(R$^k$)C(O)R$^K$, —N(R$^k$)C(O)OR$^K$, —N(R$^k$)C(O)N(R$^K$)$_2$, —N(R$^K$)$_2$, —SO$_2$R$^K$, —SO$_2$N(R$^K$)$_2$, or —N(R$^k$)SO$_2$R$^K$; wherein when said R$^C$ is a C$_{1-6}$ alkyl, the C$_{1-6}$ alkyl is optionally and independently substituted with up to 6 instances of fluoro and/or up to 2 instances of R$^{7c}$. In some of these embodiments, or pharmaceutically acceptable salts thereof, R$^C$ can be —CN, C$_{1-6}$ alkyl, —COR$^K$, —C(O)OR$^K$, —C(O)N(R$^K$)$_2$, —N(R$^K$)$_2$, —SO$_2$R$^{7K}$, or —SO$_2$N(R$^K$)$_2$; wherein when said R$^C$ is a C$_{1-6}$ alkyl, the C$_{1-6}$ alkyl is optionally and independently substituted with up to 6 instances of fluoro and/or up to 2 instances of R$^{7c}$. In some of these embodiments, or pharmaceutically acceptable salts thereof, R$^C$ can be —COR$^K$, —C(O)OR$^K$, —C(O)N(R$^K$)$_2$, —N(R$^K$)$_2$, —SO$_2$R$^K$ or —SO$_2$N(R$^K$)$_2$.

In some of the embodiments of the compounds of Formula Ib or IIb, or pharmaceutically acceptable salts thereof, R$^C$ is ring C. In some of these compounds, or the pharmaceutically acceptable salts thereof, ring C is a phenyl, a monocyclic 5 or 6-membered heteroaryl ring, a monocyclic C$_{3-6}$ cycloaliphatic ring or a monocyclic 4 to 6-membered heterocycle; each of the phenyl, monocyclic 5 or 6-membered heteroaryl ring, monocyclic C$_{3-6}$ cycloaliphatic ring or monocyclic 4 to 6-membered heterocycle is optionally and independently substituted with up to 3 instances of $J^C$. Ring C can also be a 5 or 6-membered heteroaryl ring, optionally substituted with up to 2 instances of $J^C$, or ring C can be unsubstituted. For instance, Ring C can be thienyl, thiazolyl, oxadiazolyl, oxazolyl, isoxazolyl, tetrazolyl, pyrrolyl, triazolyl, furanyl, pyridinyl, pyrimidinyl, pyrazinyl or pyridazinyl, which can be unsubstituted or substituted. Ring C can also be unsubstituted or substituted oxazolyl or unsubstituted isoxazolyl.

In some of the embodiments of the compounds of Formula Ib or IIb, or pharmaceutically acceptable salts thereof, the compounds are represented by Formula IIIb:

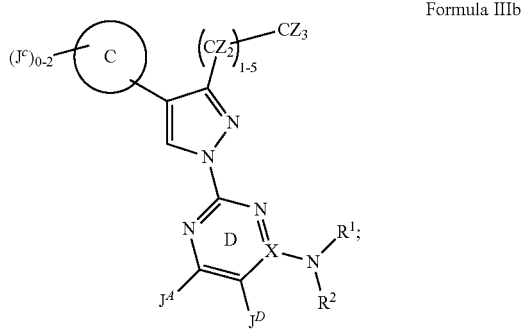

Formula IIIb wherein each instance of Z is independently selected from fluorine or hydrogen; the $(CZ_2)_{1-5}$ group is linked to the 3-position of the pyrazolyl group via a terminal carbon atom with a single bond; each of the $CZ_2$ in the $(CZ_2)_{1-5}$ group is linked to the adjacent $CZ_2$ or $CZ_3$ groups via a single bond attached to the carbon atom; and the $CZ_3$ group is linked to the adjacent $CZ_2$ via a single bond attached to the carbon atom;

the circle with a letter C in the middle represents ring C;

when X is N, the moiety $—N(R^1)(R^2)$ is absent, when X is C, the moiety $—N(R^1)(R^2)$ is present, $J^A$ is selected from hydrogen, halogen, methyl, methoxy, trifluoromethyl, trifluoromethoxy or $—NR^aR^b$, wherein $R^a$ and $R^b$ are each independently selected from hydrogen, $C_{1-6}$ alkyl or a 3-6 cycloalkyl ring; or wherein $R^a$ and $R^b$ together with the N atom to which they are attached form a 4 to 6-membered heterocyclic ring;

$J^D$ is selected from hydrogen, halogen, —CN, —CF$_3$, methoxy, trifluoromethoxy or methyl;

$R^1$ and $R^2$, together with the nitrogen atom to which they are attached, form a 4 to 8-membered heterocyclic ring or 5 or 6-membered heteroaryl ring; wherein said 4 to 8-membered heterocyclic ring or 5 or 6-membered heteroaryl ring optionally contains in addition to the nitrogen atom up to 3 ring heteroatoms independently selected from N, O or S, and is optionally substituted by up to 5 instances of $R^{5e}$; or alternatively, $R^1$ and $R^2$ are each independently selected from hydrogen, $C_{1-6}$ alkyl, a $C_{3-8}$ cycloalkyl ring, a 4 to 8-membered heterocyclic ring, a 5 or 6-membered heteroaryl or a $C_{1-6}$ alkyl-$R^Y$; wherein each of said 4 to 8-membered heterocyclic ring and each of said 5 or 6-membered heteroaryl ring contains up to 3 ring heteroatoms independently selected from N, O and S; and wherein each of said $C_{1-6}$ alkyl, $C_{3-8}$ cycloalkyl ring, 4 to 8-membered heterocyclic ring group, 5 or 6-membered heteroaryl and $C_{1-6}$ alkyl-$R^Y$ is optionally and independently substituted with up to 5 instances of $R^{5f}$; provided that $R^1$ and $R^2$ are never simultaneously hydrogen; or alternatively, when $R^1$ and $R^2$ attached to the nitrogen atom form the 4 to 8-membered heterocyclic ring or 5 or 6-membered heteroaryl ring substituted with up to 5 instances of $R^{5e}$, two of the instances of $R^{5e}$ attached to the same or different atoms of said ring, together with said atom or atoms, optionally form a $C_{3-8}$ cycloalkyl ring, a 4 to 6-membered heterocyclic ring; a phenyl or a 5 or 6-membered heteroaryl ring, resulting in a bicyclic system wherein the two rings of the bicyclic system are in a spiro, fused or bridged relationship, wherein said 4 to 6-membered heterocycle or said 5 or 6-membered heteroaryl ring contains up to three ring heteroatoms independently selected from N, O or S; and wherein said $C_{3-8}$ cycloalkyl ring, 4 to 6-membered heterocyclic ring, phenyl or 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR(CO)CO($C_{1-4}$ alkyl), —OH or halogen; wherein R is hydrogen or a $C_{1-2}$ alkyl;

$R^Y$ is selected from a $C_{3-8}$ cycloalkyl ring, a 4 to 8-membered heterocyclic ring, phenyl, or a 5 to 6-membered heteroaromatic ring; wherein each of said 4 to 8-membered heterocyclic ring or 5 to 6-membered heteroaromatic ring contains up to 4 ring heteroatoms independently selected from N, O or S; and wherein each of said $C_{3-8}$ cycloalkyl ring, each of said 4 to 8-membered heterocyclic ring, each of said phenyl, and each of said 5 to 6-membered heteroaromatic ring is optionally substituted with up to 5 instances of $R^{5g}$; or alternatively, when one of $R^1$ or $R^2$ is the $C_{3-8}$ cycloalkyl ring, 4 to 8-membered heterocyclic ring or 5 or 6-membered heteroaryl substituted with up to 5 instances of $R^{5f}$, two of the instances of $R^{5f}$ attached to the same or different ring atoms of said $R^1$ or $R^2$, together with said atom or atoms, form a $C_{3-8}$ cycloalkyl ring, a 4 to 6-membered heterocyclic ring, a phenyl or a 5 or 6-membered heterocyclic ring, resulting in a bicyclic system wherein the two rings are in a spiro, fused or bridged relationship, wherein said 4 to 6-membered heterocycle or said 5 or 6-membered heterocyclic ring contains up to two ring heteroatoms independently selected from N, O or S; and wherein said $C_{3-8}$ cycloalkyl ring, 4 to 6-membered heterocyclic ring, phenyl or 5 or 6-membered heterocyclic ring is optionally substituted by up to 2 instances of $C_{1-4}$ alkyl, $C_{1-4}$ haloalkyl, oxo, —(CO)CO($C_{1-4}$ alkyl), —NR'(CO)CO($C_{1-4}$ alkyl) or halogen; wherein R' is hydrogen or a $C_{1-2}$ alkyl;

each $R^{5e}$ is independently selected from halogen, —CN, $C_{1-6}$ alkyl, —OR$^{6a}$, —SR$^{6a}$, —COR$^{6a}$, —OC(O)R$^{6a}$, —C(O)OR$^{6a}$, —C(O)N(R$^{6a}$)$_2$, —C(O)N(R$^{6a}$)SO$_2$R$^{6a}$, —N(R$^{6a}$)C(O)R$^{6a}$, —N(R$^{6a}$)C(O)OR$^{6a}$, —N(R$^{6a}$)C(O)N(R$^{6a}$)$_2$, —N(R$^{6a}$)$_2$, —SO$_2$R$^{6a}$, —SO$_2$N(R$^{6a}$)$_2$, —SO$_2$N(R$^{6a}$)COOR$^{6a}$, —SO$_2$N(R$^{6a}$)C(O)R$^{6a}$, —N(R$^{6a}$)SO$_2$R$^{6a}$, a $C_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^{5f}$ is independently selected from halogen, —CN, $C_{1-6}$ alkyl, —OR$^{6a}$, —SR$^{6a}$, —COR$^{6a}$, —OC(O)R$^{6a}$, —C(O)OR$^{6a}$, —C(O)N(R$^{6a}$)$_2$, —C(O)N(R$^{6a}$)SO$_2$R$^{6a}$, —N(R$^{6a}$)C(O)R$^{6a}$, —N(R$^{6a}$)C(O)OR$^{6a}$, —N(R$^{6a}$)C(O)N(R$^{6a}$)$_2$, —N(R$^{6a}$)$_2$, —SO$_2$R$^{6a}$, —SO$_2$N(R$^{6a}$)$_2$, —SO$_2$N(R$^{6a}$)COOR$^{6a}$, —SO$_2$N(R$^{6a}$)C(O)R$^{6a}$, —N(R$^{6a}$)SO$_2$R$^{6a}$, a $C_{3-8}$ cycloalkyl ring, a 4 to 7-membered heterocyclic ring, a 5 or 6-membered heteroaryl ring, phenyl, benzyl, an oxo group or a bicyclic group; wherein each 5 or 6-membered heteroaryl ring or 4 to 7-membered heterocyclic ring contains up to 4 ring heteroatoms independently selected from N, O and S, wherein each of said $C_{1-6}$ alkyl, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^{6a}$ is independently selected from hydrogen, a $C_{1-6}$ alkyl, phenyl, benzyl, a $C_{3-8}$ cycloalkyl ring, a 4 to 7-membered heterocyclic ring or a 5 or 6-membered heteroaryl ring, wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo, wherein each of said 5 or 6-membered heteroaryl ring or 4 to 7-membered heterocyclic ring contains up to 4 ring heteroatoms independently selected from N, O and S; or each $R^{5g}$ is independently selected from halogen, —CN, $C_{1-6}$ alkyl, —OR$^{6b}$, —SR$^{6b}$, —COR$^{6b}$, —OC(O)R$^{6b}$, —C(O)OR$^{6b}$, —C(O)N(R$^{6b}$)$_2$, —C(O)N(R$^{6b}$)SO$_2$R$^{6b}$, N(R$^{6b}$)C(O)R$^{6b}$, —N(R$^{6b}$)C(O)OR$^{6b}$, —N(R$^{6b}$)C(O)N(R$^{6b}$)$_2$, —N(R$^{6b}$)$_2$, —SO$_2$R$^{6b}$, —SO$_2$N(R$^{6b}$)$_2$, —SO$_2$N(R$^{6b}$)COOR$^{6b}$, —SO$_2$N(R$^{6b}$)C(O)R$^{6b}$, —N(R$^{6a}$)SO$_2$R$^{6b}$, a $C_{3-8}$ cycloalkyl ring, a 4 to 7-membered heterocyclic ring, a 5 or 6-membered heteroaryl ring, phenyl, benzyl, an oxo group or a bicyclic group; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, $C_{3-8}$ cycloalkyl ring, 4 to 7-membered heterocyclic ring, 5 or 6-membered heteroaryl ring, benzyl or phenyl group is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; wherein said bicyclic group contains ring one and ring two in a fused or bridged relationship, said ring one is a 4 to 7-membered heterocyclic ring, a 5 or 6-membered heteroaryl ring, phenyl or benzyl, and said ring two is a phenyl ring or a 5 or 6-membered heteroaryl ring containing up to 3 ring heteroatoms selected from N, O or S; and wherein said bicyclic group is optionally and independently substituted by up to six instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo;

each $R^{6b}$ is independently selected from hydrogen, a $C_{1-6}$ alkyl, phenyl, benzyl, a $C_{3-8}$ cycloalkyl ring or a 4 to 7-membered heterocyclic ring, a 5 or 6-membered heteroaryl ring; wherein each of said 5 or 6-membered heteroaryl ring or 4 to 7-membered heterocyclic ring contains up to 4 ring heteroatoms independently selected from N, O and S; and wherein each of said $C_{1-6}$ alkyl, each of said phenyl, each of said benzyl, each of said $C_{3-8}$ cycloalkyl group, each of said 4 to 7-membered heterocyclic ring and each of said 5 or 6-membered heteroaryl ring is optionally and independently substituted with up to 3 instances of halogen, $C_{1-4}$ alkyl, —OH, —NH$_2$, —NH($C_{1-4}$ alkyl), —N($C_{1-4}$ alkyl)$_2$, —CN, —COOH, —COO($C_{1-4}$ alkyl), —O($C_{1-4}$ alkyl), —O($C_{1-4}$ haloalkyl) or oxo; or alternatively, two instances of $R^{5g}$ attached to the same or different ring atoms of $R^Y$, together with said ring atom or atoms, form a $C_{3-8}$ cycloalkyl ring, a 4 to 6-membered heterocyclic ring; a phenyl or a 5 or 6-membered heteroaryl ring, resulting in a bicyclic system wherein the two rings are in a spiro, fused or bridged relationship, wherein said 4 to 6-membered heterocycle or said 5 or 6-membered heteroaryl ring contains up to three heteroatoms independently selected from N, O or S; and wherein said $C_{3-8}$ cycloalkyl ring, 4 to 6-membered heterocyclic ring, phenyl or a 5 or 6-membered heteroaryl ring is optionally and independently substituted by up to 3 instances of $C_{1-4}$ alkyl, $C_{1-4}$ haloalkyl, $C_{1-4}$ alkoxy, $C_{1-4}$ haloalkoxy, oxo, —C(O)O($C_{1-4}$ alkyl), —C(O)OH, —NR"(CO)CO($C_{1-4}$ alkyl), —OH or halogen; and R" is hydrogen or a $C_{1-2}$ alkyl.

In some of the compounds of Formula IIIb, or pharmaceutically acceptable salts thereof, $J^A$ and $J^D$, together with the two vicinal ring D atoms to which they are attached, form a 5 to 7-membered heterocycle fused to ring D, wherein said 5 to 7-membered heterocycle contains from 1 to 3 heteroatoms independently selected from N, O or S; and wherein said 5 to 7-membered heterocycle is optionally and independently substituted by up to 3 instances of oxo or —(Y)—R$^9$.

In some of the embodiments of the compounds of Formula IIIb, or pharmaceutically acceptable salts thereof, the compounds are represented by Formula IVb

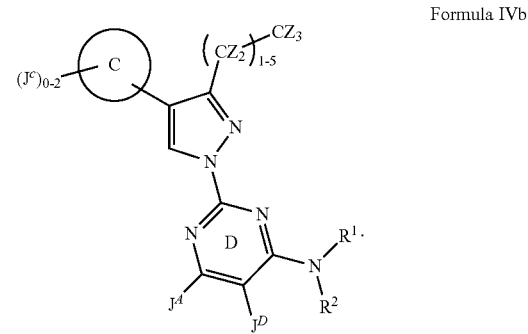

Formula IVb

In some of these compounds, or pharmaceutically acceptable salts thereof, $J^A$ is hydrogen and $J^D$ is fluoro. In some of these compounds, or pharmaceutically acceptable salts thereof, ring C is unsubstituted oxazole or unsubstituted isoxazole. In some of these compounds, or pharmaceutically acceptable salts thereof, $J^A$ and $J^D$, together with the two vicinal ring D atoms to which they are attached, form a 5 to 7-membered heterocycle fused to ring D, wherein said 5 to 7-membered heterocycle contains from 1 to 3 heteroatoms independently selected from N, O or S; and wherein said 5 to 7-membered heterocycle is optionally and independently substituted by up to 3 instances of oxo or —(Y)—$R^9$.

In some of the compounds of Formula IVb, or pharmaceutically acceptable salts thereof, the compounds can be compounds represented by Formula Vb:

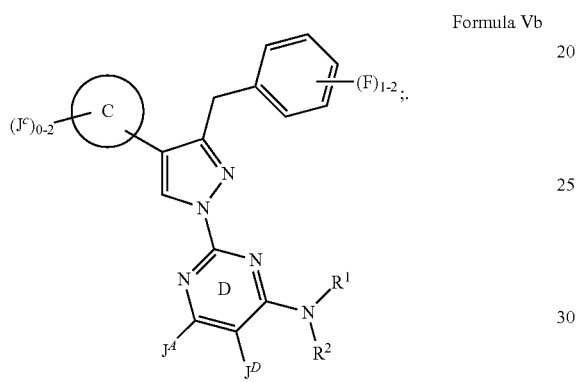

Formula Vb

In some of these compounds, or pharmaceutically acceptable salts thereof, $J^A$ is hydrogen and $J^D$ is fluoro. In some of these compounds, or pharmaceutically acceptable salts thereof, ring C is unsubstituted oxazole or unsubstituted isoxazole. In some of these compounds, or pharmaceutically acceptable salts thereof, $J^A$ and $J^D$, together with the two vicinal ring D atoms to which they are attached, form a 5 to 7-membered heterocycle fused to ring D, wherein said 5 to 7-membered heterocycle contains from 1 to 3 heteroatoms independently selected from N, O or S; and wherein said 5 to 7-membered heterocycle is optionally and independently substituted by up to 3 instances of oxo or —(Y)—$R^9$.

In some of the compounds of Formula IIIb, or pharmaceutically acceptable salts thereof, X is carbon, $J^A$ is hydrogen and $J^D$ is fluoro. In some of these compounds, or pharmaceutically acceptable salts thereof, ring C is unsubstituted oxazole or unsubstituted isoxazole. In some of these compounds, or pharmaceutically acceptable salts thereof, $J^A$ and $J^D$, together with the two vicinal ring D atoms to which they are attached, form a 5 to 7-membered heterocycle fused to ring D, wherein said 5 to 7-membered heterocycle contains from 1 to 3 heteroatoms independently selected from N, O or S; and wherein said 5 to 7-membered heterocycle is optionally and independently substituted by up to 3 instances of oxo or —(Y)—$R^9$.

In some of the embodiments of the compounds of Formula Ib or IIb, or pharmaceutically acceptable salts thereof, $R^C$ is not a ring and X is carbon.

In some of the embodiments of the compounds of Formula IIIb, or pharmaceutically acceptable salts thereof, the compounds are represented by one of Formulae VIb, VIIb, VIc or VIId:

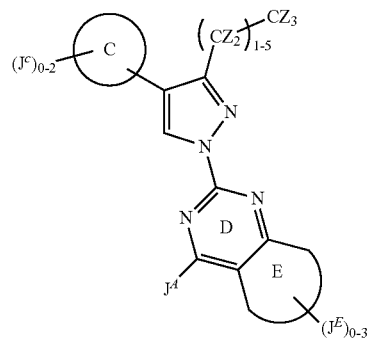

Formula VIb

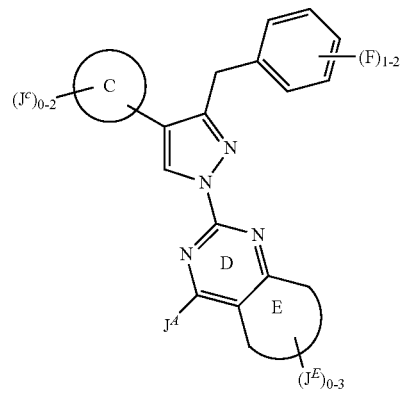

Formula VIIb

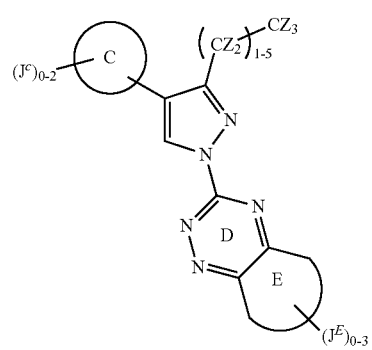

Formula VIc

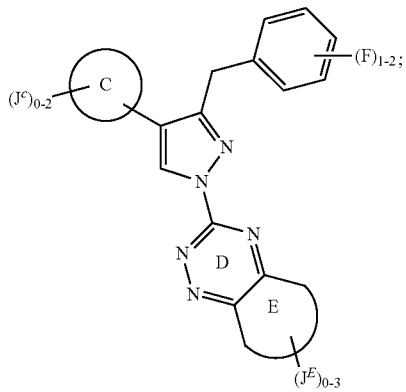

Formula VIId wherein, ring E is a 5 or 6-membered heterocyclic ring, containing up to 3 heteroatoms selected from N, O and S; and wherein each $J^E$ is independently selected from oxo or —(Y)—$R^9$. In some of these compounds, or pharmaceutically acceptable salts thereof, JA is —NH$_2$, —OH, or hydrogen. In some of these compounds, or pharmaceutically acceptable salts thereof, ring E is a heterocyclic ring containing one nitrogen ring atom and wherein at least one instance of $J^E$ is oxo. In some of the embodiments, one $J^E$ is oxo and the other two instances of $J^E$ are independently selected from —(Y)—$R^9$.

In some embodiments of the compounds of Formula I or Formula Ib, ring B is phenyl or a 6-membered heteroaryl ring. In some embodiments, said phenyl or 6-membered heteroaryl ring is unsubstituted and n=0. In other embodiments, ring B is substituted phenyl, pyridine or pyrimidine, and n is an integer selected between 1 and 3.

In some embodiments of the compounds of Formula I or Formula Ib wherein ring B is substituted phenyl, pyridine or pyrimidine, each $J^B$ is independently selected from halogen, a $C_{1-6}$ aliphatic or —$OR^B$. In some embodiments, each $J^B$ is independently selected from a halogen atom. In some embodiments, when $J^B$ is independently selected from a halogen atom, each $J^B$ can be independently selected from fluoro or chloro, or each $J^B$ is fluoro. In other embodiments, each $J^B$ is independently selected from a $C_{1-6}$ aliphatic. In some embodiments, each $J^B$ is methyl or ethyl. In other embodiments, each $J^B$ is methyl. In still other embodiments of the compounds of Formula I or Formula Ib, wherein ring B is substituted phenyl, pyridine or pyrimidine, each $J^B$ is independently selected from —$OR^B$; wherein each $R^B$ is hydrogen or a $C_{1-6}$ alkyl. In some embodiments, each $R^B$ is methyl, ethyl, propyl or isopropyl.

In some of the above embodiments, wherein ring B is substituted phenyl, pyridine or pyrimidine, n is 1 or 2 and each $J^B$ is independently selected from fluoro, chloro, methyl or methoxy. In other embodiments of Formula I and Formula Ib, ring B is a 6-membered heteroaryl ring. In some embodiments, n=0 and the 6-membered heteroaryl ring in unsubstituted. In other embodiments, ring B is a substituted pyridyl ring and n is an integer selected between 1 and 3. In other embodiments, ring B is a substituted pyrimidinyl ring and n is selected between 1 and 3. In some of the above embodiments, wherein ring B is substituted pyridine or pyrimidine, n is 1 or 2 and each $J^B$ is independently selected from fluoro, chloro, methyl or methoxy.

In some embodiments of the compounds of Formula I or Formula Ib, at least one $J^B$ is ortho to the attachment of the methylene linker between ring B and the pyrazolyl ring. In some embodiments, said ortho $J^B$ is independently selected from a halogen atom. In other embodiments, said ortho $J^B$ is selected from fluoro or chloro. In further embodiments, said ortho $J^B$ is fluoro.

In other embodiments of the compounds of Formula I or Formula Ib, ring B is thiophene. In some embodiments, said thiophene ring is a 3-thiophenyl ring. In other embodiments it is a 2-thiophenyl ring. In some embodiments, said thiophene ring is unsubstituted and n=0. In other embodiments, said thiophene is substituted and n is an integer selected from 1, 2 or 3.

In some embodiments of the compounds of Formula I or Formula Ib wherein ring B is substituted thiophene, each $J^B$ is independently selected from halogen, a $C_{1-6}$ aliphatic or —$OR^B$. In other embodiments, each $J^B$ is independently selected from a halogen atom. In some embodiments, when $J^B$ is independently selected from a halogen atom, each $J^B$ can be independently selected from fluoro or chloro, or each $J^B$ is fluoro. In other embodiments, each $J^B$ is independently selected from a $C_{1-6}$ aliphatic. In some embodiments, each $J^B$ is methyl or ethyl. In other embodiments, each $J^B$ is methyl. In still other embodiments of Formula I and Formula Ib, wherein ring B is substituted thiophene, each $J^B$ is independently selected from —$OR^B$; wherein each $R^B$ is hydrogen or a $C_{1-6}$ alkyl. In some embodiments, each $R^B$ is methyl, ethyl, propyl or isopropyl.

In some of the above embodiments, wherein ring B is substituted thiophene, n is 1 or 2 and each $J^B$ is independently selected from fluoro, chloro, methyl or methoxy. In other embodiments, ring B is a mono substituted thiophene and $J^B$ is fluoro.

In other embodiments of the compounds of Formula I or Formula Ib, ring B is a furan ring. In some embodiments, n=0 and the furan ring in unsubstituted. In other embodiments, ring B is a substituted furan ring and n is an integer selected from 1 and 2. In some of the above embodiments, wherein ring B is substituted furan, n is 1 or 2 and each $J^B$ is independently selected from fluoro, chloro, methyl or methoxy. In other embodiments, ring B is a mono substituted furan and $J^B$ is fluoro.

In some embodiments of the compounds of Formula I or Formula Ib, ring D is substituted and o is an integer selected from 1 to 3. In other embodiments, o is 2. In some embodiments o is 2 and the two instances of $J^D$ are attached to two vicinal atoms of ring D.

In those embodiments of the compounds of Formula I or Formula Ib wherein ring D is substituted, each $J^D$ is independently selected from halogen, a $C_{1-6}$ aliphatic, —$N(R^D)_2$, —$N(R^d)C(O)R^D$, —$N(R^d)C(O)OR^D$, —$N(R^d)C(O)N(R^D)_2$, —$SO_2R^D$, —$SO_2N(R^D)_2$, —$N(R^d)SO_2R^D$, —$SR^D$, —$OR^D$ or an optionally substituted $C_{3-8}$ cycloaliphatic ring. In some embodiments of Formula I and Formula Ib, wherein ring D is substituted, o is 1, 2 or 3 and each $J^D$ is independently selected from methyl, chloro, fluoro, —$N(R^D)_2$, —$N(R^d)C(O)R^D$, oxo or —$OR^D$; wherein each $R^d$ is independently selected from hydrogen or methyl. In other embodiments, o is 2 and at least one instance of $J^D$ is independently selected from fluoro, chloro, oxo, hydroxyl or amino.

In some embodiments of the compounds of Formula I or Formula Ib, $R^C$ is a phenyl ring, a monocyclic 5 to or 6-membered heteroaryl ring, a monocyclic 3 to 10-membered cycloaliphatic ring or a monocyclic 4 to 10-membered heterocycle; each of them optionally and independently substituted by up to 6 instances of $J^C$. In other embodiments of Formula I and Formula Ib, ring C is a phenyl ring, a monocyclic 5 to 6-membered heteroaryl ring, a monocyclic 3 to 6-membered cycloaliphatic ring or a monocyclic 4 to 6-membered heterocycle; each of them optionally and independently substituted with up to 3 instances of $J^C$.

In some embodiments of the compounds of Formula I or Formula Ib, $R^C$ is a monocyclic 3 to 6-membered cycloaliphatic ring, optionally and independently substituted with up to 2 instances of $J^C$. In other embodiments, ring C is cyclopropyl, cyclobutyl, cyclopentyl or cyclohexyl. In other embodiments of the compounds of Formula I or Formula Ib, $R^C$ is a ring C which is a 4-membered cycloaliphatic ring substituted by 1 to 3 instances of $J^C$, a 5-membered cycloaliphatic ring substituted by 1 to 4 instances of $J^C$ or a 6-membered cycloaliphatic ring substituted by 1 to 5 instances of $J^C$; wherein each $J^C$ is independently selected from halogen or a $C_{1-6}$ aliphatic.

In other embodiments of the compounds of Formula I or Formula Ib, $R^C$ is phenyl, optionally and independently substituted by up to 5 instances of $J^C$. In some embodiments, ring C is phenyl and it is unsubstituted. In other embodiments, it is substituted by 1 to 3 instances of $J^C$; wherein each $J^C$ is independently selected from halogen, a $C_{1-6}$ aliphatic, —$NH_2$, —CN or —$O(C_{1-6}$ aliphatic). In other embodiments, each $J^C$ is independently selected from halogen, —$NH_2$, —CN, $C_{1-6}$ alkyl or —$O(C_{1-4}$ alkyl). In still other embodiments, ring C is phenyl substituted by 1 to 2 instances of $J^C$ and each $J^C$ is selected from fluoro, chloro, methyl, —CN or —OCH$_3$.

In still other embodiments of Formula I and Formula Ib, $R^C$ is a 5 to 6-membered heteroaryl ring and is optionally and independently substituted by up to 5 instances of $J^C$. In some embodiments, said 5 to 6-membered heteroaryl ring is unsubstituted. In other embodiments, it is substituted with 1 to 3 instances of $J^C$. In some of these embodiments, the 5 to 6-membered heteroaryl ring can be selected from thienyl, thiazolyl, oxadiazolyl, oxazolyl, isooxazolyl, tetrazolyl, pyrrolyl, triazolyl, furanyl, pyridinyl, pyrimidinyl, pyrazinyl or pyridazinyl. In yet other embodiments, ring C is an isoxazolyl or oxazolyl ring and it is unsubstituted.

In some embodiments of Formula I and Formula Ib, ring C is a 5 to 6-membered heteroaryl ring and it is substituted by 1 to 5 instances of $J^C$; wherein each $J^C$ is independently selected from halogen, a $C_{1-6}$ aliphatic, —CN, —NH$_2$ or —O($C_{1-6}$ aliphatic). In other embodiments, ring C is unsubstituted.

In some embodiments, the compounds of the invention are represented by structural Formula I or Formula Ib shown above, or Formula IIA, Formula IIB or Formula IIC shown below:

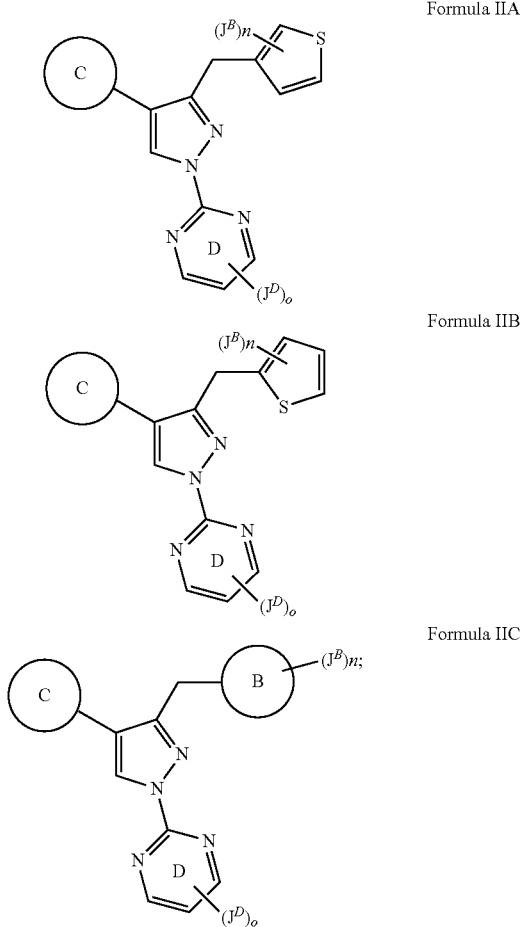

wherein ring B is selected from a phenyl or 6-membered heteroaryl ring; wherein $J^B$ is independently selected from hydrogen or a halogen atom; and wherein n is an integer selected from 1 or 2.

In some embodiments of the compounds of Formulae IIA, IIB or IIC, each $J^B$ is a halogen and the halogen is independently selected from chloro or fluoro. In other embodiments n is 1 and $J^B$ is fluoro. In other embodiments, n is 2 and $J^B$ is either chloro or fluoro. In still other embodiments, n is 2 and all instances of $J^B$ are fluoro.

In some embodiments of the compounds of Formulae IIA, IIB or IIC, o is an integer selected from 1 or 2. In some embodiments of Formulae IIA, IIB and IIC o is 1 or 2 and each $J^D$ is independently selected from halogen, a $C_{1-6}$ aliphatic, —N(R$^D$)$_2$, —N(R$^d$)COR$^D$, —OR$^D$, oxo or an optionally substituted $C_{3-8}$ cycloaliphatic ring. In other embodiments, o is 2 and each $J^D$ is independently selected from a halogen atom or —N(R$^D$)$_2$, —N(R$^d$)COR$^D$, —OH or oxo. In still other embodiments, o is 2 and one instance of $J^D$ is fluoro or chloro and the other instance of $J^D$ is —OH or oxo. In other embodiments, o is 2 and one $J^D$ is —NH$_2$ and the other one is independently selected from —N(R$^D$)$_2$, wherein at least one instance of R$^D$ is not hydrogen, or is —NHCOR$^D$. In still other embodiments, o is 2 and one instance of $J^D$ is independently selected from —N(R$^D$)$_2$ or —NHCOR$^D$ and the other instance of $J^D$ is selected from fluoro or chloro. In still other embodiments, o is 1 and $J^D$ is amino.

In some embodiments of the compounds of Formulae IIA, IIB or IIC, $R^C$ is phenyl, optionally and independently substituted by up to 5 instances of $J^C$. In some embodiments, ring C is phenyl and it is unsubstituted. In other embodiments, it is substituted by 1 to 3 instances of $J^C$; wherein each $J^C$ is independently selected from halogen, a $C_{1-6}$ aliphatic, —NH$_2$, —CN or —O($C_{1-6}$ aliphatic). In other embodiments, each $J^C$ is independently selected from halogen, —NH$_2$, —CN, $C_{1-6}$ alkyl or —O($C_{1-4}$ alkyl). In still other embodiments, ring C is phenyl substituted by 1 to 2 instances of $J^C$ and each $J^C$ is selected from fluoro, chloro, methyl, —CN or —OCH$_3$.

In still other embodiments of the compounds of Formulae IIA, IIB or IIC, $R^C$ is a 5 to 6-membered heteroaryl ring and is optionally and independently substituted by up to 5 instances of $J^C$. In some embodiments, said 5 to 6-membered heteroaryl ring is unsubstituted. In other embodiments, it is substituted with 1 to 3 instances of $J^C$. In some of these embodiments, the 5 to 6-membered heteroaryl ring can be selected from thienyl, thiazolyl, oxadiazolyl, oxazolyl, isoxazolyl, tetrazolyl, pyrrolyl, triazolyl, furanyl, pyridinyl, pyrimidinyl, pyrazinyl or pyridazinyl. In other embodiments, the heteroaryl ring C is selected from isoxazolyl, oxazolyl, furanyl, thienyl, thiazolyl, 1,3,4-oxadiazolyl, pyridinyl, pyrimidinyl or pyrazin-3-yl. In still other embodiments, the heteroaryl ring C is selected from isoxazolyl or oxazolyl. In other embodiments, ring C is a oxazolyl or isoxazolyl ring and it is substituted by up to 2 instances of $J^C$; wherein each $J^C$ is selected from fluoro, chloro, bromo, methyl, —CN, —NH$_2$ or —OCH$_3$. In yet other embodiments of the compounds of Formula I, Formula Ib, Formula IA, Formula IIB or Formula IIC, ring C is an unsubstituted isoxazolyl or oxazolyl ring.

The compounds of the invention are defined herein by their chemical structures and/or chemical names. Where a compound is referred to by both a chemical structure and a chemical name, and the chemical structure and chemical name conflict, the chemical structure is determinative of the compound's identity.

In some embodiments, the compound of Formula I or Formula Ib is one of the compounds depicted below:
TABLE 1
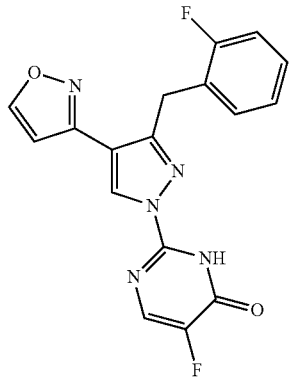 [SMILES: O=c1[nH]c(-n2cc(-c3ccon3)c(Cc3ccccc3F)n2)ncc1F]
I-1
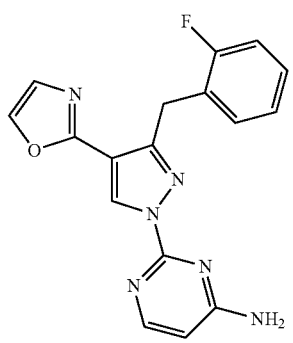 [SMILES: Nc1ccnc(-n2cc(-c3ncco3)c(Cc3ccccc3F)n2)n1]
I-2
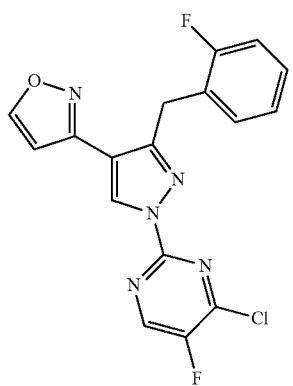 [SMILES: Fc1ccccc1Cc1nn(-c2ncc(F)c(Cl)n2)cc1-c1ccon1]
I-3
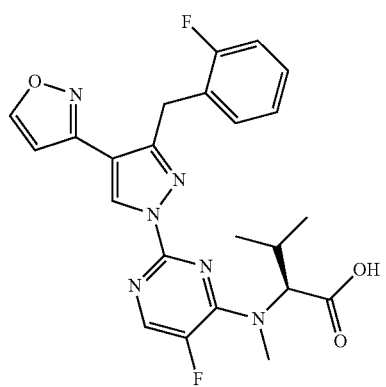 [SMILES: CC(C)[C@@H](C(=O)O)N(C)c1nc(-n2cc(-c3ccon3)c(Cc3ccccc3F)n2)ncc1F]
I-4
TABLE 1-continued
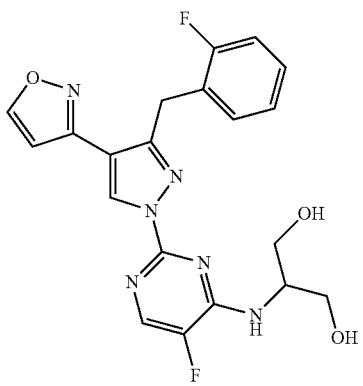 [SMILES: OCC(CO)Nc1nc(-n2cc(-c3ccon3)c(Cc3ccccc3F)n2)ncc1F]
I-5
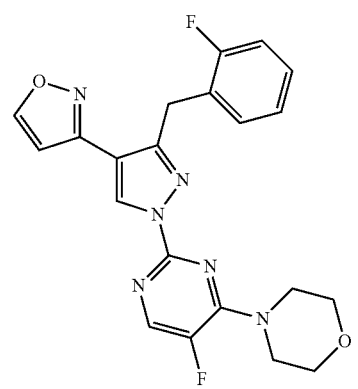 [SMILES: Fc1ccccc1Cc1nn(-c2ncc(F)c(N3CCOCC3)n2)cc1-c1ccon1]
I-6
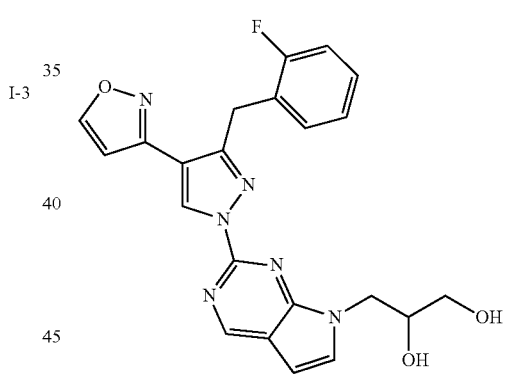
I-7
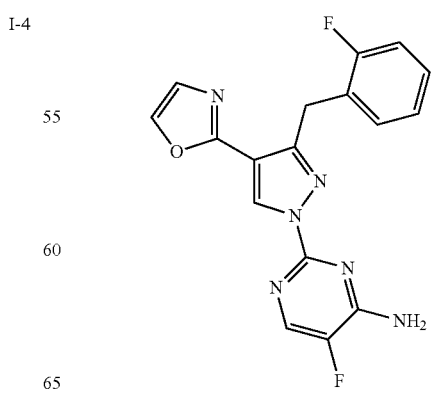
I-8

TABLE 1-continued

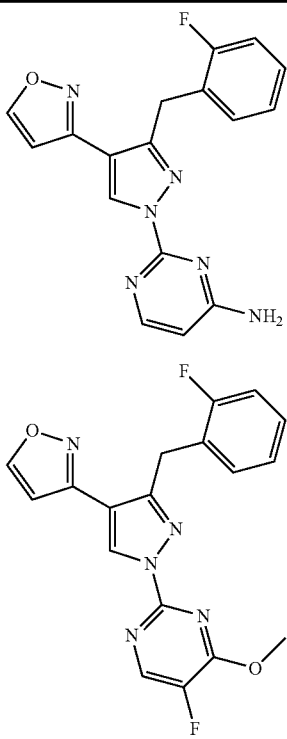

I-9

I-10

Methods of Preparing the Compounds

The compounds of Formula I and Formula Ib may be prepared according to the schemes and examples depicted and described below. Unless otherwise specified, the starting materials and various intermediates may be obtained from commercial sources, prepared from commercially available compounds or prepared using well-known synthetic methods. Another aspect of the present invention is a process for preparing the compounds of Formula I and Formula Ib as disclosed herein.

General synthetic procedures for the compounds of this invention are described below. The synthetic schemes are presented as examples and do not limit the scope of the invention in any way.

Pharmaceutically Acceptable Salts of the Invention.

The phrase "pharmaceutically acceptable salt," as used herein, refers to pharmaceutically acceptable organic or inorganic salts of a compound of Formula I or Formula Ib. For use in medicine, the salts of a compound of Formula I or Formula Ib will be pharmaceutically acceptable salts. Other salts may, however, may be useful in the preparation of a compound of Formula I or Formula Ib or of their pharmaceutically acceptable salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

Pharmaceutically acceptable salts of the compounds of Formula I or Formula IB described herein include those derived from suitable inorganic or organic acids or bases. In some embodiments, the salts can be prepared in situ during the final isolation and purification of the compounds. In other embodiments the salts can be prepared from the free form of the compound in a separate synthetic step.

When a compound of Formula I or Formula Ib is acidic or contains a sufficiently acidic bioisostere, suitable "pharmaceutically acceptable salts" refers to salts prepared form pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particular embodiments include ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine, caffeine, choline, N, N.sup.1-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

When a compound of Formula I or Formula Ib is basic or contains a sufficiently basic bioisostere, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particular embodiments include citric, hydrobromic, hydrochloric, maleic, phosphoric, sulfuric and tartaric acids. Other exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts.

The preparation of the pharmaceutically acceptable salts described above and other typical pharmaceutically acceptable salts is more fully described by Berg et al., "Pharmaceutical Salts," J. Pharm. Sci., 1977:66:1-19, incorporated here by reference in its entirety.

In addition to the compounds described herein, their pharmaceutically acceptable salts may also be employed in compositions to treat or prevent the herein identified disorders.

Pharmaceutical Compositions and Methods of Administration.

The compounds herein disclosed, and their pharmaceutically acceptable salts thereof may be formulated as pharmaceutical compositions or "formulations".

A typical formulation is prepared by mixing a compound of Formula I or Formula Ib, or a pharmaceutically acceptable salt thereof, and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which a compound of Formula I or Formula Ib is being formulated. Solvents are generally selected based on solvents recognized by persons skilled in the art as safe (GRAS-Generally Regarded as Safe) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include other types of excipients such as one or more buffers, stabilizing agents, antiadherents, surfactants, wetting agents, lubricating agents, emulsifiers, binders, suspending agents, disintegrants, fillers, sorbents, coatings (e.g. enteric or slow release) preservatives, antioxidants, opaquing agents, glidants, processing aids, colorants, sweeteners, perfuming agents, flavoring agents and other known additives to provide an elegant presentation of the drug (i.e., a compound of Formula I or Formula Ib or pharmaceutical composition thereof) or aid in the manufacturing of the pharmaceutical product (i.e., medicament).

The formulations may be prepared using conventional dissolution and mixing procedures. For example, the bulk drug substance (i.e., a compound of Formula I or Formula Ib, a pharmaceutically acceptable salt thereof, or a stabilized form of the compound, such as a complex with a cyclodextrin derivative or other known complexation agent) is dissolved in a suitable solvent in the presence of one or more of the excipients described above. A compound having the desired degree of purity is optionally mixed with pharmaceutically acceptable diluents, carriers, excipients or stabilizers, in the form of a lyophilized formulation, milled powder, or an aqueous solution. Formulation may be conducted by mixing at ambient temperature at the appropriate pH, and at the desired degree of purity, with physiologically acceptable carriers. The pH of the formulation depends mainly on the particular use and the concentration of compound, but may range from about 3 to about 8. When the agent described herein is a solid amorphous dispersion formed by a solvent process, additives may be added directly to the spray-drying solution when forming the mixture such as the additive is dissolved or suspended in the solution as a slurry which can then be spray dried. Alternatively, the additives may be added following spray-drying process to aid in the forming of the final formulated product.

The compound of Formula I or Formula Ib or a pharmaceutically acceptable salt thereof is typically formulated into pharmaceutical dosage forms to provide an easily controllable dosage of the drug and to enable patient compliance with the prescribed regimen. Pharmaceutical formulations of a compound of Formula I or Formula Ib, or a pharmaceutically acceptable salt thereof, may be prepared for various routes and types of administration. Various dosage forms may exist for the same compound, since different medical conditions may warrant different routes of administration.

The amount of active ingredient that may be combined with the carrier material to produce a single dosage form will vary depending upon the subject treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight: weight). The pharmaceutical composition can be prepared to provide easily measurable amounts for administration. For example, an aqueous solution intended for intravenous infusion may contain from about 3 to 500 µg of the active ingredient per milliliter of solution in order that infusion of a suitable volume at a rate of about 30 mL/hr can occur. As a general proposition, the initial pharmaceutically effective amount of the inhibitor administered will be in the range of about 0.01-100 mg/kg per dose, namely about 0.1 to 20 mg/kg of patient body weight per day, with the typical initial range of compound used being 0.3 to 15 mg/kg/day.

The term "therapeutically effective amount" as used herein means that amount of active compound or pharmaceutical agent that elicits the biological or medicinal response in a tissue, system, animal or human that is being sought by a researcher, veterinarian, medical doctor or other clinician. The therapeutically or pharmaceutically effective amount of the compound to be administered will be governed by such considerations, and is the minimum amount necessary to ameliorate, cure or treat the disease or disorder or one or more of its symptoms.

The pharmaceutical compositions of a compound of Formula I or Formula Ib will be formulated, dosed, and administered in a fashion, i.e., amounts, concentrations, schedules, course, vehicles, and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners, such as the age, weight, and response of the individual patient.

The term "prophylactically effective amount" refers to an amount effective in preventing or substantially lessening the chances of acquiring a disease or disorder or in reducing the severity of the disease or disorder before it is acquired or reducing the severity of one or more of its symptoms before the symptoms develop. Roughly, prophylactic measures are divided between primary prophylaxis (to prevent the development of a disease) and secondary prophylaxis (whereby the disease has already developed and the patient is protected against worsening of this process).

Acceptable diluents, carriers, excipients, and stabilizers are those that are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, tretralose or sorbitol; salt-forming counter-ions such as sodium; metal complexes (e.g. Zn-protein complexes); and/or non-ionic surfactants such as TWEEN™, PLURONICS™ or polyethylene glycol (PEG). The active pharmaceutical ingredients may also be entrapped in microcapsules prepared, for example, by coacervation techniques or by interfacial polymerization, e.g., hydroxymethylcellulose or gelatin-microcapsules and poly-(methylmethacylate) microcapsules, respectively; in colloidal drug delivery systems (for example, liposomes, albumin microspheres, microemulsions, nanoparticles and nanocapsules) or in macroemulsions. Such techniques are disclosed in Remington's: The Science and Practice of Pharmacy, 21$^{st}$ Edition, University of the Sciences in Philadelphia, Eds., 2005 (hereafter "Remington's").

"Controlled drug delivery systems" supply the drug to the body in a manner precisely controlled to suit the drug and the conditions being treated. The primary aim is to achieve a therapeutic drug concentration at the site of action for the desired duration of time. The term "controlled release" is often used to refer to a variety of methods that modify release of drug from a dosage form. This term includes preparations labeled as "extended release", "delayed release", "modified release" or "sustained release". In general, one can provide for controlled release of the agents described herein through the use of a wide variety of polymeric carriers and controlled release systems including erodible and non-erodible matrices, osmotic control devices, various reservoir devices, enteric coatings and multiparticulate control devices.

"Sustained-release preparations" are the most common applications of controlled release. Suitable examples of sustained-release preparations include semipermeable matrices of solid hydrophobic polymers containing the compound, which matrices are in the form of shaped articles, e.g. films, or microcapsules. Examples of sustained-release matrices include polyesters, hydrogels (for example, poly (2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers, and poly-D-(–)-3-hydroxybutyric acid.

"Immediate-release preparations" may also be prepared. The objective of these formulations is to get the drug into the bloodstream and to the site of action as rapidly as possible. For instance, for rapid dissolution, most tablets are designed to undergo rapid disintegration to granules and subsequent deaggregation to fine particles. This provides a larger surface area exposed to the dissolution medium, resulting in a faster dissolution rate.

Agents described herein can be incorporated into an erodible or non-erodible polymeric matrix controlled release device. By an erodible matrix is meant aqueous-erodible or water-swellable or aqueous-soluble in the sense of being either erodible or swellable or dissolvable in pure water or requiring the presence of an acid or base to ionize the polymeric matrix sufficiently to cause erosion or dissolution. When contacted with the aqueous environment of use, the erodible polymeric matrix imbibes water and forms an aqueous-swollen gel or matrix that entraps the agent described herein. The aqueous-swollen matrix gradually erodes, swells, disintegrates or dissolves in the environment of use, thereby controlling the release of a compound described herein to the environment of use. One ingredient of this water-swollen matrix is the water-swellable, erodible, or soluble polymer, which may generally be described as an osmopolymer, hydrogel or water-swellable polymer. Such polymers may be linear, branched, or cross linked. The polymers may be homopolymers or copolymers. In certain embodiments, they may be synthetic polymers derived from vinyl, acrylate, methacrylate, urethane, ester and oxide monomers. In other embodiments, they can be derivatives of naturally occurring polymers such as polysaccharides (e.g. chitin, chitosan, dextran and pullulan; gum agar, gum arabic, gum karaya, locust bean gum, gum tragacanth, carrageenans, gum ghatti, guar gum, xanthan gum and scleroglucan), starches (e.g. dextrin and maltodextrin), hydrophilic colloids (e.g. pectin), phosphatides (e.g. lecithin), alginates (e.g. ammonium alginate, sodium, potassium or calcium alginate, propylene glycol alginate), gelatin, collagen, and cellulosics. Cellulosics are cellulose polymer that has been modified by reaction of at least a portion of the hydroxyl groups on the saccharide repeat units with a compound to form an ester-linked or an ether-linked substituent. For example, the cellulosic ethyl cellulose has an ether linked ethyl substituent attached to the saccharide repeat unit, while the cellulosic cellulose acetate has an ester linked acetate substituent. In certain embodiments, the cellulosics for the erodible matrix comprises aqueous-soluble and aqueous-erodible cellulosics can include, for example, ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC). In certain embodiments, the cellulosics comprises various grades of low viscosity (MW less than or equal to 50,000 daltons, for example, the Dow Methocel™ series E5, E15LV, E50LV and K100LV) and high viscosity (MW greater than 50,000 daltons, for example, E4MCR, E10MCR, K4M, K15M and K100M and the Methocel™ K series) HPMC. Other commercially available types of HPMC include the Shin Etsu Metolose 90SH series.

Other materials useful as the erodible matrix material include, but are not limited to, pullulan, polyvinyl pyrrolidone, polyvinyl alcohol, polyvinyl acetate, glycerol fatty acid esters, polyacrylamide, polyacrylic acid, copolymers of ethacrylic acid or methacrylic acid (EUDRAGIT®, Rohm America, Inc., Piscataway, N.J.) and other acrylic acid derivatives such as homopolymers and copolymers of butylmethacrylate, methylmethacrylate, ethylmethacrylate, ethylacrylate, (2-dimethylaminoethyl) methacrylate, and (trimethylaminoethyl) methacrylate chloride.

Alternatively, the agents of the present invention may be administered by or incorporated into a non-erodible matrix device. In such devices, an agent described herein is distributed in an inert matrix. The agent is released by diffusion through the inert matrix. Examples of materials suitable for the inert matrix include insoluble plastics (e.g. methyl acrylate-methyl methacrylate copolymers, polyvinyl chloride, polyethylene), hydrophilic polymers (e.g. ethyl cellulose, cellulose acetate, cross linked polyvinylpyrrolidone (also known as crospovidone)), and fatty compounds (e.g. carnauba wax, microcrystalline wax, and triglycerides). Such devices are described further in Remington: The Science and Practice of Pharmacy, 20th edition (2000).

As noted above, the agents described herein may also be incorporated into an osmotic control device. Such devices generally include a core containing one or more agents as described herein and a water permeable, non-dissolving and non-eroding coating surrounding the core which controls the influx of water into the core from an aqueous environment of use so as to cause drug release by extrusion of some or all of the core to the environment of use. In certain embodiments, the coating is polymeric, aqueous-permeable, and has at least one delivery port. The core of the osmotic device optionally includes an osmotic agent which acts to imbibe water from the surrounding environment via such a semi-permeable membrane. The osmotic agent contained in the core of this device may be an aqueous-swellable hydrophilic polymer or it may be an osmogen, also known as an osmagent. Pressure is generated within the device which forces the agent(s) out of the device via an orifice (of a size designed to minimize solute diffusion while preventing the build-up of a hydrostatic pressure head). Non limiting examples of osmotic control devices are disclosed in U.S. patent application Ser. No. 09/495,061.

The amount of water-swellable hydrophilic polymers present in the core may range from about 5 to about 80 wt % (including for example, 10 to 50 wt %). Non limiting examples of core materials include hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP) and cross linked PVP, polyvinyl alcohol (PVA), PVA/PVP copolymers and PVA/PVP copolymers with hydrophobic monomers such as methyl methacrylate, vinyl acetate, and the like, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl cellulose (CEC), sodium alginate, polycarbophil, gelatin, xanthan gum, and sodium starch glycolat. Other materials include hydrogels comprising interpenetrating networks of polymers that may be formed by addition or by condensation polymerization, the components of which may comprise hydrophilic and hydrophobic monomers such as those just mentioned. Water-swellable hydrophilic polymers include but are not limited to PEO, PEG, PVP, sodium croscarmellose, HPMC, sodium starch glycolate, polyacrylic acid and cross linked versions or mixtures thereof.

The core may also include an osmogen (or osmagent). The amount of osmogen present in the core may range from about 2 to about 70 wt % (including, for example, from 10 to 50 wt %). Typical classes of suitable osmogens are water-soluble organic acids, salts and sugars that are capable of imbibing water to thereby effect an osmotic pressure gradient across the barrier of the surrounding coating. Typical useful osmogens include but are not limited to magnesium sulfate, magnesium chloride, calcium chloride, sodium chloride, lithium chloride, potassium sulfate, sodium carbonate, sodium sulfite, lithium sulfate, potassium chloride, sodium sulfate, mannitol, xylitol, urea, sorbitol, inositol, raffinose, sucrose, glucose, fructose, lactose, citric acid, succinic acid, tartaric acid, and mixtures thereof. In certain embodiments, the osmogen is glucose, lactose, sucrose, mannitol, xylitol, sodium chloride, including combinations thereof.

The rate of drug delivery is controlled by such factors as the permeability and thickness of the coating, the osmotic pressure of the drug-containing layer, the degree of hydrophilicity of the hydrogel layer, and the surface area of the device. Those skilled in the art will appreciate that increasing the thickness of the coating will reduce the release rate, while any of the following will increase the release rate: increasing the permeability of the coating; increasing the hydrophilicity of the hydrogel layer; increasing the osmotic pressure of the drug-containing layer; or increasing the device's surface area.

In certain embodiments, entrainment of particles of agents described herein in the extruding fluid during operation of such osmotic device is desirable. For the particles to be well entrained, the agent drug form is dispersed in the fluid before the particles have an opportunity to settle in the tablet core. One means of accomplishing this is by adding a disintegrant that serves to break up the compressed core into its particulate components. Non limiting examples of standard disintegrants include materials such as sodium starch glycolate (e. g., Explotab™ CLV), microcrystalline cellulose (e. g., Avicel™), microcrystalline silicified cellulose (e. g., ProSolv™) and croscarmellose sodium (e. g., Ac-Di-Sol™), and other disintegrants known to those skilled in the art. Depending upon the particular formulation, some disintegrants work better than others. Several disintegrants tend to form gels as they swell with water, thus hindering drug delivery from the device. Non-gelling, non-swelling disintegrants provide a more rapid dispersion of the drug particles within the core as water enters the core. In certain embodiments, non-gelling, non-swelling disintegrants are resins, for example, ion-exchange resins. In one embodiment, the resin is Amberlite™ IRP 88 (available from Rohm and Haas, Philadelphia, Pa.). When used, the disintegrant is present in amounts ranging from about 1-25% of the core agent.

Another example of an osmotic device is an osmotic capsule. The capsule shell or portion of the capsule shell can be semipermeable. The capsule can be filled either by a powder or liquid consisting of an agent described herein, excipients that imbibe water to provide osmotic potential, and/or a water-swellable polymer, or optionally solubilizing excipients. The capsule core can also be made such that it has a bilayer or multilayer agent analogous to the bilayer, trilayer or concentric geometries described above.

Another class of osmotic device useful in this invention comprises coated swellable tablets, for example, as described in EP378404. Coated swellable tablets comprise a tablet core comprising an agent described herein and a swelling material, preferably a hydrophilic polymer, coated with a membrane, which contains holes, or pores through which, in the aqueous use environment, the hydrophilic polymer can extrude and carry out the agent. Alternatively, the membrane may contain polymeric or low molecular weight water-soluble porosigens. Porosigens dissolve in the aqueous use environment, providing pores through which the hydrophilic polymer and agent may extrude. Examples of porosigens are water-soluble polymers such as HPMC, PEG, and low molecular weight compounds such as glycerol, sucrose, glucose, and sodium chloride. In addition, pores may be formed in the coating by drilling holes in the coating using a laser or other mechanical means. In this class of osmotic devices, the membrane material may comprise any film-forming polymer, including polymers which are water permeable or impermeable, providing that the membrane deposited on the tablet core is porous or contains water-soluble porosigens or possesses a macroscopic hole for water ingress and drug release. Embodiments of this class of sustained release devices may also be multilayered, as described, for example, in EP378404.

When an agent described herein is a liquid or oil, such as a lipid vehicle formulation, for example as described in WO05/011634, the osmotic controlled-release device may comprise a soft-gel or gelatin capsule formed with a composite wall and comprising the liquid formulation where the wall comprises a barrier layer formed over the external surface of the capsule, an expandable layer formed over the barrier layer, and a semipermeable layer formed over the expandable layer. A delivery port connects the liquid formulation with the aqueous use environment. Such devices are described, for example, in U.S. Pat. No. 6,419,952, U.S. Pat. No. 6,342,249, U.S. Pat. No. 5,324,280, U.S. Pat. No. 4,672,850, U.S. Pat. No. 4,627,850, U.S. Pat. No. 4,203,440, and U.S. Pat. No. 3,995,631.

As further noted above, the agents described herein may be provided in the form of microparticulates, generally ranging in size from about 10 μm to about 2 mm (including, for example, from about 100 μm to 1 mm in diameter). Such multiparticulates may be packaged, for example, in a capsule such as a gelatin capsule or a capsule formed from an aqueous-soluble polymer such as HPMCAS, HPMC or starch; dosed as a suspension or slurry in a liquid; or they may be formed into a tablet, caplet, or pill by compression or other processes known in the art. Such multiparticulates may be made by any known process, such as wet- and dry-granulation processes, extrusion/spheronization, roller-compaction, melt-congealing, or by spray-coating seed cores. For example, in wet- and dry-granulation processes, the agent described herein and optional excipients may be granulated to form multiparticulates of the desired size.

The agents can be incorporated into microemulsions, which generally are thermodynamically stable, isotropically clear dispersions of two immiscible liquids, such as oil and water, stabilized by an interfacial film of surfactant molecules (Encyclopedia of Pharmaceutical Technology, New York: Marcel Dekker, 1992, volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifier") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

The compounds described herein can be incorporated into pharmaceutically-acceptable nanoparticle, nanosphere, and nanocapsule formulations (Delie and Blanco-Prieto, 2005, Molecule 10:65-80). Nanocapsules can generally entrap compounds in a stable and reproducible way. To avoid side effects due to intracellular polymeric overloading, ultrafine particles (sized around 0.1 μm) can be designed using polymers able to be degraded in vivo (e.g. biodegradable polyalkyl-cyanoacrylate nanoparticles). Such particles are described in the prior art.

Implantable devices coated with a compound of this invention are another embodiment of the present invention. The compounds may also be coated on implantable medical devices, such as beads, or co-formulated with a polymer or other molecule, to provide a "drug depot", thus permitting the drug to be released over a longer time period than administration of an aqueous solution of the drug. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

The formulations include those suitable for the administration routes detailed herein. The formulations may conveniently be presented in unit dosage form and may be prepared by any of the methods well known in the art of pharmacy. Techniques and formulations generally are found in Remington's. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

The terms "administer", "administering" or "administration" in reference to a compound, composition or formulation of the invention means introducing the compound into the system of the animal in need of treatment. When a compound of the invention is provided in combination with one or more other active agents, "administration" and its variants are each understood to include concurrent and/or sequential introduction of the compound and the other active agents.

The compositions described herein may be administered systemically or locally, e.g.: orally (e.g. using capsules, powders, solutions, suspensions, tablets, sublingual tablets and the like), by inhalation (e.g. with an aerosol, gas, inhaler, nebulizer or the like), to the ear (e.g. using ear drops), topically (e.g. using creams, gels, liniments, lotions, ointments, pastes, transdermal patches, etc), ophthalmically (e.g. with eye drops, ophthalmic gels, ophthalmic ointments), rectally (e.g. using enemas or suppositories), nasally, buccally, vaginally (e.g. using douches, intrauterine devices, vaginal suppositories, vaginal rings or tablets, etc), via an implanted reservoir or the like, or parenterally depending on the severity and type of the disease being treated. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

The pharmaceutical compositions described herein may be orally administered in any orally acceptable dosage form including, but not limited to, capsules, tablets, aqueous suspensions or solutions. Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a)

fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. Tablets may be uncoated or may be coated by known techniques including microencapsulation to mask an unpleasant taste or to delay disintegration and adsorption in the gastrointestinal tract and thereby provide a sustained action over a longer period. For example, a time delay material such as glyceryl monostearate or glyceryl distearate alone or with a wax may be employed. A water soluble taste masking material such as hydroxypropyl-methylcellulose or hydroxypropyl-cellulose may be employed.

Formulations of a compound of Formula I or Formula Ib that are suitable for oral administration may be prepared as discrete units such as tablets, pills, troches, lozenges, aqueous or oil suspensions, dispersible powders or granules, emulsions, hard or soft capsules, e.g. gelatin capsules, syrups or elixirs. Formulations of a compound intended for oral use may be prepared according to any method known to the art for the manufacture of pharmaceutical compositions.

Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered active ingredient moistened with an inert liquid diluent.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

The active compounds can also be in microencapsulated form with one or more excipients as noted above.

When aqueous suspensions are required for oral use, the active ingredient is combined with emulsifying and suspending agents. If desired, certain sweetening and/or flavoring agents may be added. Syrups and elixirs may be formulated with sweetening agents, for example glycerol, propylene glycol, sorbitol or sucrose. Such formulations may also contain a demulcent, a preservative, flavoring and coloring agents and antioxidant.

Sterile injectable forms of the compositions described herein (e.g. for parenteral administration) may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of injectable formulations.

Oily suspensions may be formulated by suspending a compound of Formula I or Formula Ib in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Aqueous suspensions of a compound of Formula I or Formula Ib contain the active materials in admixture with excipients suitable for the manufacture of aqueous suspensions. Such excipients include a suspending agent, such as sodium carboxymethylcellulose, croscarmellose, povidone, methylcellulose, hydroxypropyl methylcelluose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethyleneoxycetanol), a condensation product of ethylene oxide with a partial ester derived from a fatty acid and a hexitol anhydride (e.g., polyoxyethylene sorbitan monooleate). The aqueous suspension may also contain one or more preservatives such as ethyl or n-propyl p-hydroxy-benzoate, one or more coloring agents, one or more flavoring agents and one or more sweetening agents, such as sucrose or saccharin.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsulated matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

The injectable solutions or microemulsions may be introduced into a patient's bloodstream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

Compositions for rectal or vaginal administration are preferably suppositories which can be prepared by mixing the compounds described herein with suitable non-irritating excipients or carriers such as cocoa butter, beeswax, polyethylene glycol or a suppository wax which are solid at ambient temperature but liquid at body temperature and therefore melt in the rectum or vaginal cavity and release the active compound. Other formulations suitable for vaginal administration may be presented as pessaries, tampons, creams, gels, pastes, foams or sprays.

The pharmaceutical compositions described herein may also be administered topically, especially when the target of treatment includes areas or organs readily accessible by topical application, including diseases of the eye, the ear, the skin, or the lower intestinal tract. Suitable topical formulations are readily prepared for each of these areas or organs.

Dosage forms for topical or transdermal administration of a compound described herein include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel. Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum. For treatment of the eye or other external tissues, e.g., mouth and skin, the formulations may be applied as a topical ointment or cream containing the active ingredient(s) in an amount of, for example, 0.075 to 20% w/w. When formulated in an ointment, the active ingredients may be employed with either an oil-based, paraffinic or a water-miscible ointment base.

Alternatively, the active ingredients may be formulated in a cream with an oil-in-water cream base. If desired, the aqueous phase of the cream base may include a polyhydric alcohol, i.e. an alcohol having two or more hydroxyl groups such as propylene glycol, butane 1,3-diol, mannitol, sorbitol, glycerol and polyethylene glycol (including PEG 400) and mixtures thereof. The topical formulations may desirably include a compound which enhances absorption or penetration of the active ingredient through the skin or other affected areas. Examples of such dermal penetration enhancers include dimethyl sulfoxide and related analogs.

The oily phase of emulsions prepared using a compound of Formula I or Formula Ib may be constituted from known ingredients in a known manner. While the phase may comprise merely an emulsifier (otherwise known as an emulgent), it desirably comprises a mixture of at least one emulsifier with a fat or an oil or with both a fat and an oil. A hydrophilic emulsifier may be included together with a lipophilic emulsifier which acts as a stabilizer. In some embodiments, the emulsifier includes both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. Emulgents and emulsion stabilizers suitable for use in the formulation of a compound of Formula I or Formula Ib include Tween™-60, Span™-80, cetostearyl alcohol, benzyl alcohol, myristyl alcohol, glyceryl monostearate and sodium lauryl sulfate.

The pharmaceutical compositions may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Formulations suitable for intrapulmonary or nasal administration have a particle size for example in the range of 0.1 to 500 micros (including particles in a range between 0.1 and 500 microns in increments microns such as 0.5, 1, 30, 35 microns, etc) which is administered by rapid inhalation through the nasal passage or by inhalation through the mouth so as to reach the alveolar sacs.

The pharmaceutical composition (or formulation) for use may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

In another aspect, a compound of Formula I or Formula Ib or a pharmaceutically acceptable salt thereof may be formulated in a veterinary composition comprising a veterinary carrier. Veterinary carriers are materials useful for the purpose of administering the composition and may be solid, liquid or gaseous materials which are otherwise inert or accep Formula I or Formula Ib in the veterinary art and are compatible with the active ingredient. These veterinary compositions may be administered parenterally, orally or by any other desired route.

Therapeutic Methods

The present disclosure relates to stimulators of soluble guanylate cyclase (sGC), pharmaceutical formulations thereof and their use, alone or in combination with one or more additional agents, for treating and/or preventing various diseases, wherein an increase in the concentration of NO or an increase in the concentration of cGMP might be desirable. The diseases that can be treated include but are not limited to pulmonary hypertension, arterial hypertension, portal hypertension, heart failure, atherosclerosis, inflammation, thrombosis, obstructive thromboanginitis, renal fibrosis and failure, liver cirrhosis, cancer metastasis, female sexual disorders, erectile dysfunction, vaginal atrophy, wound healing and other related cardiovascular disorders.

Increased concentration of cGMP leads to vasodilation, inhibition of platelet aggregation and adhesion, anti-hypertensive effects, anti-remodeling effects, anti-apoptotic effects, anti-inflammatory effects and neuronal signal transmission effects. Thus, sGC stimulators may be used to treat and/or prevent a range of diseases and disorders, including but not limited to a peripheral, pulmonary, hepatic, liver, cardiac or cerebralvascular/endothelial disorders or conditions, a urogenital-gynecological disorder or condition, a thromboembolic disease, a fibrotic disorder, a pulmonary or respiratory disorder, a renal or hepatic disorder, a metabolic disorder, atherosclerosis, or a lipid related disorder.

In other embodiments, the compounds here disclosed are sGC stimulators that may be useful in the prevention and/or treatment of diseases and disorders characterized by undesirable reduced bioavailability of and/or sensitivity to NO, such as those associated with conditions of oxidative stress or nitrosative stress.

Throughout this disclosure, the terms "hypertension", "arterial hypertension" or "high blood pressure (HBP)" are used interchangeable and refer to an extremely common and highly preventable chronic condition in which blood pressure (BP) in the arteries is higher than normal. If not properly controlled, it represents a significant risk factor for several serious cardiovascular and renal conditions. Hypertension may be a primary disease, called "essential hypertension" or "idiopathic hypertension", or it may be caused by other diseases, in which case it is classified as "secondary hypertension". Essential hypertension accounts for 90-95% of all cases.

As used herein, the term "resistant hypertension" refers to hypertension that remains above goal blood pressure (usually less than 140/90 mmHg, although a lower goal of less than 130/80 mmHg is recommended for patients with comorbid diabetes or kidney disease), in spite of concurrent use of three antihypertensive agents belonging to different antihypertensive drug classes. People who require four or more drugs to control their blood pressure are also considered to have resistant hypertension.

Hypertension is an extremely common comorbid condition in diabetes, affecting ~20-60% of patients with diabetes, depending on obesity, ethnicity, and age. This type of hypertension is herein referred to as "diabetic hypertension". In type 2 diabetes, hypertension is often present as part of the metabolic syndrome of insulin resistance also including central obesity and dyslipidemia. In type 1 diabetes, hypertension may affect the onset of diabetic nephropathy.

"Pulmonary hypertension (PH)", as used herein, is a disease characterized by sustained elevations of blood pressure in the pulmonary vasculature (pulmonary artery, pulmonary vein and pulmonary capillaries), which results in cardiac hypertrophy, right heart hypertrophy, eventually leading to right heart failure and death. Common symptoms of PH include shortness of breath, dizziness and fainting, all of which are exacerbated by exertion. Without treatment, median life expectancy following diagnosis is 2.8 years. PH exists in many different forms, which are categorized according to their etiology. Categories include pulmonary arterial hypertension (PAH), PH with left heart disease, PH associated with lung diseases and/or hypoxaemia, PH due to chronic thrombotic and/or embolic disease and miscellaneous PH. PAH is rare in the general population, but the prevalence increases in association with certain common conditions such as HIV infection, scleroderma and sickle cell disease. Other forms of PH are generally more common than PAH, and, for instance, the association of PH with chronic obstructive pulmonary disease (COPD) is of particular concern. Current treatment for pulmonary hypertension depends on the stage and the mechanism of the disease.

As used herein "heart failure" is a progressive disorder of left ventricular (LV) myocardial remodeling that culminates in a complex clinical syndrome in which impaired cardiac function and circulatory congestion are the defining features, and results in insufficient delivery of blood and nutrients to body tissues. The condition occurs when the heart is damaged or overworked and unable to pump out all the blood that returns to it from the systemic circulation. As less blood is pumped out, blood returning to the heart backs up and fluid builds up in other parts of the body. Heart failure also impairs the kidneys' ability to dispose of sodium and water, complicating fluid retention further. Heart failure is characterized by autonomic dysfunction, neurohormonal activation and overproduction of cytokines, which contribute to progressive circulatory failure. Symptoms of heart failure include: dyspnea (shortness of breath) while exercising or resting and waking at night due to sudden breathlessness, both indicative of pulmonary edema; general fatigue or weakness, edema of the feet, ankles and legs, rapid weight gain, chronic cough, including that producing mucus or blood. Depending on its clinical presentation, heart failure is classified as de novo, transient or chronic. Acute heart failure, i.e. the rapid or gradual onset of symptoms requiring urgent therapy, may develop de novo or as a result of chronic heart failure becoming decompensated. Diabetes is a common comorbidity in patients with heart failure and is associated with poorer outcomes as well as potentially compromising the efficacy of treatments. Other important comorbidities include systemic hypertension, chronic airflow obstruction, sleep apnea, cognitive dysfunction, anemia, chronic kidney disease and arthritis. Chronic left heart failure is frequently associated with the development of pulmonary hypertension. The frequency of certain comorbidities varies by gender: among women, hypertension and thyroid disease are more common, while men more commonly suffer from chronic obstructive pulmonary disease, bronchoconstriction, pulmonary vasoconstriction, acute pulmonary distress syndrome, peripheral vascular disease, coronary artery disease and renal insufficiency. Depression is a frequent comorbidity of heart failure and the two conditions can and often do complicate one another. Cachexia has long been recognized as a serious and frequent complication of heart failure, affecting up to 15% of all heart failure patients and being associated with poor prognosis. Cardiac cachexia is defined as the nonedematous, nonvoluntary loss of at least 6% of body weight over a period of six months.

The term "sleep apnea" refers to the most common of the sleep-disordered breathing disorders. It is a condition characterized by intermittent, cyclical reductions or total cessations of airflow, which may or may not involve obstruction of the upper airway. There are three types of sleep apnea: obstructive sleep apnea, the most common form, central sleep apnea and mixed sleep apnea.

"Central sleep apnea (CSA)", is caused by a malfunction in the brain's normal signal to breathe, rather than physical blockage of the airway. The lack of respiratory effort leads to an increase in carbon dioxide in the blood, which may rouse the patient. CSA is rare in the general population, but is a relatively common occurrence in patients with systolic heart failure.

As used herein, the term "metabolic syndrome", "insulin resistance syndrome" or "syndrome X", refers to a group or clustering of metabolic conditions (abdominal obesity, elevated fasting glucose, "dyslipidemia" (i.e., elevated lipid levels) and elevated blood pressure (HBP)) which occur together more often than by chance alone and that together promote the development of type 2 diabetes and cardiovascular disease. Metabolic syndrome is characterized by a specific lipid profile of increased triglycerides, decreased high-density lipoprotein cholesterol (HDL-cholesterol) and in some cases moderately elevated low-density lipoprotein cholesterol (LDL-cholesterol) levels, as well as accelerated progression of "atherosclerotic disease" due to the pressure of the component risk factors. There are several types of dyslipidemias: "hypercholesterolemia" refers to elevated levels of cholesterol. Familial hypercholesterolemia is a specific form of hypercholesterolemia due to a defect on chromosome 19 (19p13.1-13.3). "Hyperglyceridemia" refers to elevated levels of glycerides (e.g., "hypertrigliceridemia" involves elevated levels of triglycerides). "Hyperlipoproteinemia" refers to elevated levels of lipoproteins (usually LDL unless otherwise specified).

As used herein, the term "peripheral vascular disease (PVD)", also commonly referred to as "peripheral arterial disease (PAD)" or "peripheral artery occlusive disease (PAOD)", refers to the obstruction of large arteries not within the coronary, aortic arch vasculature, or brain. PVD can result from atherosclerosis, inflammatory processes leading to stenosis, an embolism, peripheral embolism, or thrombus formation. It causes either acute or chronic "ischemia (lack of blood supply)". Often PVD is a term used to refer to atherosclerotic blockages found in the lower extremity. PVD also includes a subset of diseases classified as microvascular diseases resulting from episodal narrowing of the arteries (e.g., "Raynaud's phenomenon"), or widening thereof (erythromelalgia), i.e. vascular spasms.

The term "thrombosis" refers to the formation of a blood clot ("thrombus") inside a blood vessel, obstructing the flow of blood through the circulatory system. When a blood vessel is injured, the body uses platelets (thrombocytes) and fibrin to form a blood clot to prevent blood loss. Alternatively, even when a blood vessel is not injured, blood clots may form in the body if the proper conditions present themselves. If the clotting is too severe and the clot breaks free, the traveling clot is now known as an "embolus". The term "thromboembolism" refers to the combination of thrombosis and its main complication, "embolism". When a thrombus occupies more than 75% of surface area of the lumen of an artery, blood flow to the tissue supplied is reduced enough to cause symptoms because of decreased oxygen (hypoxia) and accumulation of metabolic products like lactic acid ("gout"). More than 90% obstruction can result in anoxia, the complete deprivation of oxygen, and "infarction", a mode of cell death.

An "embolism" (plural embolisms) is the event of lodging of an embolus (a detached intravascular mass capable of clogging arterial capillary beds at a site far from its origin) into a narrow capillary vessel of an arterial bed which causes a blockage (vascular occlusion) in a distant part of the body. This is not to be confused with a thrombus which blocks at the site of origin.

A "stroke", or cerebrovascular accident (CVA), is the rapid loss of brain function(s) due to disturbance in the blood supply to the brain. This can be due to "ischemia" (lack of blood flow) caused by blockage (thrombosis, arterial embolism, peripheral embolism), or a hemorrhage (leakage of blood). As a result, the affected area of the brain cannot function, which might result in an inability to move one or more limbs on one side of the body, inability to understand or formulate speech, or an inability to see one side of the visual field. Risk factors for stroke include old age, hypertension, previous stroke or transient ischemic attack (TIA), diabetes, high cholesterol, cigarette smoking and atrial fibrillation. High blood pressure is the most important modifiable risk factor of stroke. An "ischemic stroke" is occasionally treated in a hospital with thrombolysis (also known as a "clot buster"), and some hemorrhagic strokes benefit from neurosurgery. Prevention of recurrence may involve the administration of antiplatelet drugs such as aspirin and dipyridamole, control and reduction of hypertension, and the use of statins. Selected patients may benefit from carotid endarterectomy and the use of anticoagulants.

"Ischemia", is a restriction in blood supply to tissues, causing a shortage of oxygen and glucose needed for cellular metabolism (to keep tissue alive). Ischemia is generally caused by problems with blood vessels, with resultant damage to or dysfunction of tissue. It also means local anemia in a given part of a body sometimes resulting from congestion (such as vasoconstriction, thrombosis or embolism).

According to the American Psychiatric Association's Diagnostic and Statistical Manual of Mental Disorders, Fourth Edition (DSM-IV), the term "sexual dysfunction" encompasses a series of conditions "characterized by disturbances in sexual desire and in the psychophysiological changes associated with the sexual response cycle"; while problems of this type are common, sexual dysfunction is only considered to exist when the problems cause distress for the patient. Sexual dysfunction can be either physical or psychological in origin. It can exist as a primary condition, generally hormonal in nature, although most often it is secondary to other medical conditions or to drug therapy for said conditions. All types of sexual dysfunction can be further classified as life-long, acquired, situational or generalized (or combinations thereof).

The DSM-IV-TR specifies five major categories of "female sexual dysfunction": sexual desire/interest disorders; "sexual arousal disorders (including genital, subjective and combined)"; orgasmic disorder; dyspareunia and vaginismus; and persistent sexual arousal disorder.

"Female sexual arousal disorder (FSAD)" is defined as a persistent or recurring inability to attain or maintain sufficient levels of sexual excitement, causing personal distress. FSAD encompasses both the lack of subjective feelings of excitement (i.e., subjective sexual arousal disorder) and the lack of somatic responses such as lubrication and swelling (i.e., genital/physical sexual arousal disorder). FSAD may be strictly psychological in origin, although it generally is caused or complicated by medical or physiological factors. Hypoestrogenism is the most common physiologic condition associated with FSAD, which leads to urogenital atrophy and a decrease in vaginal lubrication.

As used herein, "erectile dysfunction (ED)" is a male sexual dysfunction characterized by the inability to develop or maintain an erection of the penis during sexual performance. A penile erection is the hydraulic effect of blood entering and being retained in sponge-like bodies within the penis. The process is often initiated as a result of sexual arousal, when signals are transmitted from the brain to nerves in the penis. Erectile dysfunction is indicated when an erection is difficult to produce. The most important organic causes are cardiovascular disease and diabetes, neurological problems (for example, trauma from prostatectomy surgery), hormonal insufficiencies (hypogonadism) and drug side effects.

(1) Specific diseases of disorders which may be treated and/or prevented by administering an sGC stimulator of the invention, include but are not limited to: hypertension (e.g., diabetic hypertension, arterial hypertension, portal hypertension, pulmonary hypertension, resistant hypertension, peripheral vascular disease, peripheral artery disease, etc), heart failure (e.g., diastolic dysfunction, left ventricular diastolic dysfunction (LVDD) and left ventricular systolic dysfunction (LVSD), sleep apnea associated with heart failure), arteriosclerotic disease (e.g., atherosclerosis), thromboembolic disorders (e.g., chronic thromboembolic pulmonary hypertension, thrombosis, obstructive thromboanginosis, stroke, embolism, pulmonary embolism, peripheral embolism), renal diseases (e.g., renal fibrosis, ischemic renal disease, renal failure, renal insufficiency, chronic kidney disease), hepatic disease (e.g., liver fibrosis or cirrhosis), respiratory disease (e.g., pulmonary fibrosis, asthma, chronic obstructive pulmonary disease, bronchoconstriction, pulmonary vasoconstriction, acute respiratory distress syndrome, interstitial lung disease), sexual disorders (e.g., erectile dysfunction, male and female sexual dysfunction, vaginal atrophy), sickle cell anemia, neuro inflammatory diseases or disorders and metabolic disorders (e.g., lipid related disorders), wound healing (e.g., in diabetics), microvascular or microcirculation abnormalities, control of vascular leakage and permeability, endothelial dysfunction, inhibition of modulation of platelet aggregation, anal fissures.

The compounds of Formula I and Formula Ib as well as pharmaceutically acceptable salts thereof, as stimulators of sGC, are useful in the prevention and/or treatment of the following types of diseases, conditions and disorders which can benefit from sGC stimulation:

a. Peripheral, pulmonary, hepatic, liver, cardiac or cerebral vascular/endothelial disorders/conditions:

disorders related to high blood pressure and decreased coronary blood flow such as increased acute and chronic coronary blood pressure, arterial hypertension and vascular disorder resulting from cardiac and renal complications (e.g. heart disease, stroke, cerebral ischemia, renal failure); resistant hypertension, diabetic hypertension, diabetic nephropathy, congestive heart failure; diastolic or sistolic dysfunction; coronary insufficiency; arrhythmias; diastolic dysfunction;

thromboembolic disorders and ischemias such as myocardial infarction, stroke, transient ischemic attacks (TIAs); stable or unstable angina pectoris;

peripheral arterial disease, peripheral occlusive arterial disease, intermittent claudication, critical limb ischemia, vasculitis pulmonary/respiratory conditions such as pulmonary hypertension, pulmonary arterial hypertension, portal hypertension, acute respiratory distress syndrome, and associated pulmonary vascular remodeling (e.g. localized thrombosis and right heart hypertrophy); pulmonary hypertonia; primary pulmonary hypertension, secondary pulmonary hypertension, familial pulmonary hypertension, sporadic pulmonary hypertension, pre-capillary pulmonary hypertension, idiopathic pulmonary hypertension, thrombotic pulmonary arteriopathy, plexogenic pulmonary arteriopathy;

pulmonary hypertension associated with or related to: left ventricular dysfunction, hypoxemia, mitral valve disease, constrictive pericarditis, aortic stenosis, cardiomyopathy, mediastinal fibrosis, pulmonary fibrosis, anomalous pulmonary venous drainage, pulmonary venoocclusive disease, pulmonary vasculitis, collagen vascular disease, congenital heart disease, pulmonary venous hypertension, interstitial lung disease, sleep-disordered breathing, sleep apnea, alveolar hypoventilation disorders, chronic exposure to high altitude, neonatal lung disease, alveolar-capillary dysplasia, sickle cell disease, other coagulation disorders, chronic thromboembolism, pulmonary embolism (due to tumor, parasites or foreign material), peripheral embolism, connective tissue disease, lupus, schitosomiasis, sarcoidosis, chronic obstructive pulmonary disease, bronchoconstriction, pulmonary vasoconstriction, acute respiratory distress syndrome, asthma, emphysema, chronic bronchitis, pulmonary capillary hemangiomatosis; histiocytosis X, lymphangiomatosis and compressed pulmonary vessels (such as due to adenopathy, tumor or fibrosing mediastinitis);

arterosclerotic diseases or conditions such as atherosclerosis (e.g., associated with endothelial injury, platelet and monocyte adhesion and aggregation, smooth muscle proliferation and migration); restenosis (e.g. developed after thrombolysis therapies, percutaneous transluminal angioplasties (PTAs), percutaneous transluminal coronary angioplasties (PTCAs) and bypass); inflammation; thrombogenic diseases;

cardiovascular disease associated with metabolic syndrome (e.g., obesity, dyslipidemia, diabetis, high blood pressure); lipid related disorders such as dyslipidemia, hypercholesterolemia, hypertriglyceridemia, sitosterolemia, fatty liver disease, and hepatitis;

liver cirrhosis, associated with chronic liver disease, hepatic fibrosis, hepatic stellate cell activation, hepatic fibrous collagen and total collagen accumulation; liver disease of necro-inflammatory and/or of immunological origin; andurogenital system disorders, such as renal fibrosis and renal failure resulting from chronic kidney diseases or insufficiency (e.g. due to accumulation/deposition and tissue injury, progressive sclerosis, glomerunephritis); prostate hypertrophy; cardiac interstitial fibrosis, cardiac remodeling and fibrosis, heart failure, cardiorenal syndrome; cardiac hypertrophy; diabetic nephropathy
  b. sexual disorders of conditions: erectile dysfunction; female sexual dysfunction (e.g., female sexual arousal dysfunction), vaginal atrophy and incontinence.
  c. wound healing (e.g., in diabetics), microvascular perfusion improvement (e.g., following injury, in perioperative care), microcirculation abnormalities, control of vascular leakage and permeability, for conserving blood substitutes in trauma patients, endothelial dysfunction, inhibition of modulation of platelet aggregation, anal fissures; shock, sepsis, cardiogenic shock, control of leukocyte activation; diabetic ulcers In other embodiments of the invention, the compounds of Formula I and Formula Ib as well as pharmaceutically acceptable salts thereof are useful in the prevention and/or treatment of the following types of diseases, conditions and disorders which can benefit from sGC stimulation:
hypertension, resistant hypertension, diabetic hypertension, pulmonary hypertension (PH), pulmonary arterial hypertension, PH associated with COPD, acute respiratory distress syndrome, chronic airflow obstruction, asthma or pulmonary fibrosis, thrombosis, obstructive thromboanginosis, embolism, peripheral embolism, thromboembolic disorders, atherosclerosis, right heart hypertrophy, heart failure, diastolic dysfunction, systolic dysfunction, sleep apnea associated with heart failure, liver cirrhosis, renal fibrosis, renal failure resulting from chronic kidney diseases or insufficiency, metabolic disorder, dyslipidemia, hypercholesterolemia, hypertriglyceridemia, sitosterolemia, fatty liver disease, hepatitis, erectile dysfunction, female sexual dysfunction, female sexual arousal dysfunction, vaginal atrophy and wound healing.

The terms, "disease", "disorder" and "condition" may be used interchangeably here to refer to an sGC, cGMP and/or NO mediated medical or pathological condition.

As used herein, the terms "subject" and "patient" are used interchangeably. The terms "subject" and "patient" refer to an animal (e.g., a bird such as a chicken, quail or turkey, or a mammal), specifically a "mammal" including a non-primate (e.g., a cow, pig, horse, sheep, rabbit, guinea pig, rat, cat, dog, and mouse) and a primate (e.g., a monkey, chimpanzee and a human), and more specifically a human. In some embodiments, the subject is a non-human animal such as a farm animal (e.g., a horse, cow, pig or sheep), or a pet (e.g., a dog, cat, guinea pig or rabbit). In some embodiments, the subject is a human.

The invention also provides a method for treating one of the above diseases, conditions and disorders in a subject, comprising administering a therapeutically effective amount of a compound of Formula I and Formula Ib, or a pharmaceutically acceptable salt thereof, to the subject in need of the treatment. Alternatively, the invention provides the use of a compound of Formula I and Formula Ib, or a pharmaceutically acceptable salt thereof, in the treatment of one of these diseases, conditions and disorders in a subject in need of the treatment. The invention further provides a method of making or manufacturing a medicament useful for treating one of these diseases, conditions and disorders comprising using a compound of Formula I and Formula Ib, or a pharmaceutically acceptable salt thereof.

The term "biological sample", as used herein, refers to an in vitro or ex vivo sample, and includes, without limitation, cell cultures or extracts thereof; biopsied material obtained from a mammal or extracts thereof; blood, saliva, urine, faeces, semen, tears, lymphatic fluid, ocular fluid, vitreous humour, or other body fluids or extracts thereof.

"Treat", "treating" or "treatment" with regard to a disorder or disease refers to alleviating or abrogating the cause and/or the effects of the disorder or disease. As used herein, the terms "treat", "treatment" and "treating" refer to the reduction or amelioration of the progression, severity and/or duration of an sGC, cGMP and/or NO mediated condition, or the amelioration of one or more symptoms (preferably, one or more discernable symptoms) of said condition (i.e. "managing" without "curing" the condition), resulting from the administration of one or more therapies (e.g., one or more therapeutic agents such as a compound or composition of the invention). In specific embodiments, the terms "treat"; "treatment" and "treating" refer to the amelioration of at least one measurable physical parameter of an sGC, cGMP and/or NO mediated condition. In other embodiments the terms "treat", "treatment" and "treating" refer to the inhibition of the progression of an sGC, cGMP and/or NO mediated condition, either physically by, e.g., stabilization of a discernable symptom or physiologically by, e.g., stabilization of a physical parameter, or both.

The term "preventing" as used herein refers to administering a medicament beforehand to avert or forestall the appearance of one or more symptoms of a disease or disorder. The person of ordinary skill in the medical art recognizes that the term "prevent" is not an absolute term. In the medical art it is understood to refer to the prophylactic administration of a drug to substantially diminish the likelihood or seriousness of a condition, or symptom of the condition and this is the sense intended in this disclosure. The Physician's Desk Reference, a standard text in the field, uses the term "prevent" hundreds of times. As used therein, the terms "prevent", "preventing" and "prevention" with regard to a disorder or disease, refer to averting the cause, effects, symptoms or progression of a disease or disorder prior to the disease or disorder fully manifesting itself.

In one embodiment, the methods of the invention are a preventative or "pre-emptive" measure to a patient, specifically a human, having a predisposition (e.g. a genetic predisposition) to developing an sGC, cGMP and/or NO related disease, disorder or symptom.

In other embodiments, the methods of the invention are a preventative or "pre-emptive" measure to a patient, specifically a human, suffering from a disease, disorder or condition that makes him at risk of developing an sGC, cGMP or NO related disease, disorder or symptom.

The compounds and pharmaceutical compositions described herein can be used alone or in combination therapy for the treatment or prevention of a disease or disorder mediated, regulated or influenced by sGC, cGMP and/or NO.

Compounds and compositions here disclosed are also useful for veterinary treatment of companion animals, exotic animals and farm animals, including, without limitation, dogs, cats, mice, rats, hamsters, gerbils, guinea pigs, rabbits, horses, pigs and cattle.

In other embodiments, the invention provides a method of stimulating sGC activity in a biological sample, comprising contacting said biological sample with a compound or composition of the invention. Use of a sGC stimulator in a biological sample is useful for a variety of purposes known to one of skill in the art. Examples of such purposes include, without limitation, biological assays and biological specimen storage.

Combination Therapies

The compounds and pharmaceutical compositions described herein can be used in combination therapy with one or more additional therapeutic agents. For combination treatment with more than one active agent, where the active agents are in separate dosage formulations, the active agents may be administered separately or in conjunction. In addition, the administration of one element may be prior to, concurrent to, or subsequent to the administration of the other agent.

When co-administered with other agents, e.g., when co-administered with another pain medication, an "effective amount" of the second agent will depend on the type of drug used. Suitable dosages are known for approved agents and can be adjusted by the skilled artisan according to the condition of the subject, the type of condition(s) being treated and the amount of a compound described herein being used. In cases where no amount is expressly noted, an effective amount should be assumed. For example, compounds described herein can be administered to a subject in a dosage range from between about 0.01 to about 10,000 mg/kg body weight/day, about 0.01 to about 5000 mg/kg body weight/day, about 0.01 to about 3000 mg/kg body weight/day, about 0.01 to about 1000 mg/kg body weight/day, about 0.01 to about 500 mg/kg body weight/day, about 0.01 to about 300 mg/kg body weight/day, about 0.01 to about 100 mg/kg body weight/day.

When "combination therapy" is employed, an effective amount can be achieved using a first amount of a compound of Formula I and Formula Ib or a pharmaceutically acceptable salt thereof and a second amount of an additional suitable therapeutic agent.

In one embodiment of this invention, a compound of Formula I and Formula Ib and the additional therapeutic agent are each administered in an effective amount (i.e., each in an amount which would be therapeutically effective if administered alone). In another embodiment, the compound of Formula I and Formula Ib and the additional therapeutic agent are each administered in an amount which alone does not provide a therapeutic effect (a sub-therapeutic dose). In yet another embodiment, the compound of Formula I and Formula Ib can be administered in an effective amount, while the additional therapeutic agent is administered in a sub-therapeutic dose. In still another embodiment, the compound of Formula I and Formula Ib can be administered in a sub-therapeutic dose, while the additional therapeutic agent, for example, a suitable cancer-therapeutic agent is administered in an effective amount.

As used herein, the terms "in combination" or "co-administration" can be used interchangeably to refer to the use of more than one therapy (e.g., one or more prophylactic and/or therapeutic agents). The use of the terms does not restrict the order in which therapies (e.g., prophylactic and/or therapeutic agents) are administered to a subject.

Co-administration encompasses administration of the first and second amounts of the compounds in an essentially simultaneous manner, such as in a single pharmaceutical composition, for example, capsule or tablet having a fixed ratio of first and second amounts, or in multiple, separate capsules or tablets for each. In addition, such co administration also encompasses use of each compound in a sequential manner in either order. When co-administration involves the separate administration of the first amount of a compound of Formula I and Formula Ib and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Formula I and Formula Ib and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound described herein) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

Examples of other therapeutic agents that may be combined with a compound of this disclosure, either administered separately or in the same pharmaceutical composition, include, but are not limited to:

(1) Endothelium-derived releasing factor (EDRF);
(2) NO donors such as a nitrosothiol, a nitrite, a sydnonimine, a NONOate, a N-nitrosoamine, a N-hydroxyl nitrosamine, a nitrosimine, nitrotyrosine, a diazetine dioxide, an oxatriazole 5-imine, an oxime, a hydroxylamine, a N-hydroxyguanidine, a hydroxyurea or a furoxan. Some examples of these types of compounds include: glyceryl trinitrate (also known as GTN, nitroglycerin, nitroglycerine, and trinitrogylcerin), the nitrate ester of glycerol; sodium nitroprusside (SNP), wherein a molecule of nitric oxide is coordinated to iron metal forming a square bipyramidal complex; 3-morpholinosydnonimine (SIN-1), a zwitterionic compound formed by combination of a morpholine and a sydnonimine; S-nitroso-N-acetylpenicillamine (SNAP), an N-acetylated amino acid derivative with a nitrosothiol functional group; diethylenetriamine/NO (DETA/NO), a compound of nitric oxide covalently linked to diethylenetriamine; and NCX 4016, an m-nitroxymethyl phenyl ester of acetyl salicylic acid. More specific examples of some of these classes of NO donors include: the classic nitrovasodilators, such as organic nitrate and nitrite esters, including nitroglycerin, amyl nitrite, isosorbide dinitrate, isosorbide 5-mononitrate, and nicorandil; Isosorbide (Dilatrate®-SR, Imdur®, Ismo®, Isordil®, Isordil®, Titradose®, Monoket®), FK 409 (NOR-3); FR 144420 (NOR-4); 3-morpholinosydnonimine; Linsidomine chlorohydrate ("SIN-1"); S-nitroso-N-acetylpenicillamine ("SNAP"); AZD3582 (CI-NOD lead compound), NCX 4016, NCX 701, NCX 1022, HCT 1026, NCX 1015, NCX 950, NCX 1000, NCX 1020, AZD 4717, NCX 1510/NCX 1512, NCX 2216, and NCX 4040 (all available from NicOx S.A.), S-nitrosoglutathione (GSNO), Sodium Nitroprusside, S-nitrosoglutathione mono-ethyl-ester (GSNO-ester), 6-(2-hydroxy-1-methyl-nitrosohydrazino)-N-methyl-1-hexanamine (NOC-9) or diethylamine NONOate. Nitric oxide donors are also as disclosed in U.S. Pat. Nos. 5,155,137, 5,366,997, 5,405,919, 5,650, 442, 5,700,830, 5,632,981, 6,290,981, 5,691,423 5,721,365, 5,714,511, 6,511,911, and 5,814,666, Chrysselis et al. (2002) J Med Chem. 45:5406-9 (such as NO donors 14 and 17), and Nitric Oxide Donors for Pharmaceutical and Biological Research, Eds: Peng George Wang, Tingwei Bill Cai, Naoyuki Taniguchi, Wiley, 2005;

(3) Other substances that enhance cGMP concentrations such as protoporphyrin IX, arachidonic acid and phenyl hydrazine derivatives;

(4) Nitric Oxide Synthase substrates: for example, n-hydroxyguanidine based analogs, such as N[G]-hydroxy-L-arginine (NOHA), 1-(3,4-dimethoxy-2-chlorobenzylideneamino)-3-hydroxyguanidine, and PR5 (1-(3,4-dimethoxy-2-chlorobenzylideneamino)-3-hydroxyguanidine); L-arginine derivatives (such as homo-Arg, homo-NOHA, N-tert-butyloxy- and N-(3-methyl-2-butenyl)oxy-L-arginine, canavanine, epsilon guanidine-carpoic acid, agmatine, hydroxylagmatine, and L-tyrosyl-L-arginine); N-alkyl-N'-hydroxyguanidines (such as N-cyclopropyl-N'-hydroxyguanidine and N-butyl-N'-hydroxyguanidine), N-aryl-N'-hydroxyguanidines (such as N-phenyl-N'-hydroxyguanidine and its para-substituted derivatives which bear —F, —Cl, -methyl, —OH substituents, respectively); guanidine derivatives such as 3-(trifluormethyl) propylguanidine; and others reviewed in Cali et al. (2005, Current Topics in Medicinal Chemistry 5:721-736) and disclosed in the references cited therein;

(5) Compounds which enhance eNOS transcription: for example those described in WO 02/064146, WO 02/064545, WO 02/064546 and WO 02/064565, and corresponding patent documents such as US2003/0008915, US2003/0022935, US2003/0022939 and US2003/0055093. Other eNOS transcriptional enhancers including those described in US20050101599 (e.g. 2,2-difluorobenzo[1,3]dioxol-5-carboxylic acid indan-2-ylamide, and 4-fluoro-N-(indan-2-yl)-benzamide), and Sanofi-Aventis compounds AVE3085 and AVE9488 (CA Registry NO. 916514-70-0; Schäfer et al., Journal of Thrombosis and Homeostasis 2005; Volume 3, Supplement 1: abstract number P1487);

(6) NO independent heme-independent sGC activators, including, but not limited to: BAY 58-2667 (see patent publication DE19943635)

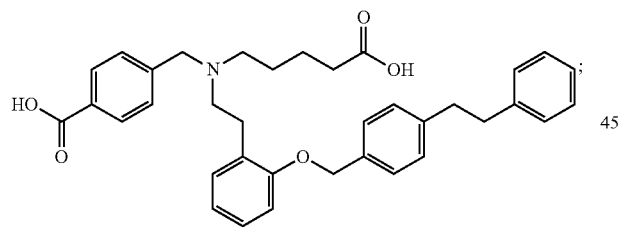

HMR-1766 (ataciguat sodium, see patent publication WO2000002851)

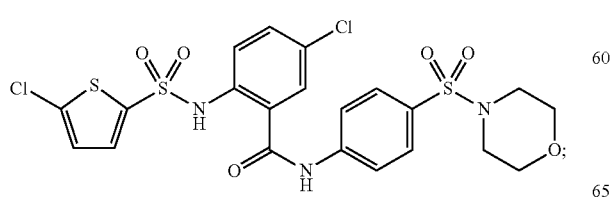

S 3448 (2-(4-chloro-phenylsulfonylamino)-4,5-dimethoxy-N-(4-(thiomorpholine-4-sulfonyl)-phenyl)-benzamide (see patent publications DE19830430 and WO2000002851)

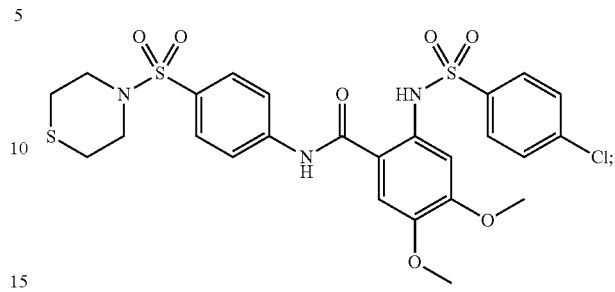

and
HMR-1069 (Sanofi-Aventis).

(7) Heme-dependent sGC stimulators including, but not limited to:

YC-1 (see patent publications EP667345 and DE19744026)

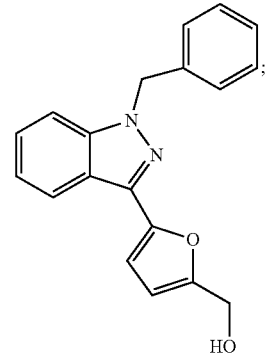 [SMILES: OCc1ccc(-c2nn(Cc3ccccc3)c3ccccc23)o1]

BAY 41-2272 (see patent publications DE19834047 and DE19942809)

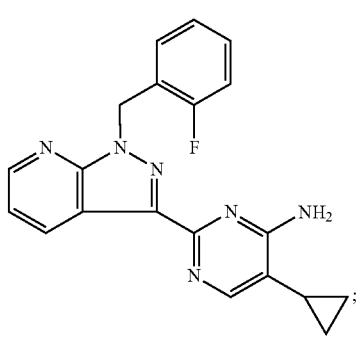 [SMILES: Nc1nc(-c2nn(Cc3ccccc3F)c3ncccc23)ncc1C1CC1]

BAY 41-8543 (see patent publication DE19834044)

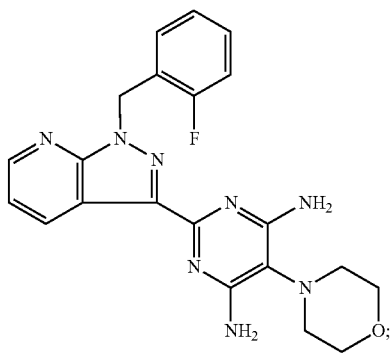 [SMILES: Nc1nc(-c2nn(Cc3ccccc3F)c3ncccc23)nc(N)c1N1CCOCC1]

BAY 63-2521 (see patent publication DE19834044)
CFM-1571 (see patent publication WO2000027394)

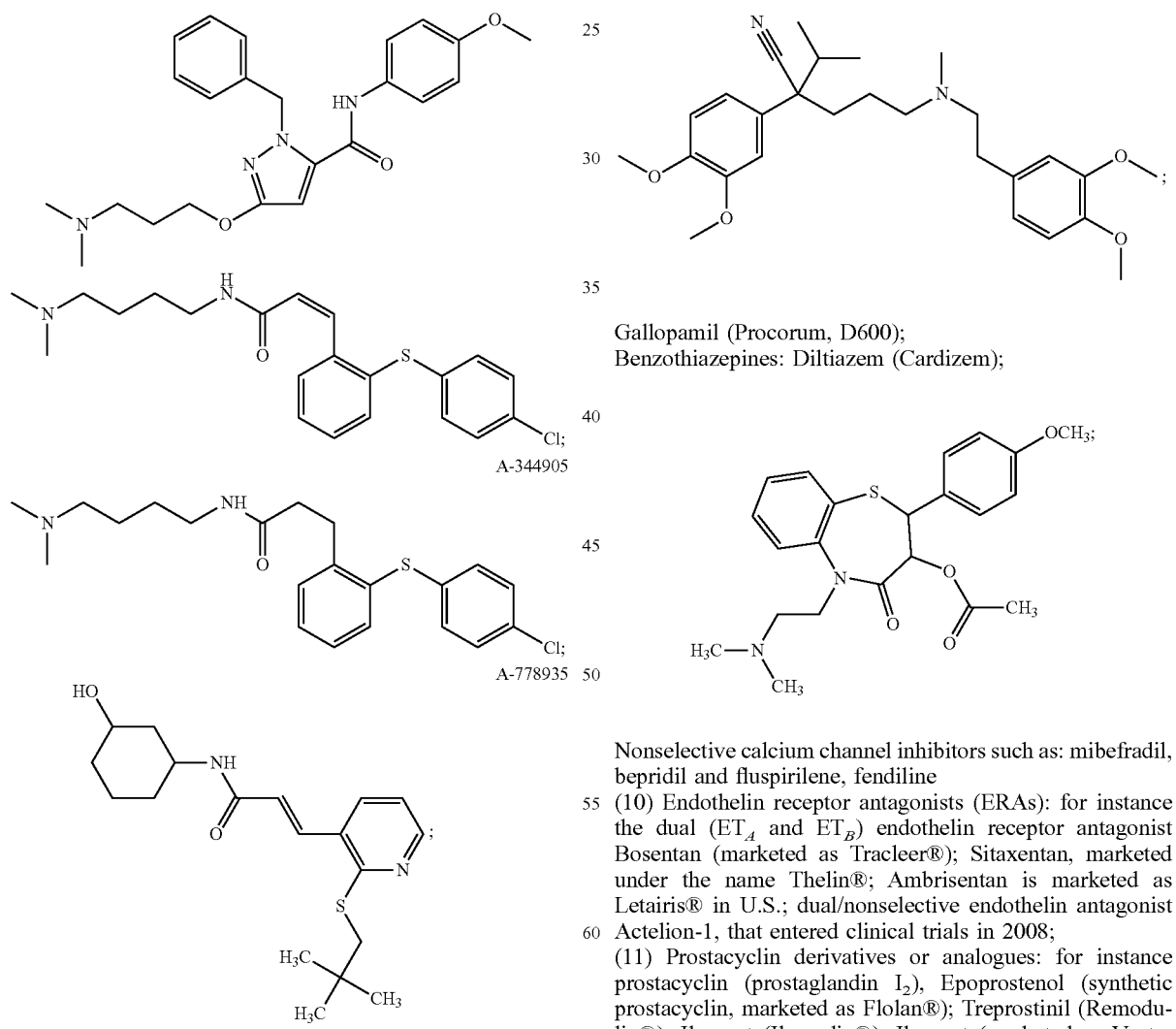

and other compounds disclosed in Tetrahedron Letters (2003), 44(48): 8661-8663.

(8) Compounds that inhibit the degradation of cGMP, such as:
PDE5 inhibitors, such as, for example, Sildenafil (Viagra®) and other related agents such as Avanafil, Lodenafil, Mirodenafil, Sildenafil citrate (Revatio®), Tadalafil (Cialis® or Adcirca®), Vardenafil (Levitra®) and Udenafil; Alprostadil; and Dipyridamole;

(9) Calcium channel blockers such as:
Dihydropyridine calcium channel blockers: Amlodipine (Norvasc), Aranidipine (Sapresta), Azelnidipine (Calblock), Barnidipine (HypoCa), Benidipine (Coniel), Cilnidipine (Atelec, Cinalong, Siscard), Clevidipine (Cleviprex), Diltiazem, Efonidipine (Landel), Felodipine (Plendil), Lacidipine (Motens, Lacipil), Lercanidipine (Zanidip), Manidipine (Calslot, Madipine), Nicardipine (Cardene, Carden SR), Nifedipine (Procardia, Adalat), Nilvadipine (Nivadil), Nimodipine (Nimotop), Nisoldipine (Baymycard, Sular, Syscor), Nitrendipine (Cardif, Nitrepin, Baylotensin), Pranidipine (Acalas), Isradipine (Lomir);
Phenylalkylamine calcium channel blockers: Verapamil (Calan, Isoptin)

Gallopamil (Procorum, D600);
Benzothiazepines: Diltiazem (Cardizem);

Nonselective calcium channel inhibitors such as: mibefradil, bepridil and fluspirilene, fendiline
(10) Endothelin receptor antagonists (ERAs): for instance the dual ($ET_A$ and $ET_B$) endothelin receptor antagonist Bosentan (marketed as Tracleer®); Sitaxentan, marketed under the name Thelin®; Ambrisentan is marketed as Letairis® in U.S.; dual/nonselective endothelin antagonist Actelion-1, that entered clinical trials in 2008;
(11) Prostacyclin derivatives or analogues: for instance prostacyclin (prostaglandin $I_2$), Epoprostenol (synthetic prostacyclin, marketed as Flolan®); Treprostinil (Remodulin®), Iloprost (Ilomedin®), Iloprost (marketed as Ventavis®); oral and inhaled forms of Remodulin® that are under development; Beraprost, an oral prostanoid available in Japan and South Korea;

(12) Antihyperlipidemics such as: bile acid sequestrants (e.g., Cholestyramine, Colestipol, Colestilan and Colesevelam); statins such as Atorvastatin, Simvastatin, Lovastatin, Fluvastatin, Pitavastatin, Rosuvastatin and Pravastatin; cholesterol absorption inhibitors such as Ezetimibe; other lipid lowering agents such as Icosapent ethyl ester, Omega-3-acid ethyl esters, Reducol; fibric acid derivatives such as Clofibrate, Bezafibrate, Clinofibrate, Gemfibrozil, Ronifibrate, Binifibrate, Fenofirate, Ciprofibrate, Choline fenofibrate; nicotinic acid derivatives such as Acipimox and Niacin; also combinations of statins, niacin, intestinal cholesterol absorption-inhibiting supplements (ezetimibe and others) and fibrates; antiplatelet therapies such as Clopidogrel bisulfate;

(13) Anticoagulants, such as the following types:

Coumarines (Vitamin K antagonists): Warfarin® (Coumadin) mostly used in the US and UK; Acenocoumarol® and Phenprocoumon®, mainly used in other countries; Phenindione®;

Heparin and derivative substances such as: Heparin; low molecular weight heparin, Fondaparinux and Idraparinux;

Direct thrombin inhibitors such as: Argatroban, Lepirudin, Bivalirudin and Dabigatran; Ximelagatran (Exanta®), not approved in the US;

Tissue plasminogen activators, used to dissolve clots and unblock arteries, such as Alteplase;

(14) Antiplatelet drugs: for instance thienopyridines such as Lopidogrel and Ticlopidine; Dipyridamole; Aspirin;

(15) ACE inhibitors, for example the following types:

Sulfhydryl-containing agents such as Captopril (trade name Capoten®), the first ACE inhibitor and Zofenopril;

Dicarboxylate-containing agents such as Enalapril (Vasotec/Renitec®); Ramipril (Altace/Tritace/Ramace/Ramiwin®); Quinapril (Accupril®), Perindopril (Coversyl/Aceon®); Lisinopril (Lisodur/Lopril/Novatec/Prinivil/Zestril®) and Benazepril (Lotensin®);

Phosphonate-containing agents such as: Fosinopril;

Naturally occurring ACE inhibitors such as: Casokinins and lactokinins, which are breakdown products of casein and whey that occur naturally after ingestion of milk products, especially cultured milk; The Lactotripeptides Val-Pro-Pro and Ile-Pro-Pro produced by the probiotic *Lactobacillus helveticus* or derived from casein also have ACE-inhibiting and antihypertensive functions;

Other ACE inhibitors such as Alacepril, Delapril, Cilazapril, Imidapril, Trandolapril, Temocapril, Moexipril, Spirapril,

(16) Supplemental oxygen therapy;

(17) Beta blockers, such as the following types:

Non-selective agents: Alprenolol®, Bucindolol®, Carteolol®, Carvedilol® (has additional α-blocking activity), Labetalol® (has additional α-blocking activity), Nadolol®, Penbutolol® (has intrinsic sympathomimetic activity), Pindolol® (has intrinsic sympathomimetic activity), Oxprenonol, Acebutolol, Sotalol, Mepindolol, Celiprolol, Arotinolol, Tertatolol, Amosulalol, Nipradilol, Propranolol® and Timolol®;

$β_1$-Selective agents: Acebutolol® (has intrinsic sympathomimetic activity), Atenolol®, Betaxolol®, Bisoprolol®, Celiprolol®, Dobutamine hydrochloride, Irsogladine maleate, Carvedilol, Talinolol, Esmolol®, Metoprolol® and Nebivolol®;

$β_2$-Selective agents: Butaxamine® (weak α-adrenergic agonist activity);

(18) Antiarrhythmic agents such as the following types:

Type I (sodium channel blockers): Quinidine, Lidocaine, Phenytoin, Propafenone

Type III (potassium channel blockers): Amiodarone, Dofetilide, Sotalol

Type V: Adenosine, Digoxin

(19) Diuretics such as: Thiazide diuretics, e.g., Chlorothiazide, Chlorthalidone, and Hydrochlorothiazide, Bendroflumethiazide, Cyclopenthiazide, Methyclothiazide, Polythiazide, Quinethazone, Xipamide, Metolazone, Indapamide, Cicletanine; Loop diuretics, such as Furosemide and Toresamide; potassium-sparing diuretics such as Amiloride, Spironolactone, Canrenoate potassium, Eplerenone and Triamterene; combinations of these agents; other diuretics such as Acetazolamid and Carperitide (20a) Direct acting vasodilators such as Hydralazine hydrochloride, Diazoxide, Sodium nitroprusside, Cadralazine; other vasodilators such as Isosorbide dinitrate and Isosorbide 5-mononitrate;

(20b) Exogenous vasodilators such as:

Adenocard®, an adenosine agonist, primarily used as an anti-arrhythmic;

Alpha blockers (which block the vasoconstricting effect of adrenaline):

Alpha-1-adrenoceptor antagonists such as Prazosin, Indoramin, Urapidil, Bunazosin, Terazosin, Doxazosin Atrial natriuretic peptide (ANP);

Ethanol;

Histamine-inducers, which complement proteins C3a, C4a and C5a work by triggering histamine release from mast cells and basophil granulocytes;

Tetrahydrocannabinol (THC), major active chemical in marijuana which has minor vasodilatory effects;

Papaverine, an alkaloid found in the opium poppy *papaver somniferum*; b

(21) Bronchodilators: there are two major types of bronchodilator, $β_2$ agonists and anticholinergics, exemplified below:

$β_2$ agonists: Salbutamol® or albuterol (common brand name: Ventolin) and Terbutaline® are short acting $β_2$ agonists for rapid relief of COPD symptoms. Long acting $β_2$ agonists (LABAs) such as Salmeterol® and Formoterol®;

anticholinergics: Ipratropium® is the most widely prescribed short acting anticholinergic drug. Tiotropium® is the most commonly prescribed long-acting anticholinergic drug in COPD;

Theophylline®, a bronchodilator and phosphodiesterase inhibitor;

(22) Corticosteroids: such as beclomethasone, methylprednisolone, betamethasone, prednisone, prenisolone, triamcinolone, dexamethasone, fluticasone, flunisolide and hydrocortisone, and corticosteroid analogs such as budesonide

(23) Dietary supplements such as, for example: omega-3 oils; folid acid, niacin, zinc, copper, Korean red ginseng root, ginkgo, pine bark, *Tribulus terrestris*, arginine, *Avena sativa*, horny goat weed, maca root, muira puama, saw palmetto, and Swedish flower pollen; Vitamin C, Vitamin E, Vitamin K2; Testosterone supplements, Testosterone transdermal patch; Zoraxel, Naltrexone, Bremelanotide (formerly PT-141), Melanotan II, hMaxi-K; Prelox: a Proprietary mix/combination of naturally occurring ingredients, L-arginine aspartate and Pycnogenol;

(24) PGD2 receptor antagonists including, but not limited to, compounds described as having PGD2 antagonizing activity in United States Published Applications US20020022218, US20010051624, and US20030055077, PCT Published Applications WO9700853, WO9825919, WO003066046, WO03066047, WO003101961, WO003101981, WO04007451, WO0178697, WO004032848, WO03097042, WO003097598, WO003022814, WO03022813, and WO04058164, European Patent Applications EP945450 and EP944614, and those listed in: Torisu et al. 2004 *Bioorg Med Chem Lett* 14:4557, Torisu et al. 2004 *Bioorg Med Chem Lett* 2004 14:4891, and Torisu et al. 2004 *Bioorg & Med Chem* 2004 12:4685;

(25) Immunosuppressants such as cyclosporine (cyclosporine A, Sandimmune® Neoral®), tacrolimus (FK-506, Prograf®), rapamycin (sirolimus, Rapamune®) and other FK-506 type immunosuppressants, and mycophenolate, e.g., mycophenolate mofetil (CellCept®);

(26) Non-steroidal anti-asthmatics such as β2-agonists (e.g., terbutaline, metaproterenol, fenoterol, isoetharine, albuterol, salmeterol, bitolterol and pirbuterol) and β2-agonist-corticosteroid combinations (e.g., salmeterol-fluticasone (Advair®), formoterol-budesonid (Symbicort®)), theophylline, cromolyn, cromolyn sodium, nedocromil, atropine, ipratropium, ipratropium bromide, leukotriene biosynthesis inhibitors (zileuton, BAY1005);

(27) Non-steroidal anti-inflammatory agents (NSAIDs) such as propionic acid derivatives (e.g., alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid and tioxaprofen), acetic acid derivatives (e.g., indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin and zomepirac), fenamic acid derivatives (e.g., flufenamic acid, meclofenamic acid, mefenamic acid, niflumic acid and tolfenamic acid), biphenylcarboxylic acid derivatives (e.g., diflunisal and flufenisal), oxicams (e.g., isoxicam, piroxicam, sudoxicam and tenoxican), salicylates (e.g., acetyl salicylic acid and sulfasalazine) and the pyrazolones (e.g., apazone, bezpiperylon, feprazone, mofebutazone, oxyphenbutazone and phenylbutazone);

(28) Cyclooxygenase-2 (COX-2) inhibitors such as celecoxib (Celebrex®), rofecoxib (Vioxx®), valdecoxib, etoricoxib, parecoxib and lumiracoxib;

(opioid analgesics such as codeine, fentanyl, hydromorphone, levorphanol, meperidine, methadone, morphine, oxycodone, oxymorphone, propoxyphene, buprenorphine, butorphanol, dezocine, nalbuphine and pentazocine; and

(29) Anti-diabetic agents such as insulin and insulin mimetics, sulfonylureas (e.g., Glyburide, Glybenclamide, Glipizide, Gliclazide, Gliquidone, Glimepiride, Meglinatide, Tolbutamide, Chlorpropamide, Acetohexamide, Tolazamide), biguanides, e.g., metformin (Glucophage®), α-glucosidase inhibitors (such as Acarbose, Epalrestat, Voglibose, Miglitol), thiazolidinone compounds, e.g., rosiglitazone (Avandia®), troglitazone (Rezulin®), ciglitazone, pioglitazone (Actos®) and englitazone; insulin sensitizers such as Pioglitazone and Rosiglitazone; Insulin secretagogues such as Repaglinide, Nateglinide and Mitiglinide; Incretin mimetics such as Exanatide and Liraglutide; Amylin analogues such as Pramlintide; glucose lowering agents such as Chromiumm picolinate (optinally combined with biotin); dipeptidyl peptidase IV inhibitors such as Sitagliptin, Vildagliptin, Saxagliptin, Alogliptin and Linagliptin; vaccines currently being developed for the treatment of diabetes; AVE-0277, Alum-GAD, BHT-3021, IBC-VS01; cytokine targeted therapies in development for the treatment of diabetes such as Anakinra, Canakinumab, Diacerein, Gevokizumab, LY-2189102, MABP-1, GIT-027; drugs in development for the treatment of diabetes:

| Drugs in development for the treatment of diabetes | | | |
|---|---|---|---|
| Drug Name | Organization | Mechanism of Action | Status |
| Dapagliflozin | AstraZeneca/Bristol-Myers Squibb | SGLT-2 Inhibitors | Recommended Approval |
| Alogliptin benzoate/metformin hydrochloride | Takeda | Insulin Sensitizers/Dipeptidyl Peptidase IV (CD26; DPP-IV; DP-IV) Inhibitors | Pre-Registered |
| Anagliptin | Kowa/Sanwa | Dipeptidyl Peptidase IV (CD26; DPP-IV; DP-IV) Inhibitors | Pre-Registered |
| Insulin degludec | Novo Nordisk | | Pre-Registered |
| Insulin degludec/insulin aspart | Novo Nordisk | | Pre-Registered |
| Insulin human (rDNA origin) inhalation powder | MannKind | | Pre-Registered |
| Lixisenatide | Sanofi | Insulin Secretagogues/GLP-1 Receptor Agonists | Pre-Registered |
| Recombinant human insulin | Biodel | | Pre-Registered |
| Teneligliptin | Mitsubishi Tanabe Pharma | Dipeptidyl Peptidase IV (CD26; DPP-IV; DP-IV) Inhibitors | Pre-Registered |
| AVE-0277 | Andromeda Biotech/Teva | | Phase III |
| Albiglutide | GlaxoSmithKline | GLP-1 Receptor Agonists | Phase III |
| Aleglitazar | Roche | PPARalpha Agonists/PPARgamma Agonists | Phase III |
| Atorvastatin calcium/glimepiride | GlaxoSmithKline | K(ATP) Channel Blockers/Dipeptidyl Peptidase IV (CD26; DPP-IV; DP-IV) Inhibitors/HMG-CoA Reductase Inhibitors/ | Phase III |

| Drugs in development for the treatment of diabetes | | | |
|---|---|---|---|
| Drug Name | Organization | Mechanism of Action | Status |
| BYK-324677 | Nycomed | TNFSF6 Expression Inhibitors | Phase III |
| Balaglitazone | Dr. Reddy's Laboratories | Insulin Sensitizers/ PPARgamma Partial Agonists | Phase III |
| CSG-452 | Chugai Pharmaceutical | SGLT-2 Inhibitors | Phase III |
| Canagliflozin | Johnson & Johnson/ Mitsubishi Tanabe Pharma | SGLT-2 Inhibitors | Phase III |
| Canagliflozin/metformin hydrochloride | Johnson & Johnson | SGLT-2 Inhibitors/ Insulin Sensitizers | Phase III |
| Dapagliflozin/Metformin hydrochloride | AstraZeneca/Bristol-Myers Squibb | SGLT-2 Inhibitors/ Insulin Sensitizers | Phase III |
| Dulaglutide | Lilly | Insulin Secretagogues/GLP-1 Receptor Agonists | Phase III |
| Empagliflozin | Boehringer Ingelheim/ Lilly | SGLT-2 Inhibitors | Phase III |
| Empagliflozin/linagliptin | Boehringer Ingelheim/ Lilly | SGLT-2 Inhibitors/ Dipeptidyl Peptidase IV (CD26; DPP-IV; DP-IV) Inhibitors | Phase III |
| Gemigliptin | LG Life Sciences | Dipeptidyl Peptidase IV (CD26; DPP-IV; DP-IV) Inhibitors | Phase III |
| Hepatic-directed vesicle insulin | Diasome Pharmaceuticals | | Phase III |
| Human isophane insulin | Wockhardt | | Phase III |
| IN-105 | Biocon | | Phase III |
| Insulin degludec/liraglutide | Novo Nordisk | Insulin Secretagogues/GLP-1 Receptor Agonists | Phase III |
| Insulin glargine | Sanofi | | Phase III |
| Ipragliflozin L-proline | Astellas Pharma/ Kotobuki | SGLT-2 Inhibitors | Phase III |
| LY-2605541 | Lilly | | Phase III |
| LY-2963016 | Lilly | | Phase III |
| Lixisenatide/Insulin glargine | Sanofi | Insulin Secretagogues/GLP-1 Receptor Agonists | Phase III |
| Lobeglitazone sulfate | Chong Kun Dang Pharm (CKD Pharm) | PPARalpha Agonists/ PPARgamma Agonists/Insulin Sensitizers | Phase III |
| Luseogliflozin | Taisho | SGLT-2 Inhibitors | Phase III |
| Otelixizumab | Tolerx | Anti-CD3 | Phase III |
| Ranolazine | Gilead | Sodium Channel Blockers | Phase III |
| Recombinant human insulin | National Institute of Health Sciences | | Phase III |
| Sitagliptin phosphate monohydrate/pioglitazone hydrochloride | Merck & Co. | PPARgamma Agonists/Insulin Sensitizers/ Dipeptidyl Peptidase IV (CD26; DPP-IV; DP-IV) Inhibitors | Phase III |
| Sitagliptin/atorvastatin calcium | Merck & Co. | Dipeptidyl Peptidase IV (CD26; DPP-IV; DP-IV) Inhibitors/ HMG-CoA Reductase Inhibitors/TNFSF6 Expression Inhibitors | Phase III |
| TAK-875 | Takeda | Free Fatty Acid Receptor 1 (FFAR1; GPR40) Agonists/ Insulin Secretagogues | Phase III |
| TT-401 | 7TM Pharma | Cannabinoid CB1 Antagonists | Phase I |
| TT-401 | Transition Therapeutics | | Phase I |

Drugs in development for the treatment of diabetes

| Drug Name | Organization | Mechanism of Action | Status |
|---|---|---|---|
| ZYH-2 | Cadila Healthcare (d/b/a Zydus Cadila) | PPARalpha Ligands/ PPARgamma Ligands | Phase I |
| ZYO-1 | Cadila Healthcare (d/b/a Zydus Cadila) | Cannabinoid CB1 Antagonists | Phase I |
| 701645 | Cellonis Biotechnologies | | Phase I |
| 701499 | Cellonis Biotechnologies | | Phase I |
| 743300 | University of California, San Francisco | | Phase I |
| 448661 | University of Pittsburgh | | Phase I |
| AD-1 | National Institute Pharma Res Dev | | Clinical |
| Colesevelam hydrochloride | Daiichi Sankyo | Bile Acid Sequestrants | Clinical |
| DBPR-108 | National Health Research Institutes/ ScinoPharm | | IND Filed |
| Nodlin | Biolaxy | | IND Filed |
| PSN-491 | Prosidion | Glucose-Dependent Insulinotropic Receptor (GDIR, GPR119) Agonists/ Dipeptidyl Peptidase IV (CD26; DPP-IV; DP-IV) Inhibitors | IND Filed |
| Tolimidone | Melior Discovery | Lyn Kinase Activators | IND Filed |
| ZYD-1 | Cadila Healthcare (d/b/a Zydus Cadila) | GLP-1 Receptor Agonists | IND Filed |
| ZYOG-1 | Cadila Healthcare (d/b/a Zydus Cadila) | GLP-1 Receptor Agonists | IND Filed |

(30) HDL cholesterol-increasing agents such as Anacetrapib, MK-524A, CER-001, DRL-17822, Dalcetrapib, JTT-302, RVX-000222, TA-8995;

(31) Antiobesity drugs such as Methamphetamine hydrochloride, Amfepramone hydrochloride (Tenuate®), Phentermine (Ionamin®), Benzfetamine hydrochloride (Didrex®), Phendimetrazine tartrate (Bontril®, Prelu-2 ®, Plegine®), Mazindol (Sanorex®), Orlistat (Xenical®), Sibutramine hydrochloride monohydrate (Meridia®, Reductil®), Rimonabant (Acomplia®), Amfepramone, Chromium picolinate, RM-493, TZP-301; combination such as Phentermine/Topiramate, Bupropion/Naltrexone, Sibutramine/Metformin, Bupropion SR/Zonisamide SR, Salmeterol, xinafoate/fluticasone propionate; Lorcaserin hydrochloride, Phentermine/topiramate, Bupropion/naltrexone, Cetilistat, Exenatide, KI-0803, Liraglutide, Metformin hydrochloride, Sibutramine/Metformin, 876167, ALS-L-1023, Bupropion SR/Zonisamide SR, CORT-108297, Canagliflozin, Chromium picolinate, GSK-1521498, LY-377604, Metreleptin, Obinepitide, P-57AS3, PSN-821, Salmeterol xinafoate/fluticasone propionate, Sodium tungstate, Somatropin (recombinant), TM-30339, TTP-435, Tesamorelin, Tesofensine, Velneperit, Zonisamide, BMS-830216, ALB-127158, AP-1030, ATHX-105, AZD-2820, AZD-8329, Beloranib hemioxalate, CP-404, HPP-404, ISIS-FGFR4Rx, Insulinotropin, KD-3010PF, 05212389, PP-1420, PSN-842, Peptide YY3-36, Resveratrol, S-234462; S-234462, Sobetirome, TM-38837, Tetrahydrocannabivarin, ZYO-1, beta-Lapachone;

(32) Angiotensin receptor blockers such as Losartan, Valsartan, Candesartan cilexetil, Eprosaran, Irbesartan, Telmisartan, Olmesartran medoxomil, Azilsartan medoxomil;

(33) Renin inhibitors such as Aliskiren hemifumirate;

(34) Centrally acting alpha-2-adrenoceptor agonists such as Methyldopa, Clonidine, Guanfacine;

(35) Adrenergic neuron blockers such as Guanethidine, Guanadrel;

(36) Imidazoline I-1 receptor agonists such as Rimenidine dihydrogen phosphate and Moxonidine hydrochloride hydrate;

(37) Aldosterone antagonists such as Spironolactone and Eplerenone

(38) Potassium channel activators such as Pinacidil

(39) Dopamine D1 agonists such as Fenoldopam mesilate; Other dopamine agonists such as Ibopamine, Dopexamine and Docarpamine;

(40) 5-HT2 antagonists such as Ketanserin;

(41) Drugs that are currently being developed for the treatment of arterial hypertension:

| Drug Name | Organization | Mechanism of Action | Status |
|---|---|---|---|
| Azilsartan | Takeda | Angiotensin AT1 Antagonists/ Angiotensin AT2 | Registered |

| Drug Name | Organization | Mechanism of Action | Status |
|---|---|---|---|
| | | Antagonists/ Insulin Sensitizers | |
| Amlodipine besylate/irbesartan | Dainippon Sumitomo Pharma | Angiotensin AT1 Antagonists/ Calcium Channel Blockers | Pre-Registered |
| Azilsartan/amlodipine besilate | Takeda | Angiotensin AT1 Antagonists/ Insulin Sensitizers/ Calcium Channel Blockers | Phase III |
| Cilnidipine/valsartan | Ajinomoto/Mochida | Angiotensin AT1 Antagonists/ Calcium Channel Blockers | Phase III |
| Fimasartan | Boryung | Angiotensin AT1 Antagonists | Phase III |
| Irbesartan/atorvastatin | Hanmi | Angiotensin AT1 Antagonists/ Dipeptidyl Peptidase IV (CD26; DPP-IV; DP-IV) Inhibitors/HMG-CoA Reductase Inhibitors/ TNFSF6 Expression Inhibitors | Phase III |
| Irbesartan/trichlormethiazide | Shionogi | Angiotensin AT1 Antagonists | Phase III |
| Losartan potassium/hydrochlorothiazide/ amlodipine besylate | Merck & Co. | Angiotensin AT1 Antagonists/ Calcium Channel Blockers | Phase III |
| Pratosartan | Boryung | Angiotensin AT1 Antagonists | Phase III |
| ACT-280778 | Actelion | | Phase II |
| Amiloride hydrochloride/spironolactone | Hemodynamic Therapeutics | Mineralocorticoid Receptor (MR) Antagonists/ Na+/H+ Exchanger (NHE) Inhibitors/ Epithelial Sodium Channels (ENaC) Blockers/ K(V)1.5 Channel Blockers/ K(V)4.3 Channel Blockers | Phase II |
| Angiotensin vaccine/CoVaccine HT | BTG | | Phase II |
| CYT006-AngQb | Cytos Biotechnology | Anti-Angiotensin II | Phase II |
| Cholecalciferol | Emory University | | Phase II |
| Cobiprostone | Sucampo Pharmaceuticals | ClC-2 Channel Activators | Phase II |
| INT-001 | IntelGenx | | Phase II |
| LCZ-696 | Novartis | Angiotensin AT1 Antagonists/ Neprilysin (Enkephalinase, Neutral Endopeptidase, NEP) Inhibitors | Phase II |
| LFF-269 | Novartis | | Phase II |
| Octreotide acetate | Chiasma | Growth Hormone Release Inhibitors/ Somatostatin Agonists | Phase II |

| Drug Name | Organization | Mechanism of Action | Status |
|---|---|---|---|
| PL-3994 | Palatin Technologies | Atrial Natriuretic Peptide A (NPR1; Guanylate Cyclase A) Receptor Agonists | Phase II |
| Rostafuroxine | Sigma-Tau | | Phase II |
| SLx-2101 | NT Life Sciences | Phosphodiesterase V (PDE5A) Inhibitors | Phase II |
| TBC-3711 | Encysive Pharmaceuticals | Endothelin ETA Receptor Antagonists | Phase II |
| Udenafil | Dong-A/Falk Pharma | Phosphodiesterase V (PDE5A) Inhibitors | Phase II |
| Atorvastatin calcium/losartan potassium | HanAll BioPharma | Angiotensin AT1 Antagonists/ Dipeptidyl Peptidase IV (CD26; DPP-IV; DP-IV) Inhibitors/HMG-CoA Reductase Inhibitors/ TNFSF6 Expression Inhibitors | Phase I |
| BIA-5-1058 | BIAL | Dopamine beta-monooxygenase Inhibitors | Phase I |
| CS-3150 | Daiichi Sankyo | | Phase I |
| DSP-9599 | Dainippon Sumitomo Pharma | Renin Inhibitors | Phase I |
| MK-1597 | Actelion/Merck & Co. | Renin Inhibitors | Phase I |
| MK-4618 | Merck & Co. | | Phase I |
| MK-5478 | Merck & Co. | | Phase I |
| MK-7145 | Merck & Co. | | Phase I |
| MK-8266 | Merck & Co. | | Phase I |
| MK-8457 | Merck & Co. | | Phase I |
| MP-157 | Mitsubishi Tanabe Pharma | Angiotensin AT2 Agonists | Phase I |
| MT-3995 | Mitsubishi Tanabe Pharma | Mineralocorticoid Receptor (MR) Antagonists | Phase I |
| Mirodenafil hydrochloride | SK Chemicals | Phosphodiesterase V (PDE5A) Inhibitors | Phase I |
| NV-04 | Novogen | Antioxidants | Phase I |
| Nifedipine/Candesartan cilexetil | Bayer | Angiotensin AT1 Antagonists/ Calcium Channel Blockers/ Antioxidants | Phase I |
| QGC-001 | Quantum Genomics | Glutamyl Aminopeptidase (Aminopeptidase A) Inhibitors | Phase I |
| RDX-5791 | Ardelyx | Na+/H+ Exchanger type 3 (NHE-3) Inhibitors | Phase I |
| TAK-272 | Takeda | Renin Inhibitors | Phase I |
| TAK-591 | Takeda | Angiotensin AT2 Antagonists | Phase I |
| VTP-27999 | Vitae Pharmaceuticals | Renin Inhibitors | Phase I |
| Vasomera | PhaseBio | VPAC2 (VIP2) Agonists | Phase I |
| Tylerdipine hydrochloride | Sihuan Pharmaceutical | Calcium Channel Blockers | IND Filed |

(42) Vasopressin antagonists such as Tolvaptan;

(43) Calcium channel sensitizers such as Levosimendan or activators such as Nicorandil;

(44) PDE-3 inhibitors such as Amrinone, Milrinone, Enoximone, Vesnarinone, Pimobendan, Olprinone;

(45) Adenylate cyclase activators such as Colforsin dapropate hydrochloride;

(46) Positive inotropic agents such as Digoxin and Metildigoxin; metabolic cardiotonic agents such as Ubidecarenone; brain naturetic peptides such as Nesiritide;

(47) Drugs that are currently in development for the treatment of heart failure:

Drugs in development for the treatment of heart failure

| Drug Name | Organization | Mechanism of Action | Status |
|---|---|---|---|
| Bucindolol hydrochloride | ARCA | beta-Adrenoceptor Antagonists | Pre-Registered |
| Aliskiren hemifumarate | Novartis | Renin Inhibitors | Phase III |
| Ferric carboxymaltose | Vifor | | Phase III |
| LCZ-696 | Novartis | Angiotensin AT1 Antagonists/Neprilysin (Enkephalinase, Neutral Endopeptidase, NEP) Inhibitors | Phase III |
| Neuregulin-1 | Zensun | | Phase III |
| Olmesartan medoxomil | Tohoku University | Angiotensin AT1 Antagonists | Phase III |
| C3BS-CQR-1 | Cardio3 Bio-Sciences | | Phase II/III |
| MyOCell | Bioheart | | Phase II/III |
| Serelaxin | Novartis | | Phase II/III |
| AAV1/SERCA2a | AmpliPhi Biosciences/ Celladon/Mount Sinai School of Medicine | | Phase II |
| Albiglutide | GlaxoSmithKline | GLP-1 Receptor Agonists | Phase II |
| Allogeneic mesenchymal precursor cells | Mesoblast | | Phase II |
| AlsterMACS | Miltenyi Biotec | | Phase II |
| BAY-94-8862 | Bayer | Mineralocorticoid Receptor (MR) Antagonists | Phase II |
| COR-1 | Corimmun | | Phase II |
| CXL-1020 | Cardioxyl Pharmaceuticals | Nitric Oxide Donors | Phase II |
| Cenderitide | Nile Therapeutics | Guanylate Cyclase Activators | Phase II |
| Endometrial regenerative cells | ERCell/ Medistem | | Phase II |
| JNJ-39588146 | Johnson & Johnson | | Phase II |
| Omecamtiv mecarbil | Amgen/ Cytokinetics | Cardiac Myosin Activators | Phase II |
| PL-3994 | Palatin Technologies | Atrial Natriuretic Peptide A (NPR1; Guanylate Cyclase A) Receptor Agonists | Phase II |
| Remestemcel-L | Osiris | | Phase II |
| TRV-120027 | Trevena | Angiotensin AT1 Receptor Ligands | Phase II |
| Urocortin 2 | Neurocrine Biosciences | CRF2 Agonists | Phase II |
| AAV6-CMV-SERCA2a | Imperial College | | Phase I/II |
| Anakinra | National Institutes of Health (NIH) | IL-1 Receptor Antagonists | Phase I/II |
| LipiCell | Bioheart/ Instituto de Medicina Regenerativa | | Phase I/II |
| ALD-201 | Cytomedix/ Texas Heart Institute | | Phase I |
| BAY-1021189 | Bayer | | Phase I |
| BAY-1067197 | Bayer | Adenine Receptor Agonists | Phase I |
| BAY-86-8050 | Bayer | Drugs Acting on Vasopressin (AVP) Receptors | Phase I |
| BIA-5-1058 | BIAL | Dopamine beta-monooxygenase Inhibitors | Phase I |
| CSCs | University of Louisville | | Phase I |
| Calcitonin gene related peptide | VasoGenix | | Phase I |
| JVS-100 | Juventas Therapeutics | | Phase I |
| MyoCell SDF-1 | Bioheart | | Phase I |
| Myoblast | Advanced Cell Technology (ACT) | | Phase I |
| RO-1160367 | Serodus | 5-HT4 Antagonists | Phase I |
| Recombinant human glial growth factor 2 | Acorda/ Vanderbilt University | | Phase I |
| [18F]LMI-1195 | Lantheus Medical Imaging | | Phase I |
| 677950 | Kyoto Prefectural University of Medicine | | Phase I |

(48) Drugs currently in development for the treatment of pulmonary hypertension:

Drugs in development for the treatment of pulmonary hypertension

| Drug Name | Organization | Mechanism of Action | Status |
|---|---|---|---|
| Imatinib mesylate | Novartis | Breast Cancer-Resistant Protein (BCRP; ABCG2) Inhibitors/Abl Kinase Inhibitors/ Angiogenesis Inhibitors/Bcr-Abl Kinase Inhibitors/CSF1R (c-FMS) Inhibitors/KIT (C-KIT) Inhibitors/Apoptosis Inducers/ PDGFRalpha Inhibitors/PDGFRbeta Inhibitors/Inhibitors of Signal Transduction Pathways | Pre-Registered |
| Treprostinil diethanolamine | United Therapeutics | Prostacyclin Analogs | Pre-Registered |
| GSK-1325760A | GlaxoSmithKline | | Phase III |
| Macitentan | Actelion | Endothelin ETA Receptor Antagonists/ Endothelin ETB Receptor Antagonists | Phase III |
| Riociguat | Bayer | Guanylate Cyclase Activators | Phase III |
| Selexipag | Actelion/Nippon Shinyaku | Prostanoid IP Agonists | Phase III |

Drugs in development for the treatment of pulmonary hypertension

| Drug Name | Organization | Mechanism of Action | Status |
|---|---|---|---|
| Udenafil | Dong-A | Phosphodiesterase V (PDE5A) Inhibitors | Phase III |
| L-Citrulline | Nat Heart, Lung, and Blood Institute/ Vanderbilt University | | Phase II/III |
| BQ-123 | Brigham & Women's Hospital | Endothelin ETA Receptor Antagonists | Phase II |
| Cicletanine | Gilead | | Phase II |
| Fasudil hydrochloride | Asahi Kasei | Rho Kinase Inhibitors/Calcium Sensitizers | Phase II |
| Nilotinib hydrochloride monohydrate | Novartis | Bcr-Abl Kinase Inhibitors/Apoptosis Inducers/Inhibitors of Signal Transduction Pathways | Phase II |
| PRX-08066 | Clinical Data | 5-HT2B Antagonists | Phase II |
| Terguride | ErgoNex Pharma | 5-HT2A Antagonists/5-HT2B Antagonists/Dopamine Autoreceptor Agonists/Dopamine D2 Receptor Partial Agonists/Prolactin Secretion Inhibitors | Phase II |
| Tezosentan disodium | Actelion | Endothelin ETA Receptor Antagonists/ Endothelin ETB Receptor Antagonists | Phase II |
| Anakinra | Virginia Commonwealth University (VCU) | IL-1 Receptor Antagonists | Phase I/II |
| Simvastatin | Imperial College | HDL-Cholesterol Increasing Agents/ HMG-CoA Reductase Inhibitors | Phase I/II |
| 99mTC-PulmoBind | Montreal Heart Institute (MHI) | | Phase I |
| APD-811 | Arena | Prostanoid IP Agonists | Phase I |
| Sorafenib | Bayer | Raf kinase B Inhibitors/Raf kinase C Inhibitors/Angiogenesis Inhibitors/Flt3 (FLK2/STK1) Inhibitors/VEGFR-1 (Flt-1) Inhibitors/KIT (C-KIT) Inhibitors/ VEGFR-2 (FLK-1/KDR) Inhibitors/VEGFR-3 (FLT4) Inhibitors/PDGFRbeta Inhibitors/RET Inhibitors/Inhibitors of Signal Transduction Pathways | Phase I |
| Triplelastat | Proteo Biotech | Elastase Inhibitors | Phase I |
| 2586881 | Apeiron Biologics | | Preclinical |
| C-122 | Corridor Pharmaceuticals | Caspase 3 Activators/Dopamine D1 Antagonists/5-HT2B Antagonists/5-HT7 Antagonists/Caspase 8 Activators/ Dopamine D2 Antagonists/ Dopamine D3 Antagonists/Histamine H1 Receptor Antagonists/Caspase 9 Activators/ Apoptosis Inducers | Preclinical |
| PLX-I | United Therapeutics | Angiogenesis Inducers | Preclinical |

(49) Drugs in current development for the treatment of female sexual dysfunction:

Drugs in active development for the treatment of female sexual dysfunction

| Drug Name | Organization | Mechanism of Action | Status |
|---|---|---|---|
| Alprostadil | Apricus Biosciences/VIVUS | | Phase III |
| Prasterone | EndoCeutics/ Monash University | HSD11B1 Expression Inhibitors | Phase III |
| Testosterone transdermal gel | BioSante | Androgen Receptor Agonists | Phase III |
| Bremelanotide | Palatin Technologies | Melanocortin MC3 Receptor Agonists/ Melanocortin MC4 Receptor Agonists | Phase II |
| Pill-Plus | Pantarhei Bioscience | | Phase II |
| Testosterone MDTS | Acrux | Androgen Receptor Agonists | Phase II |
| Estradiol/testosterone | BioSante | Estrogen Receptor (ER) Agonists/ Androgen Receptor Agonists | Phase I |
| LGD-2941 | Ligand | Selective Androgen Receptor | Phase I |

Drugs in active development for the treatment of female sexual dysfunction

| Drug Name | Organization | Mechanism of Action | Status |
|---|---|---|---|
| | | Modulators (SARM) | |
| Lidocaine/heparin | Urigen | | Phase I |
| OnabotulinumtoxinA | Allergan | | Phase I |
| S1P-104 | S1 Biopharma | | IND Filed |
| PL-6983 | Palatin Technologies | | Preclinical |
| S1P-401 | S1Biopharma | | Preclinical |

(50) Drugs used for the treatment of erectile dysfunction such as Alprostadil, Aviptadil, Phentolamine mesilate, Weige, Alprostadil;

(51) Drugs currently in development for the treatment of male sexual dysfunction:

Drugs in active development for the treatment of erectile dysfunction

| Drug Name | Organization | Mechanism of Action | Status |
|---|---|---|---|
| Fluvastatin sodium | Novartis | Apoptosis Inducers/HMG-CoA Reductase Inhibitors | Phase III |
| Lodenafil carbonate | Cristalia | Phosphodiesterase V (PDE5A) Inhibitors | Phase III |
| EFLA-400 | Chonbuk National University Hospital | | Phase II/III |
| Apomorphine hydrochloride | Vectura | Dopamine D2 Agonists | Phase II |
| LY-900010 | Lilly | Phosphodiesterase V (PDE5A) Inhibitors/Selective Androgen Receptor Modulators (SARM) | Phase II |
| Nitroglycerin | Futura Medical | | Phase II |
| RX-10100 | Rexahn | Drugs Acting on Dopaminergic Transmission/ Drugs Acting on Serotonergic Transmission | Phase II |
| YHD-1023 | Yuhan | | Phase II |
| INT-007 | IntelGenx | | Phase I |
| LY-2452473 | Lilly | Selective Androgen Receptor Modulators (SARM) | Phase I |
| hMaxi-K | Albert Einstein College of Medicine/Ion Channel Innovations/ Mount Sinai School of Medicine | | Phase I |
| KH-204 | KMSI | | Clinical |
| CKD-533 | Chong Kun Dang Pharm (CKD Pharm) | Phosphodiesterase V (PDE5A) Inhibitors | Preclinical |
| MP-52 | Biopharm | | Preclinical |
| TGHW01AP | Fabre-Kramer | Dopamine D1 Agonists/ Dopamine D2 Agonists | Preclinical |

(51) Drugs in development for the treatment of sleep apnea:

Drugs in development for the treatment of sleep apnea

| Drug Name | Organization | Mechanism of Action | Status |
|---|---|---|---|
| CX-1739 | Cortex | AMPA Receptor Modulators | Phase II |
| Phentermine/ topiramate | VIVUS | AMPA Antagonists/ Kainate Antagonists/ Sodium Channel Blockers/ Carbonic Anhydrase Type II Inhibitors | Phase II |
| AVE-0118 | Sanofi | Potassium Channel Blockers | Phase I |
| Suvorexant | Merck & Co. | Orexin Receptor Antagonists | Phase I |
| COL-132 | Collegium Pharmaceutical | | Clinical |

(52) Drugs currently in development for the treatment of metabolic syndrome:

Antiobesity drugs under active development for the treatment of patients with metabolic syndrome

| Drug Name | Organization | Mechanism of Action | Status |
|---|---|---|---|
| Chromium picolinate | University of Pennsylvania | | Phase II |
| RM-493 | Ipsen | Melanocortin MC4 Receptor Agonists | Preclinical |
| TZP-301 | Tranzyme | GHS Receptor Antagonists | Preclinical |

Antihyperlipidemic drugs under active development for the treatment of patients with metabolic syndrome

| Drug Name | Organization | Mechanism of Action | Status |
|---|---|---|---|
| GFT-505 | Genfit | PPARalpha Agonists/ PPARdelta Agonists | Phase II |
| MBX-8025 | Metabolex | PPARdelta Agonists | Phase II |
| Pitavastatin calcium | Kowa | APOA1 Expression Enhancers/ HMG-CoA Reductase Inhibitors/ SPP1 (Osteopontin) |  Phase I |

-continued

Antihypertipidemic drugs under active development
for the treatment of patients with metabolic syndrome

| Drug Name | Organization | Mechanism of Action | Status |
|---|---|---|---|
| CDX-085 | Cardax Pharmaceuticals | Expression Inhibitors Antioxidants | Preclinical |

(53) Antiobesity drugs:

Drugs marketed for the treatment of obesity

| Drug Name | Organization | Mechanism of Action | Year and country of first launch |
|---|---|---|---|
| Methamphetamine hydrochloride (Desoxyn) | Abbott | Noradrenergic, alpha- and beta-adrenoceptor agonist | 1943 (U.S.) |
| Amfepramone hydrochloride (Tenuate) | Sanofi | Noradrenergic release stimulant | 1959 (U.S.) |
| Phentermine (Ionamin) | UCB Celltech | Noradrenergic release stimulant | 1959 (U.S.) |
| Benzfetamine hydrochloride (Didrex) | Pfizer | Noradrenergic release stimulant | 1960 (U.S.) |
| Phendimetrazine tartrate (Bontril, Prelu-2, Plegine) | Pfizer | Noradrenergic release stimulant | 1961 (U.S.) |
| Mazindol (Sanorex) | Novartis | Noradrenergic reuptake inhibitor | 1973 (U.S.) |
| Orlistat (Xenical) | Roche | Pancreatic lipase inhibitor | 1998 (New Zealand) |
| Sibutramine hydrochloride monohydrate (Meridia, Reductil) | Abbott | Norepinephrine and 5-HT reuptake inhibitor | 1998 (U.S.) (withdrawn 2010) |
| Rimonabant (Acomplia) | Sanofi | Cannabinoid CB1 antagonist | 2006 (U.K.) (withdrawn 2008) |

Kits

The compounds and pharmaceutical formulations described herein may be contained in a kit. The kit may include single or multiple doses of two or more agents, each packaged or formulated individually, or single or multiple doses of two or more agents packaged or formulated in combination. Thus, one or more agents can be present in first container, and the kit can optionally include one or more agents in a second container. The container or containers are placed within a package, and the package can optionally include administration or dosage instructions. A kit can include additional components such as syringes or other means for administering the agents as well as diluents or other means for formulation. Thus, the kits can comprise: a) a pharmaceutical composition comprising a compound described herein and a pharmaceutically acceptable carrier, vehicle or diluent; and b) a container or packaging. The kits may optionally comprise instructions describing a method of using the pharmaceutical compositions in one or more of the methods described herein (e.g. preventing or treating one or more of the diseases and disorders described herein). The kit may optionally comprise a second pharmaceutical composition comprising one or more additional agents described herein for co therapy use, a pharmaceutically acceptable carrier, vehicle or diluent. The pharmaceutical composition comprising the compound described herein and the second pharmaceutical composition contained in the kit may be optionally combined in the same pharmaceutical composition.

A kit includes a container or packaging for containing the pharmaceutical compositions and may also include divided containers such as a divided bottle or a divided foil packet. The container can be, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. It is feasible that more than one container can be used together in a single package to market a single dosage form. For example, tablets may be contained in a bottle which is in turn contained within a box.

An example of a kit is a so-called blister pack. Blister packs are well known in the packaging industry and are being widely used for the packaging of pharmaceutical unit dosage forms (tablets, capsules, and the like). Blister packs generally consist of a sheet of relatively stiff material covered with a foil of a preferably transparent plastic material. During the packaging process, recesses are formed in the plastic foil. The recesses have the size and shape of individual tablets or capsules to be packed or may have the size and shape to accommodate multiple tablets and/or capsules to be packed. Next, the tablets or capsules are placed in the recesses accordingly and the sheet of relatively stiff material is sealed against the plastic foil at the face of the foil which is opposite from the direction in which the recesses were formed. As a result, the tablets or capsules are individually sealed or collectively sealed, as desired, in the recesses between the plastic foil and the sheet. Preferably the strength of the sheet is such that the tablets or capsules can be removed from the blister pack by manually applying pressure on the recesses whereby an opening is formed in the sheet at the place of the recess. The tablet or capsule can then be removed via said opening.

It may be desirable to provide written memory aid containing information and/or instructions for the physician, pharmacist or subject regarding when the medication is to be taken. A "daily dose" can be a single tablet or capsule or several tablets or capsules to be taken on a given day. When the kit contains separate compositions, a daily dose of one or more compositions of the kit can consist of one tablet or capsule while a daily dose of another or more compositions of the kit can consist of several tablets or capsules. A kit can take the form of a dispenser designed to dispense the daily doses one at a time in the order of their intended use. The dispenser can be equipped with a memory-aid, so as to further facilitate compliance with the regimen. An example of such a memory-aid is a mechanical counter which indicates the number of daily doses that have been dispensed. Another example of such a memory-aid is a battery-powered micro-chip memory coupled with a liquid crystal readout, or audible reminder signal which, for example, reads out the date that the last daily dose has been taken and/or reminds one when the next dose is to be taken.

EXAMPLES

All references provided in the Examples are herein incorporated by reference. As used herein, all abbreviations, symbols and conventions are consistent with those used in the contemporary scientific literature. See, e.g. Janet S. Dodd, ed., The ACS Style Guide: A Manual for Authors and Editors, $2^{nd}$ Ed., Washington, D.C.: American Chemical Society, 1997, herein incorporated in its entirety by reference.

Example 1

Syntheses of Compounds

Intermediate 1 (Scheme 1)

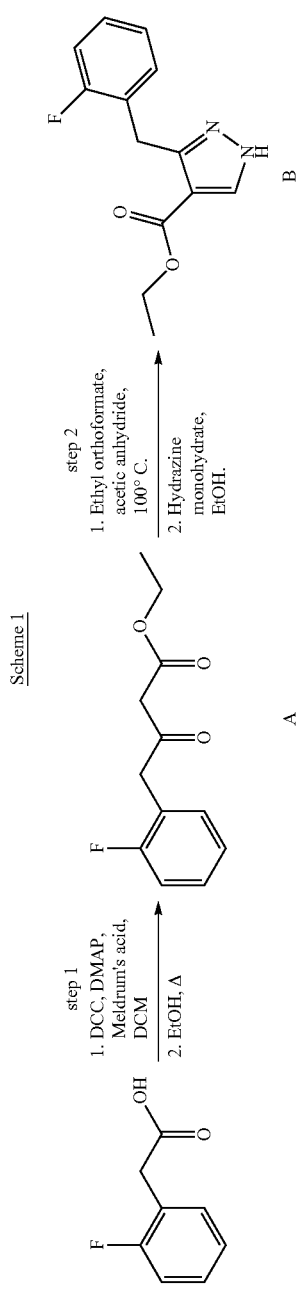
Scheme 1

-continued
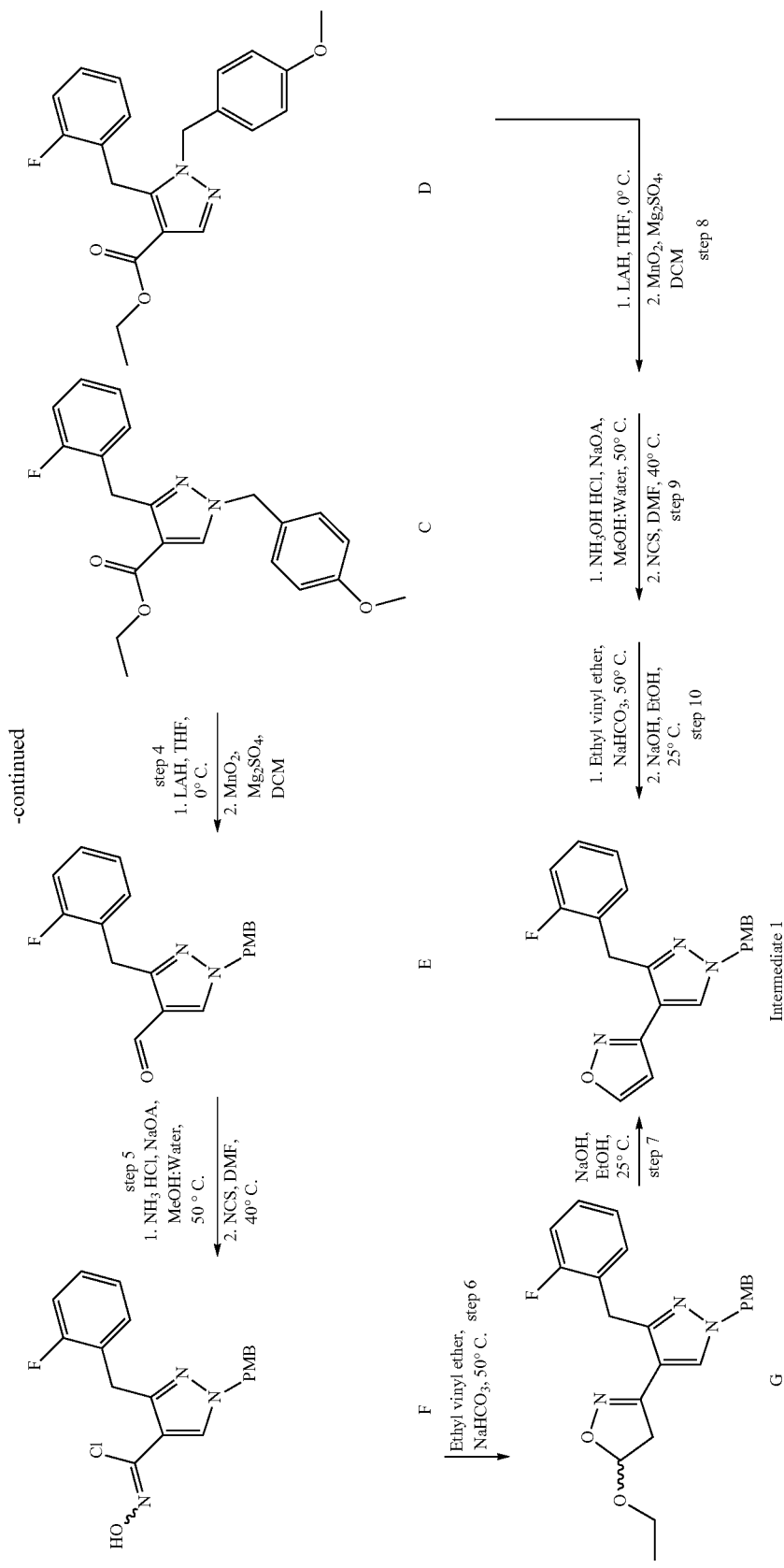

Step 1. Preparation of A

To a solution of 1,3-dicyclohexylcarbodiimide (DCC, 23.0 g, 1.0 equiv.) in dichloromethane (200 ml), were added 4-dimethylaminopyridine (DMAP, 13.6 g, 1.0 equiv.), o-fluorophenylacetic acid (17.2 g, 1.0 equiv.) and Meldrums acid (16.1 g, 1.0 equiv.). The mixture and the resulting precipitate was removed by filtration. The filtrate was diluted with dichloromethane and washed with 1N HCl (100 ml). The organic layer was dried, filtered and evaporated to give a solid. This was suspended in ethanol and heated at reflux for 24 h. The mixture was concentrated under vacuum. The resulting residue was purified by column chromatography (0 to 30% ethyl acetate in hexanes) to give ethyl 4-(2-fluorophenyl)-3-oxobutanoate (A, 19.1 g, 76% yield) as an orange oil.

$^1$H NMR (500 MHz, CHLOROFORM-d) δ ppm 7.26-7.33 (m, 1H), 7.22 (td, 1H), 7.12-7.17 (m, 1H), 7.09 (t, 1H), 4.18-4.24 (m, 2H), 3.90 (s, 2H), 3.53 (s, 2H), 1.27-1.32 (m, 3H).

Step 2. Preparation of B

A mixture of ethyl 4-(2-fluorophenyl)-3-oxobutanoate (A, 19.0 g, 1.0 equiv.), ethyl orthoformate (42.3 ml, 3.0 equiv.) and acetic anhydride (12.8 ml, 1.6 equiv.) was heated at 100° C. for 24 h and then concentrated under vacuum to give a thick oil. The resulting residue was diluted in ethanol (85 ml) and cooled to 0° C. in an ice bath. To this mixture, was added, very slowly, hydrazine monohydrate (2.7 ml, 1.0 equiv.). The mixture was stirred at rt for 2 h and then concentrated. The resulting residue was purified by column chromatography (0 to 30% ethyl acetate in hexanes) to give ethyl 3-(2-fluorobenzyl)-1H-pyrazole-4-carboxylate (B, 14.0 g, 66% yield) as a dark red oil.

$^1$H NMR (400 MHz, CHLOROFORM-d) δ ppm 7.93 (s, 1H), 7.18-7.26 (m, 3H), 7.01-7.09 (m, 2H), 4.34 (s, 2H), 4.28 (q, 2H), 1.33 (t, 3H).

Step 3. Preparation of C and D

A mixture of ethyl 3-(2-fluorobenzyl)-1H-pyrazole-4-carboxylate (12.6 g, 1.0 equiv.), potassium carbonate (10.5 g, 1.5 equiv.) and 4-methoxybenzyl chloride (7.2 ml, 1.1 mmol) in acetonitrile (60 ml) was heated at reflux for 24 h. The mixture was cooled and filtered. The filtrate was concentrated to give a thick oil. Purification of the oil by column chromatography (0 to 5% ethyl acetate in hexanes) gave ethyl 3-(2-fluorobenzyl)-1-(4-methoxybenzyl)-1H-pyrazole-4-carboxylate (C, 8.4 g, 45% yield) as a clear oil. In addition, ethyl 5-(2-fluorobenzyl)-1-(4-methoxybenzyl)-1H-pyrazole-4-carboxylate (D, 4.2 g, 23% yield) was also obtained as a side product as a clear oil. Side product D was also used for the preparation of the final product (Intermediate-1) by an alternative route described below.

Ethyl 3-(2-fluorobenzyl)-1-(4-methoxybenzyl)-1H-pyrazole-4-carboxylate (C)

$^1$H NMR (400 MHz, CHLOROFORM-d) δ ppm 7.74 (s, 1H), 7.16-7.22 (m, 2H), 7.06-7.16 (m, 2H), 6.94-7.04 (m, 2H), 6.88 (d, 2H), 5.17 (s, 2H), 4.27 (s, 2H), 4.17 (q, 2H), 3.80 (s, 3H), 1.19 (t, 3H).

Ethyl 5-(2-fluorobenzyl)-1-(4-methoxybenzyl)-1H-pyrazole-4-carboxylate (D)

$^1$H NMR (400 MHz, CHLOROFORM-d) δ ppm 7.96 (s, 1H), 7.13-7.20 (m, 1H), 7.02 (d, 1H), 6.94-6.99 (m, 3H), 6.84-6.91 (m, 1H), 6.75 (d, 2H), 5.11 (s, 2H), 4.37 (s, 2H), 4.25 (q, 2H), 3.74 (s, 3H), 1.27 (q, 3H).

Step 4. Preparation of E

4.1: Synthesis of (3-(2-fluorobenzyl)-1-(4-methoxybenzyl)-1H-pyrazol-4-yl)methanol To a cold solution of ethyl 3-(2-fluorobenzyl)-1-(4-methoxybenzyl)-1H-pyrazole-4-carboxylate (C, 8.4 g, 1.0 equiv.) in THF (114 ml) at 0° C., was added 2.0 M solution of lithium aluminum hydride in THF (11.4 ml, 1.0 equiv.). The mixture was stirred at rt for 30 min. and cooled to 0° C. The mixture was sequentially quenched with 870 μl of water, 870 μl of 15% NaOH and 2.5 ml of water. The precipitate formed was removed by filtration. The filtrate was concentrated under vacuum to give (3-(2-fluorobenzyl)-1-(4-methoxybenzyl)-1H-pyrazol-4-yl)methanol (8.4 g, 100% yield) as a clear oil. This compound was used in step 5.2 without further purification.

$^1$H NMR (400 MHz, CHLOROFORM-d) δ ppm 7.24 (s, 1H), 7.13-7.20 (m, 4H), 6.97-7.06 (m, 2H), 6.83-6.89 (m, 2H), 5.16 (s, 2H), 4.37 (s, 2H), 4.04 (s, 2H), 3.78 (s, 3H).

4.2. Synthesis of E

A mixture of the crude (3-(2-fluorobenzyl)-1-(4-methoxybenzyl)-1H-pyrazol-4-yl)methanol (8.4 g, 1.0 equiv.), magnesium sulfate (4.3 g, 1.4 equiv.) and manganese dioxide (15.4 g, 6.9 equiv.) in dichloromethane (129 ml) was stirred at rt for 24 h. The mixture was filtered through a funnel to remove insoluble materials. The filtrate was concentrated under vacuum to give 3-(2-fluorobenzyl)-1-(4-methoxybenzyl)-1H-pyrazole-4-carbaldehyde (E, 6.9 g, 82% yield) as a light yellow oil.

$^1$H NMR (400 MHz, CHLOROFORM-d) δ ppm 9.77 (s, 1H), 7.69 (s, 1H), 7.13-7.25 (m, 4H), 6.98-7.06 (m, 2H), 6.89 (d, 2H), 5.19 (s, 2H), 4.26 (s, 2H), 3.80 (s, 3H).

Step 5. Preparation of F

5.1. Synthesis of 3-(2-fluorobenzyl)-1-(4-methoxybenzyl)-1H-pyrazole-4-carbaldehyde oxime A mixture containing 3-(2-fluorobenzyl)-1-(4-methoxybenzyl)-1H-pyrazole-4-carbaldehyde (E, 6.9 g, 1 equiv.), hydroxylamine hydrochloride (1.6 g, 1.1 equiv.) and sodium acetate (1.8 g, 1.0 equiv.) in a mixture of methanol (95 ml) and water (11 ml) was heated at 50° C. for 3 h. The mixture was cooled to rt and concentrated under vacuum. The resulting residue was diluted in ethyl acetate (100 ml) and washed with brine (50 ml). The organic layer was dried, filtered and evaporated to give 3-(2-fluorobenzyl)-1-(4-methoxybenzyl)-1H-pyrazole-4-carbaldehyde oxime (4.3 g, 60% yield) as a white solid. This material was used directly in the following step (5.2) without additional purification.

$^1$H NMR (400 MHz, CHLOROFORM-d) δ ppm 8.27 (s, 1H), 7.39 (s, 1H), 7.15-7.23 (m, 3H), 7.10 (t, 1H), 6.97-7.06 (m, 2H), 6.87 (d, 2H), 5.16-5.25 (m, 2H), 3.79 (s, 3H), 3.47 (s, 2H).

5.2. Synthesis of F

A mixture of 3-(2-fluorobenzyl)-1-(4-methoxybenzyl)-1H-pyrazole-4-carbaldehyde oxime (4.3 g, 1.0 equiv.) and N-chlorosuccinimide (NCS, 1.8 g, 1.1 equiv.) in DMF (13 ml) was heated at 40° C. for 3 h. The mixture was cooled to rt. Then, it was diluted in ethyl acetate (200 ml) and washed with water (50 ml×3). The organic layer was dried, filtered and evaporated to give an oil. Purification of the oil by column chromatography (0 to 20% ethyl acetate in hexanes) gave 3-(2-fluorobenzyl)-N-hydroxy-1-(4-methoxybenzyl)-1H-pyrazole-4-carbimidoyl chloride (F, 4.0 g, 85% yield) as a yellow solid.

$^1$H NMR (400 MHz, CHLOROFORM-d) δ ppm 7.58 (s, 1H), 7.19 (d, 2H), 7.10-7.17 (m, 1H), 6.93-7.04 (m, 3H), 6.86-6.91 (m, 2H), 5.17 (s, 2H), 4.19 (s, 2H), 3.79 (s, 3H).

Step 6. Preparation of G

A mixture of 3-(2-fluorobenzyl)-N-hydroxy-1-(4-methoxybenzyl)-1H-pyrazole-4-carbimidoyl chloride (F, 4.0 g, 1.0 equiv.), ethyl vinyl ether (2.3 ml, 2.2 equiv.) and sodium bicarbonate (1.3 g, 1.5 equiv) in 2-propanol (15 ml) was heated at 50° C. for 24 h. The precipitate was removed by filtration. The filtrate was concentrated under vacuum to give an oil. Purification of the oil by column chromatography (0 to 100% ethyl acetate in hexanes) gave 5-ethoxy-3-(3-(2-fluorobenzyl)-1-(4-methoxybenzyl)-1H-pyrazol-4-yl)-4,5-dihydroisoxazole (G, 1.0 g, 23% yield) as a clear oil.

$^1$H NMR (400 MHz, CHLOROFORM-d) δ ppm 7.42 (s, 1H) 7.14-7.24 (m, 4H) 6.98-7.06 (m, 2H) 6.87-6.93 (m, 2H) 5.50-5.55 (m, 1H) 5.21 (s, 2H) 4.23-4.37 (m, 2H) 3.84-3.91 (m, 1H) 3.83 (s, 3H) 3.49-3.59 (m, 1H) 3.20 (dd, 1H) 2.93-2.99 (m, 1H) 1.27 (t, 3H).

Step 7. Synthesis of Intermediate 1

A mixture of 5-ethoxy-3-(3-(2-fluorobenzyl)-1-(4-methoxybenzyl)-1H-pyrazol-4-yl)-4,5-dihydroisoxazole (G, 1.0 g, 1.0 equiv.) and 1.0 M solution of sodium hydroxide in water (2.4 ml, 1.0 equiv.) in ethanol (12 ml) was stirred at rt for 24 h. The mixture was concentrated under vacuum and then it was diluted in ethyl acetate (100 ml) and washed with 1N HCl (50 ml). The organic layer was dried, filtered and evaporated to give an oil. Purification of the oil by column chromatography (0 to 80% ethyl acetate in hexanes) gave Intermediate-1 (797 mg, 90% yield) as a clear oil.

$^1$H NMR (500 MHz, CHLOROFORM-d) δ ppm 8.34 (br. s., 1H), 7.70 (br. s., 1H), 7.25-7.32 (m, 2H), 7.12-7.24 (m, 2H), 7.00-7.10 (m, 2H), 6.88-6.97 (m, 2H), 6.31 (br. s., 1H), 5.24-5.34 (m, 2H), 4.32 (br. s., 2H), 3.84 (br. s., 3H).

Alternative Synthesis of Intermediate-1 from Side Product D

Step 8

8.1. Synthesis of (5-(2-fluorobenzyl)-1-(4-methoxybenzyl)-1H-pyrazol-4-yl)methanol To a cold solution of ethyl 5-(2-fluorobenzyl)-1-(4-methoxybenzyl)-1H-pyrazole-4-carboxylate (D, 4.2 g, 1.0 equiv.) in THF (57 ml) at 0° C., was added 2.0 M solution of lithium aluminum hydride in THF (5.7 ml, 1.0 equiv.). The mixture was stirred at rt and cooled to 0° C. The mixture was sequentially quenched with 435 μl of water, 435 μl of 15% NaOH and 1.3 ml of water. The precipitate that formed was removed by filtration. The filtrate was concentrated under vacuum to give (5-(2-fluorobenzyl)-1-(4-methoxybenzyl)-1H-pyrazol-4-yl)methanol (3.2 g, 85% yield) as a clear oil. This was used in the following step without additional purification.

$^1$H NMR (400 MHz, CHLOROFORM-d) δ ppm 7.58 (s, 1H) 7.15-7.22 (m, 2H), 6.96-7.01 (m, 3H), 6.81-6.89 (m, 2H) 6.74-6.78 (m, 1H), 5.10-5.14 (m, 2H) 4.51 (s, 2H) 4.00 (s, 2H) 3.72-3.76 (m, 3H).

8.2. Synthesis of 5-(2-fluorobenzyl)-1-(4-methoxybenzyl)-1H-pyrazole-4-carbaldehyde A mixture of (5-(2-fluorobenzyl)-1-(4-methoxybenzyl)-1H-pyrazol-4-yl)methanol (3.2 g, 1.0 equiv.), magnesium sulfate (1.6 g, 1.4 equiv.) and manganese dioxide (5.9 g, 6.9 equiv.) in dichloromethane (49 ml) was stirred at rt for 24 h. The solid precipitate was removed by filtration. The filtrate was concentrated under vacuum to give 5-(2-fluorobenzyl)-1-(4-methoxybenzyl)-1H-pyrazole-4-carbaldehyde (3.1 g, 98% yield) as a light yellow oil.

$^1$H NMR (400 MHz, CHLOROFORM-d) δ ppm 9.87-9.96 (m, 1H), 7.98 (s, 1H), 7.15-7.23 (m, 2H), 6.96-7.07 (m, 2H), 6.87-6.96 (m, 2H), 6.77 (d, 2H), 5.15 (s, 2H), 4.34 (s, 2H), 3.75 (s, 3H).

Step 9

9.1. Synthesis of 5-(2-fluorobenzyl)-1-(4-methoxybenzyl)-1H-pyrazole-4-carbaldehyde oxime A mixture containing 5-(2-fluorobenzyl)-1-(4-methoxybenzyl)-1H-pyrazole-4-carbaldehyde (3.1 g, 1.0 equiv.), hydroxylamine hydrochloride (0.72 g, 1.1 equiv.) and sodium acetate (0.83 g, 1.1 equiv.) in a 9:1 mixture of MeOH (43 ml) and water (5 ml) was heated at 50° C. for 3 h. The mixture was cooled to rt and concentrated under vacuum. The resulting residue was diluted in ethyl acetate (100 ml) and washed with brine (50 ml). The organic layer was dried, filtered and evaporated to give 5-(2-fluorobenzyl)-1-(4-methoxybenzyl)-1H-pyrazole-4-carbaldehyde oxime (3.0 g, 91% yield) as a white solid. This was used in the following step without additional purification.

$^1$H NMR (400 MHz, CHLOROFORM-d) δ ppm 8.47 (s, 1H), 7.49 (br. s., 1H), 7.21 (d, 3H), 6.94-7.01 (m, 3H), 6.70-6.82 (m, 2H), 5.19 (s, 2H), 4.09 (s, 2H), 3.75 (s, 3H).

9.2. Synthesis of 5-(2-fluorobenzyl)-N-hydroxy-1-(4-methoxybenzyl)-1H-pyrazole-4-carbimidoyl chloride A mixture of 5-(2-fluorobenzyl)-1-(4-methoxybenzyl)-1H-pyrazole-4-carbaldehyde oxime (3.0 g, 1.0 equiv.) and N-chlorosuccinimide (1.2 g, 1.1 equiv.) in DMF (9.0 ml) was heated at 40° C. for 3 h. The mixture was cooled to rt and diluted ethyl acetate (500 ml). The organic layer was washed with water (50 ml×3), dried, filtered and evaporated to give an oil. The oil was purified by column chromatography (0 to 20% ethyl acetate in hexanes) to give 5-(2-fluorobenzyl)-N-hydroxy-1-(4-methoxybenzyl)-1H-pyrazole-4-carbimidoyl chloride (2.4 g, 73% yield) as a yellow solid.

$^1$H NMR (400 MHz, CHLOROFORM-d) δ ppm 7.86 (s, 1H), 7.57 (s, 1H), 7.55-7.55 (m, 1H), 7.12-7.22 (m, 2H), 6.92-7.00 (m, 2H), 6.72-6.80 (m, 3H), 5.07 (s, 2H), 4.26 (s, 2H), 3.74 (s, 3H).

Step 10. Alternative Synthesis of Intermediate-1

10.1. Preparation of G

A mixture of 5-(2-fluorobenzyl)-N-hydroxy-1-(4-methoxybenzyl)-1H-pyrazole-4-carbimidoyl chloride (2.4 g, 1.0 equiv.), ethyl vinyl ether (1.3 ml, 2.2 equiv.) and sodium bicarbonate (0.80 g, 1.5 equiv.) in 2-propanol (7.1 ml) was heated at 50° C. for 3 h. The precipitate was removed by filtration. The filtrate was concentrated under vacuum to give an oil. Purification of the oil by column chromatography (0 to 100% ethyl acetate in hexanes) gave compound G (2.0 g, 75% yield) as a yellow oil.

$^1$H NMR (400 MHz, CHLOROFORM-d) δ ppm 7.63 (s, 1H), 7.11-7.20 (m, 2H), 6.85-7.04 (m, 4H), 6.75 (d, 2H), 5.55-5.58 (m, 1H), 5.11 (s, 2H), 4.28-4.47 (m, 2H), 3.81-3.94 (m, 1H), 3.74 (s, 3H) 3.50-3.61 (m, 1H) 3.36 (dd, 1H) 3.10-3.19 (m, 1H) 1.21-1.27 (m, 3H).

10.2. Preparation of Intermediate 1

A mixture of 5-ethoxy-3-(5-(2-fluorobenzyl)-1-(4-methoxybenzyl)-1H-pyrazol-4-yl)-4,5-dihydroisoxazole (G, 2.0 g, 1.0 equiv.) and 1.0 M solution of sodium hydroxide in water (4.8 ml, 1.0 equiv.) was stirred at rt for 24 h. The mixture was concentrated under vacuum. The mixture was diluted in ethyl acetate (100 ml) and washed with 1N HCl (50 ml). The organic layer was dried, filtered and evaporated to give an oil. Purification of the oil by column chromatography (0 to 80% ethyl acetate in hexanes) gave Intermediate 1 (1.3 g, 77% yield) as a yellow oil.

$^1$H NMR (500 MHz, CHLOROFORM-d) δ ppm 8.42 (br. s., 1H), 7.88 (br. s., 1H), 7.20 (br. s., 2H), 7.01-7.10 (m, 2H), 6.89-7.01 (m, 2H), 6.80 (d, 2H), 6.50 (br. s., 1H), 5.18 (br. s., 2H), 4.42 (br. s., 2H), 3.79 (br. s., 3H).

A solution containing Intermediate 1 (182 mg, 1.0 equiv.) in trifluoroacetic acid (1.7 ml) was heated at 70° C. for 24 h. The mixture was cooled to rt and diluted in dichloromethane. The organic layer was washed with a saturated solution of sodium bicarbonate (100 ml), dried, filtered and evaporated to give an oil. The oil was purified by column chromatography (0 to 80% ethyl acetate in hexanes) to give Intermediate 2 (93 mg, 76% yield) as an off-white solid.

$^1$H NMR (400 MHz, CHLOROFORM-d) δ ppm 10.14 (br. s., 1H) 8.42-8.53 (m, 1H) 7.91 (d, 1H) 7.18-7.23 (m, 1H) 6.97-7.04 (m, 2H) 6.51-6.63 (m, 1H) 6.28-6.39 (m, 1H) 5.74-5.93 (m, 2H).

Compound I-1

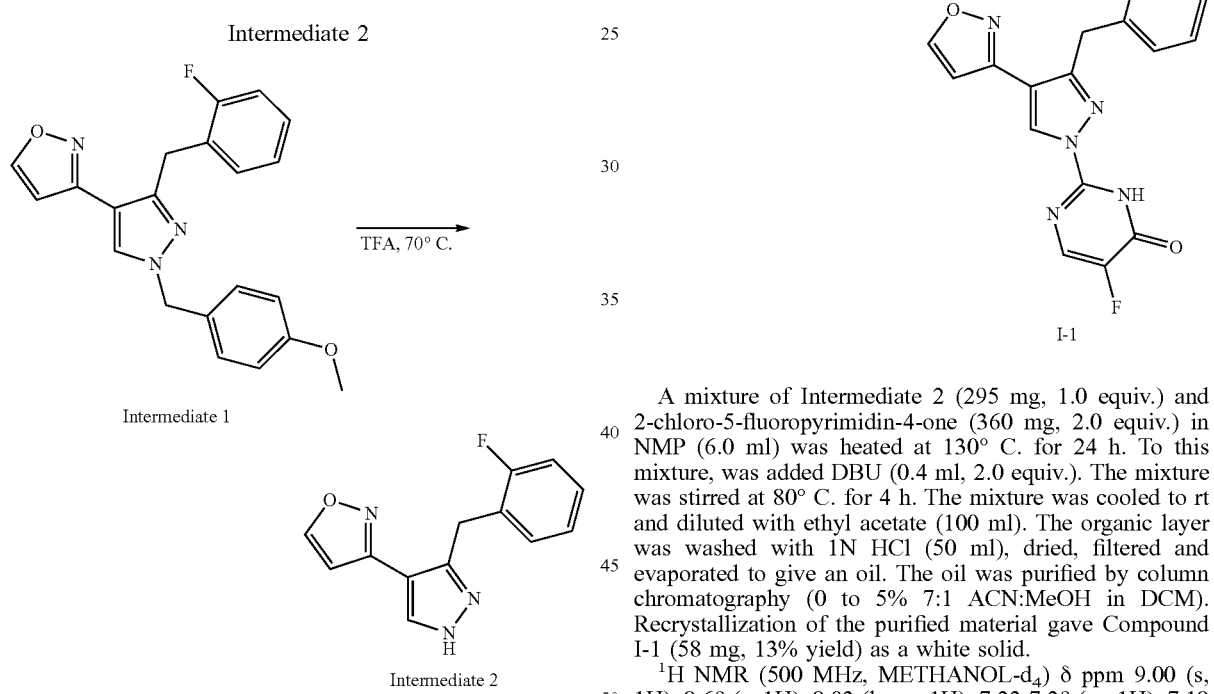

A mixture of Intermediate 2 (295 mg, 1.0 equiv.) and 2-chloro-5-fluoropyrimidin-4-one (360 mg, 2.0 equiv.) in NMP (6.0 ml) was heated at 130° C. for 24 h. To this mixture, was added DBU (0.4 ml, 2.0 equiv.). The mixture was stirred at 80° C. for 4 h. The mixture was cooled to rt and diluted with ethyl acetate (100 ml). The organic layer was washed with 1N HCl (50 ml), dried, filtered and evaporated to give an oil. The oil was purified by column chromatography (0 to 5% 7:1 ACN:MeOH in DCM). Recrystallization of the purified material gave Compound I-1 (58 mg, 13% yield) as a white solid.

$^1$H NMR (500 MHz, METHANOL-d$_4$) δ ppm 9.00 (s, 1H), 8.69 (s, 1H), 8.03 (br. s., 1H), 7.22-7.29 (m, 1H), 7.18 (t, 1H), 7.02-7.12 (m, 2H), 6.78 (s, 1H), 4.42-4.48 (m, 2H).

Intermediate-3 and Compound I-2 (Scheme 2)

Scheme 2

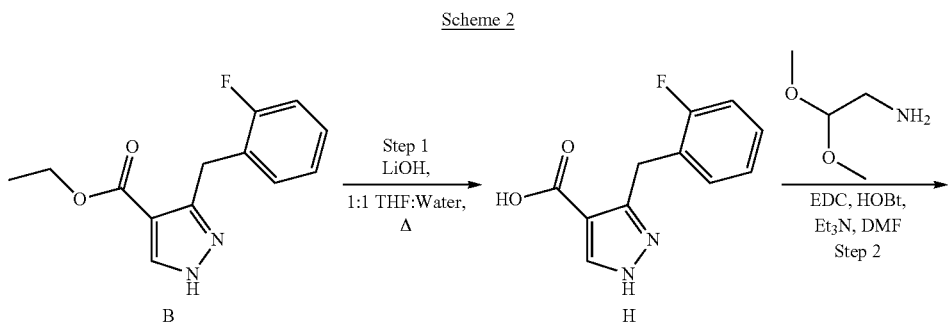

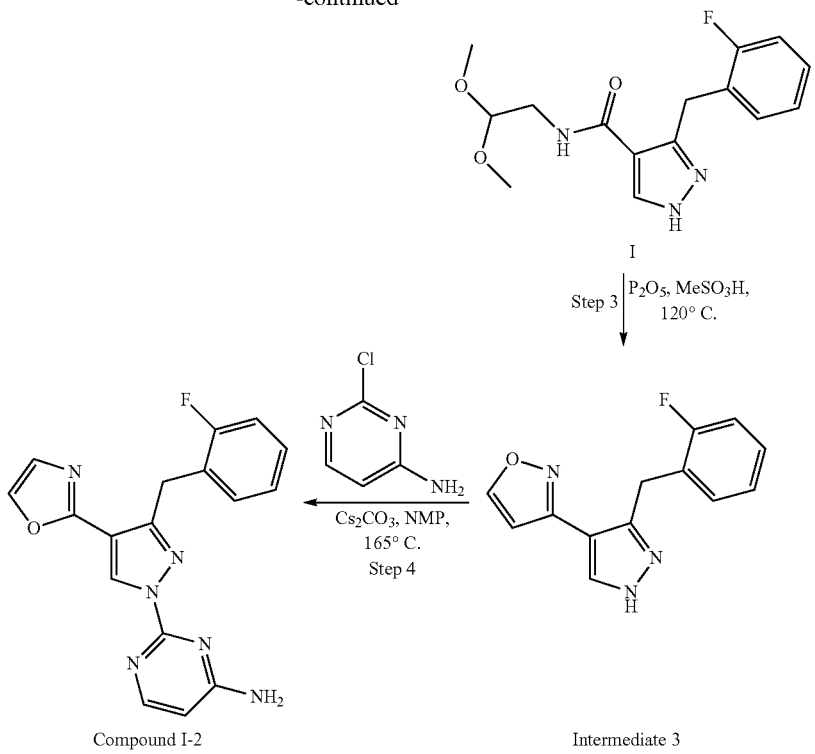

Compound I-2

Intermediate 3

Step 1. Synthesis of H

A mixture of ethyl 3-(2-fluorobenzyl)-1H-pyrazole-4-carboxylate (B, 5.0 g, 1.0 equiv.) and lithium hydroxide (2.4 g, 5.0 equiv.) in a 1:1 mixture of THF (51 ml) and water (51 ml) was heated at 100° C. for 4 h. The organic solvent of the mixture was evaporated. The resulting aqueous mixture was acidified to pH=3 by the addition of 3N HCl. The resulting white precipitate was collected and dried under vacuum to give 3-(2-fluorobenzyl)-1H-pyrazole-4-carboxylic acid (H, 4.1 g, 92% yield) as an off-white solid which was used directly in the next step without additional purification.

$^1$H NMR (400 MHz, METHANOL-$d_4$) δ ppm 7.94 (br. s., 1H), 7.12-7.20 (m, 2H), 7.02-7.08 (m, 1H), 6.95-7.02 (m, 2H), 4.26 (s, 2H).

Step 2. Synthesis of I

To a mixture of 3-(2-fluorobenzyl)-1H-pyrazole-4-carboxylic acid (H, 4.1 g, 1.0 equiv.), EDC (3.9 g, 1.1 equiv.), HOBT (3.1 g, 1.1 equiv.) and triethylamine (5.2 ml, 2.0 equiv.) in N,N-dimethylformamide (93 ml), was added 2,2-dimethoxyethanamine (2.2 ml, 1.1 equiv.). The mixture was stirred at 25° C. for 24 h. It was diluted in ethyl acetate (100 ml) and washed with brine (50 ml×3). The organic layer was dried, filtered, and concentrated to give N-(2,2-dimethoxyethyl)-3-(2-fluorobenzyl)-1H-pyrazole-4-carboxamide (I, 3.2 g, 57% yield) as a light yellow oil.

$^1$H NMR (400 MHz, CHLOROFORM-d) δ ppm 7.74 (s, 1H), 7.23 (t, 1H), 7.13-7.20 (m, 1H), 6.94-7.04 (m, 2H), 4.39 (t, 1H), 4.34 (s, 2H), 3.46 (t, 2H), 3.33 (s, 6H).

Step 3. Synthesis of Intermediate-3

A mixture of N-(2,2-dimethoxyethyl)-3-(2-fluorobenzyl)-1H-pyrazole-4-carboxamide (3.2 g, 1.0 equiv.) and phosphorous pentoxide (10 g, 6.8 equiv.) in methanesulfonic acid (70 ml) was heated at 120° C. for 24 h. The mixture turned dark brown. The mixture was cooled to rt and poured over ice. It was basified with a 3N NaOH solution to pH=7. The mixture was extracted with ethyl acetate (200 ml×3). The combined organic layer were dried, filtered, and evaporated to give an oil. Purification of the oil by column chromatography (0 to 50% acetone in hexanes) gave Intermediate-3 (1.3 g, 51% yield) as a yellow oil.

$^1$H NMR (400 MHz, CHLOROFORM-d) δ ppm 8.01 (s, 1H), 7.62 (d, 1H), 7.30 (td, 1H), 7.19-7.26 (m, 1H), 7.17 (d, 1H), 7.03-7.09 (m, 2H), 4.46 (s, 2H).

Step 4. Preparation of Compound I-2

A mixture of Intermediate-3 (160 mg, 1.0 equiv.), 2-chloropyrimidin-4-amine (170 mg, 2.0 equiv.) and cesium carbonate (429 mg, 2.0 equiv.) in NMP (7.0 ml) was heated at 165° C. in a sealed vial for 2 days. The reaction was cooled to rt and diluted in ethyl acetate (200 ml). The mixture was washed with water (30 ml×3) and brine. The organic layer was dried, filtered, and evaporated to give a crude oil. The oil was purified by column chromatography (0 to 80% ethyl acetate in hexanes), and the resulting crude product was tritrated with acetone to Compound I-2 (52 mg, 23% yield) as an off-white solid.

$^1$H NMR (400 MHz, DMSO-$d_6$) δ ppm 8.94 (s, 1H), 8.15 (d, 1H), 8.10 (d, 1H), 7.41 (br. s., 2H), 7.32-7.35 (m, 1H), 7.22-7.30 (m, 1H), 7.13-7.22 (m, 2H), 7.03-7.13 (m, 1H), 6.39 (d, 1H), 4.41 (s, 2H).

Compounds I-3 and I-4 (Scheme 3)

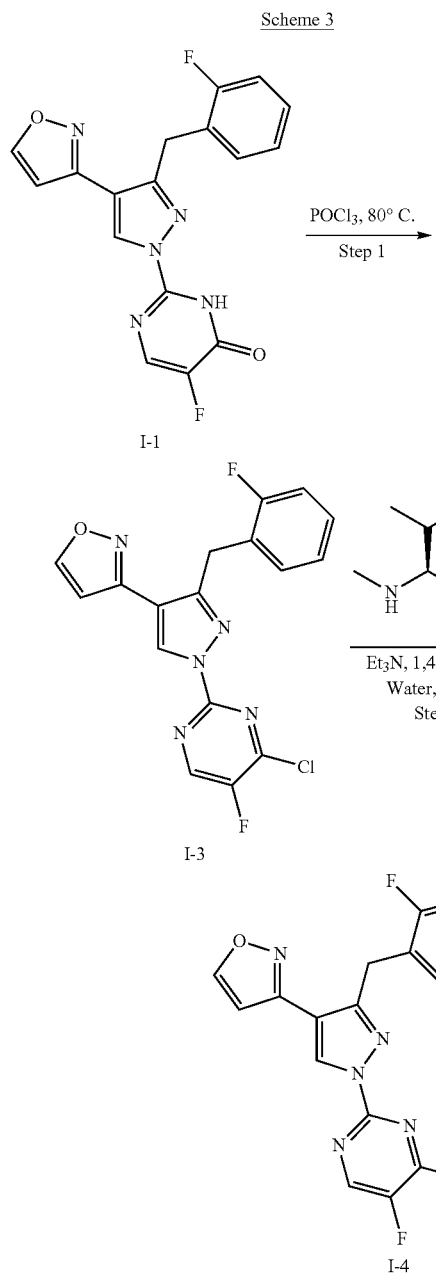

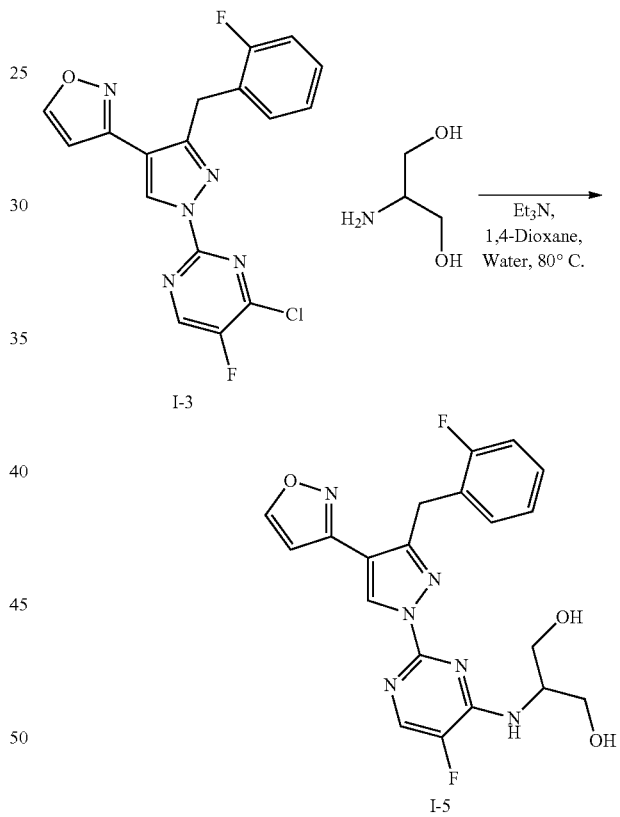

Step 1. Compound I-3

A mixture of Compound I-1 (365 mg, 1 equiv.) and phosphorous oxytrichloride (2.0 ml, 20 equiv.) was heated at 80° C. for 24 h. The mixture was concentrated under vacuum. The resulting residue was diluted with ethyl acetate (100 ml) and washed with water (50 ml). The organic layer was dried, filtered and evaporated to give an oil. The oil was purified by column chromatography (0 to 30% ethyl acetate in hexanes) to give Compound I-3 (164 mg, 43% yield) as a white solid.

1H NMR (500 MHz, CHLOROFORM-d) δ ppm 8.89-8.94 (m, 1H) 8.63 (s, 1H) 8.40-8.44 (m, 1H) 7.13-7.22 (m, 2H) 6.95-7.08 (m, 2H) 6.40-6.46 (m, 1H) 4.44-4.50 (m, 2H).

Step 2. Compound I-4

A mixture of Compound I-3 (159 mg, 1 equiv.), (S)-3-methyl-2-(methylamino)butyric acid (112 mg, 2 equiv.) and triethylamine (119 μl, 2 equiv.) in 1,4-dioxane (5.7 ml) and water (2.8 ml) was heated at 80° C. for 24 h. The mixture was diluted in ethyl acetate (100 ml) and washed with 1N HCl (50 ml). The organic layer was dried, filtered and evaporated to give a solid. The solid was purified by column chromatography (0 to 10% methanol in dichloromethane) to give Compound I-4 (50 mg, 25% yield) as a solid.

$^1$H NMR (500 MHz, DMSO-d$_6$) δ ppm 9.02 (s, 1H) 8.97 (d, 1H) 8.33 (d, 1H) 7.22-7.28 (m, 1H) 7.20 (t, 1H) 7.13-7.18 (m, 1H) 7.07 (td, 1H) 7.00 (s, 1H) 4.62 (br. s., 1H) 4.33 (s, 2H) 3.32 (s, 2H) 3.22 (d, 3H) 2.34-2.43 (m, 1H) 1.07 (d, 3H) 0.88 (d, 3H).

Compound I-5

A mixture of 3-(1-(4-chloro-5-fluoropyrimidin-2-yl)-3-(2-fluorobenzyl)-1H-pyrazol-4-yl)isoxazole (Compound I-3, 100 mg, 1 equiv.), triethylamine (149 μl, 4 equiv.) and 2-amino-1,3-propanediol (98 mg, 4 equiv.) in 1,4-dioxane (2.0 ml) and water (0.5 ml) was heated at 80° C. for 4 h. The mixture was diluted in ethyl acetate (100 ml) and washed with 1N HCl (50 ml). The organic layer was dried, filtered and evaporated to give Compound I-5 (53 mg, 46% yield) as a white solid.

$^1$H NMR (500 MHz, METHANOL-d$_4$) δ ppm 8.99 (s, 1H) 8.62 (d, 1H) 8.03 (d, 1H) 7.17 (d, 1H) 7.00-7.07 (m, 2H) 6.95-6.99 (m, 1H) 6.71 (d, 1H) 4.54 (t, 1H) 4.39 (s, 2H) 3.73-3.82 (m, 4H).

Compound I-6

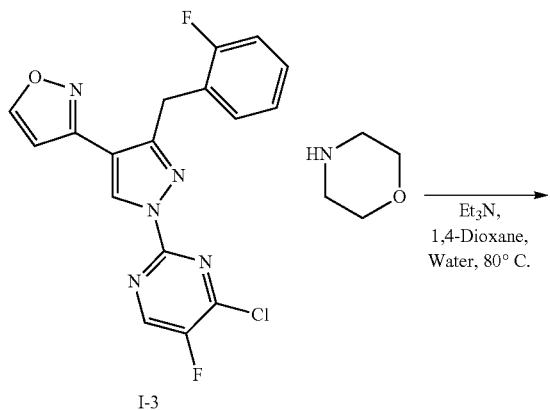

A mixture of 3-(1-(4-chloro-5-fluoropyrimidin-2-yl)-3-(2-fluorobenzyl)-1H-pyrazol-4-yl)isoxazole (Compound I-3, 45 mg, 1 equiv.), triethylamine (67 μl, 4 equiv.) and morpholine (42 μl, 4 equiv.) in 1,4-dioxane (0.9 ml) and water (0.2 ml) was heated at 80° C. for 4 h. The mixture was diluted in ethyl acetate (100 ml) and washed with 1N HCl (50 ml). The organic layer was dried, filtered and evaporated to give a white solid. The solid was rinsed with a minimal amount of methanol to give Compound I-6 (38 mg, 74% yield) as a white solid.

$^1$H NMR (500 MHz, DMSO-d$_6$) δ ppm 9.13 (s, 1H) 8.95 (d, 1H) 8.31 (d, 1H) 7.21-7.28 (m, 1H) 7.09-7.19 (m, 3H) 7.04-7.09 (m, 1H) 4.33 (s, 2H) 3.79-3.88 (m, 4H) 3.69-3.79 (m, 4H) 3.57 (s, 1H).

Compound I-7

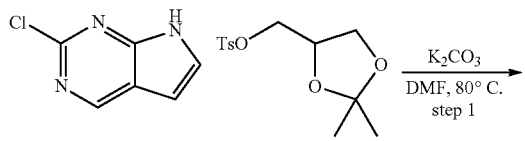

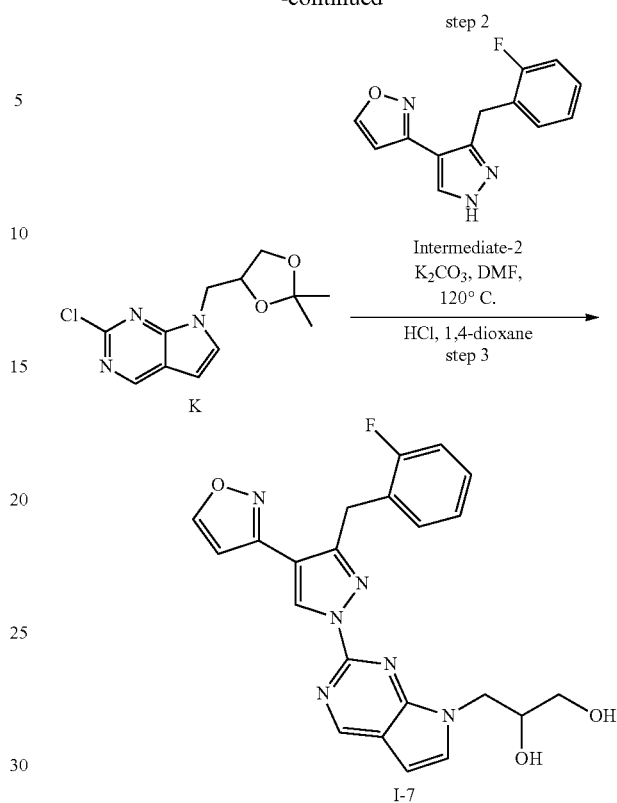

Step 1. Preparation of K

A mixture of 2-chloro-7H-pyrrolo[2,3-d]pyrimidine (0.94 g, 1 equiv.), potassium carbonate (1.1 g, 1.3 equiv.) and (2,2-dimethyl-1,3-dioxolan-4-yl)methyl 4-methylbenzenesulfonate (1.7 g, 1 equiv.) was heated at 80° C. in DMF (31 ml) for 24 h. The mixture was diluted in ethyl acetate (100 ml) and washed with water (50 ml). The organic layer was dried, filtered and evaporated to give an oil. The oil was purified by column chromatography (0 to 50% ethyl acetate in hexanes) to give 2-chloro-7-((2,2-dimethyl-1,3-dioxolan-4-yl)methyl)-7H-pyrrolo[2,3-d]pyrimidine (K, 1.2 g, 74% yield) as a white solid.

$^1$H NMR (500 MHz, CHLOROFORM-d) δ ppm 8.73 (s, 1H) 7.30 (d, 1H) 6.50 (d, 1H) 4.35-4.46 (m, 2H) 4.14-4.30 (m, 1H) 4.05 (dd, 1H) 3.62 (dd, 1H) 1.51 (s, 2H) 1.34 (s, 3H) 1.27 (s, 3H).

Step 2. Reaction of K with Intermediate-2

A mixture containing 3-(3-(2-fluorobenzyl)-1H-pyrazol-4-yl)isoxazole (Intermediate-2 162 mg, 1 equiv.), 2-chloro-7-((2,2-dimethyl-1,3-dioxolan-4-yl)methyl)-7H-pyrrolo[2,3-d]pyrimidine (K, 267 mg, 1.5 equiv.) and potassium carbonate (184 mg, 2 equiv.) in DMF (3.3 ml) was heated at 120° C. for 2 days. The mixture was diluted in ethyl acetate (100 ml) and washed with water (50 ml). The organic layer was dried, filtered and evaporated to give an oil. The oil was purified by column chromatography (0 to 80% ethyl acetate in hexanes) to give a residue containing the starting pyrazole and the desired product.

Step 3. Preparation of Compound I-7

Then, this residue was treated with HCl [4.0 M in 1,4-dioxane] (1.7 ml). The mixture was stirred at rt for 30 min.

The mixture was diluted in ethyl acetate (100 ml) and washed with 1N NaOH (50 ml). The organic layer was dried, filtered and evaporated to give a solid. The solid was purified by column chromatography (0 to 100% ethyl acetate in hexanes) to give Compound I-7 (50 mg, 17% yield over two steps) as a light yellow solid.

$^1$H NMR (500 MHz, DMSO-d$_6$) δ ppm 9.31 (s, 1H) 9.02 (s, 1H) 8.95 (d, 1H) 7.65 (d, 1H) 7.23-7.29 (m, 1H) 7.11-7.20 (m, 3H) 7.04-7.10 (m, 1H) 6.69 (d, 1H) 5.07 (d, 1H) 4.82 (t, 1H) 4.39 (s, 3H) 4.17-4.24 (m, 1H) 3.89-3.96 (m, 1H) 3.34-3.44 (m, 2H).

Compound I-8

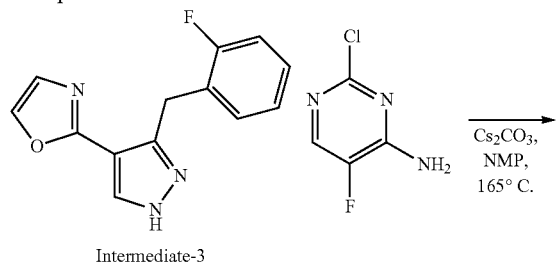

A mixture of 2-(3-(2-fluorobenzyl)-1H-pyrazol-4-yl)oxazole (Intermediate-3, 171 mg, 1 equiv.), cesium carbonate (275 mg, 1.2 equiv.) and 2-chloro-5-fluoropyrimidin-4-amine (104 mg, 1 equiv.) in NMP (3.5 ml) was heated at 165° C. for 18 h. The reaction was cooled to room temp and diluted in ethyl acetate (50 ml). The organic layer was washed with water (10 ml×2). The organic layer was dried, filtered and evaporated to give an oil. This oil was purified by column chromatography (0 to 80% ethyl acetate in hexanes) to give Compound I-8 (48 mg, 17% yield) as light yellow solid.

$^1$H NMR (400 MHz, DMSO-d$_6$) δ ppm 8.88 (s, 1H), 8.21 (d, 1H), 8.15 (d, 1H), 7.86 (br. s., 2H), 7.35-7.38 (m, 1H), 7.23-7.28 (m, 1H), 7.16-7.20 (m, 2H), 7.06-7.10 (m, 1H), 4.34 (s, 2H).

Compound I-9

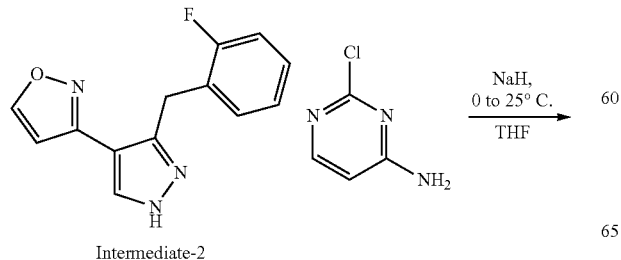

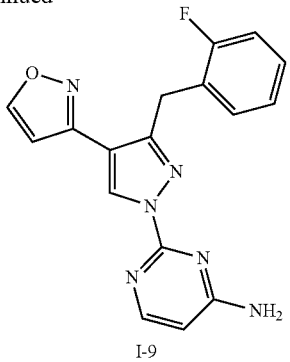

To a solution of 3-(3-(2-fluorobenzyl)-1H-pyrazol-4-yl)isoxazole (Intermediate-2, 354 mg, 1 equiv.) in THF (7.3 ml) at 25° C., was added sodium hydride (40 mg, 2 equiv.). To this mixture, was added 2-chloropyrimidin-4-amine (192 mg, 3 equiv). The resulting mixture was stirred at 80° C. for 24 h and then quenched with a saturated solution of ammonium chloride (50 ml) and extracted with ethyl acetate (100 ml). The organic layer was dried, filtered and evaporated to give a solid. This solid was purified by column chromatography (0 to 80% ethyl acetate in hexanes) and recrystallized from methanol. The solid was further purified by HPLC (5 to 95% acetonitrile in water) to give Compound I-9 (8 mg, 5% yield) as a white solid.

$^1$H NMR (500 MHz, METHANOL-d$_4$) δ ppm 9.04 (s, 1H) 8.70 (d, 1H) 8.02 (d, 1H) 7.19-7.26 (m, 1H) 7.13-7.19 (m, 1H) 6.99-7.09 (m, 2H) 6.75 (d, 1H) 6.59 (d, 1H) 4.45 (s, 2H).

Compound I-10

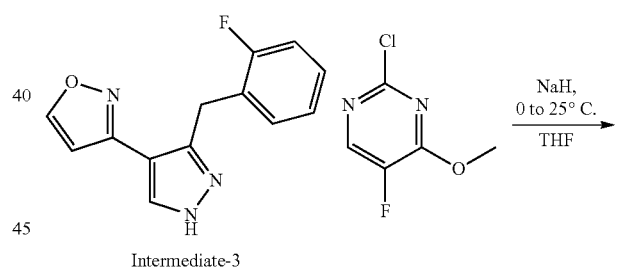

To a solution of 3-(3-(2-fluorobenzyl)-1H-pyrazol-4-yl)isoxazole (Intermediate-2, 354 mg, 1 equiv.) in THF (7 ml) at 25° C., was added sodium hydride [60 wt % dispersion on mineral oil](137 mg, 2.4 equiv.). The mixture was stirred until the bubbling ceased. To this mixture, was added 2-chloro-5-fluoro-4-methoxypyrimidine (473 mg, 2 equiv). The mixture was stirred at room temp for 24 h and then it was diluted with ethyl acetate (100 ml) and washed with 1N HCl (50 ml×3). The organic layer was dried, filtered and evaporated to give an oil. The oil was purified by column chromatography (0 to 100% ethyl acetate in hexanes) to give Compound I-10 (383 mg, 71% yield) as a white solid.

$^1$H NMR (500 MHz, METHANOL-$d_4$) δ ppm 9.06 (s, 1H) 8.63-8.69 (m, 1H) 8.45 (d, 1H) 7.16-7.26 (m, 1H) 6.97-7.14 (m, 3H) 6.76 (s, 1H) 4.44 (s, 2H) 4.25 (s, 3H).

Example 2

Biological Activity Measurement by the sGC-HEK-cGMP Assay (Assay Run with SNP Incubation)

Human embryonic kidney cells (HEK293), endogenously expressing soluble guanylate cyclase (sGC), were used to evaluate the activity of test compounds. Compounds stimulating the sGC receptor should cause an increase in the intracellular concentration of cGMP. HEK 293 cells were seeded in Dulbecco's Modification of Eagle's Medium supplemented with fetal bovine serum (10% final) and L-glutamine (2 mM final) in a 200 μL volume at a density of 1×10$^5$ cells/well in a poly-D-lysine coated 96 well flat bottom plate and grown overnight at 37° C. Medium was aspirated and cells were washed with 1× Hank's Buffered Saline Salt Solution (200 μL). Cells were then incubated for 15 minutes at 37° C. with 200 μL of a 0.5 mM 3-isobutyl-1-methylxanthine (IBMX) solution. Test article and sodium nitroprusside solutions (x μM concentration for test article solution and 10 μM concentration for SNP solution; wherein x is one of the following concentrations);

30 μM
10 μM
3 μM
1 μM
0.3 μM
0.1 μM
0.03 μM
0.01 μM
0.003 μM
0.001 μM
0.0003 M
0.0001 μM were then added to the assay mixture (2 μL each) and the resulting mixture incubated at 37° C. for 10 minutes. After the 10 minute incubation, the assay mixture was aspirated and 0.1M HCl (200 μL) was added to the cells. The plate was incubated at 4° C. for 30 minutes in the 0.1M HCl to stop the reaction and lyse the cells. The plates were then centrifuged at 1,200 g for 5 minutes at room temperature. Supernatants were collected and transferred to a new flat bottom 96 well plate for analysis by HPLC-MS. Vehicle controls were carried out using DMSO (1%) solutions. A known sGC stimulator, BAY 41-2272, was used as the positive control. Samples were diluted with an equal volume of 1 M Ammonium Acetate (pH 7) to neutralize samples for better chromatography. A 2×cGMP standard solution was prepared in 0.1 M HCl and then diluted with an equal volume of 1 M Ammonium Acetate, with the following final concentrations in nM: 1024, 512, 256, 128, 64, 32, 16, 8, 4, 2, 1. cGMP concentrations in the test plates were determined from each sample using the LC/MS conditions shown in Table 2 below and the calculated cGMP standard curve. $EC_{50}$ values were calculated from concentration-response curves generated with GraphPad Prism Software.

The biological activities of some of the compounds of Formula I or Formula Ib determined with the sGC-HEK assay with SNP incubation are summarized in Tables 3A and 3B.

TABLE 2

(HPLC LC/MS experimental conditions)

| MS: | Thermo Quantum or Waters LCMS |
| --- | --- |
| Ion Mode: | ESI$^+$ |
| Scan Type: | MRM |

| Compound: | Transition | Dwell Time (msec) | Collision Energy (V) | Tube Lens | Retention Time (min) |
| --- | --- | --- | --- | --- | --- |
| cGMP | 346 > 152 | 100 | 28 | 139 | 1.0 |
| HPLC: | Agilent Technologies 1200 Series with CTC Analytics HTS PAL | | | | |
| Column: | Thermo Hypersil Gold 2.1 × 50 mm 5 micron particle size | | | | |
| Flow Rate: | 400 uL/min | | | | |
| Column Temperature: | RT | | | | |
| Autosampler Temperature: | 6° C. | | | | |
| Injection Volume: | 20 uL | | | | |
| Mobile Phases: | A = 98:2 Water:Acetonitrile + 0.1% Formic Acid B = 2:98 Water:Acetonitrile + 0.1% Formic Acid | | | | |

| Gradient: | Time (min) | % A | % B |
| --- | --- | --- | --- |
| | 0 | 100 | 0 |
| | 0.3 | 30 | 70 |

TABLE 2-continued (HPLC LC/MS experimental conditions)

| | | |
|---|---|---|
| 2.00 | 30 | 70 |
| 2.01 | 100 | 0 |
| 4 | 100 | 0 |

TABLE 3A

Whole cell activity in the HEK assay.

| Compound No. | HEK assay (Percent Emax at 1 μM)* | HEK assay (Percent Emax at 10 μM)* | HEK assay (Percent Emax at 30 μM)* | HEK assay Emax-unconstrained (Percent)+ |
|---|---|---|---|---|
| I-1 | E | F | F | F |
| I-2 | — | F | F | — |
| I-3 | — | — | — | — |
| I-4 | F | G | G | G |
| I-8 | — | E | E | — |
| I-9 | E | F | F | F |
| I-10 | C | C | C | C |

*Percent Emax was obtained at twelve concentrations of the test compound as explained above; the results for three of them (1, 10 and 30 μM) are shown in Table 3A. The code definitions for the sGC enzyme activity values, expressed as % $E_{max}$ in the presence of 10 μM of SNP (wherein $E_{max}$ = 100% was the activity in the HEK assay obtained with the positive control BAY 41-2272 at 10 μM in the presence of 100 μM SNP) are:
A = 0 to <10%
B = 10 to <20%
C = 20 to <40%
D = 40 to <60
E = 60 or <80%
F = 80 to <100%
G = 100 to <120%
H = 120% or higher
— = not determined
+ The same code definitions apply for Emax unconstrained, wherein this value is defined as the maximum activity value obtained from the full concentration-response curve for the compound, relative to the positive control value of 100% obtained as above. Here, the term "unconstrained" means that, during analysis of the sGC enzyme activity data, the top portion of the concentration-response curve was not fitted to 100%.

TABLE 3B

More whole cell activity in the HEK assay.

| Compound No. | HEK assay EC50-constrained (μM)# | HEK assay EC50-unconstrained (μM)# |
|---|---|---|
| I-1 | — | A |
| I-2 | D | — |
| I-3 | — | — |
| I-4 | — | A |
| I-8 | — | — |
| I-9 | — | B |
| I-10 | — | C |

$EC_{50}$ values were obtained from the full concentration response curve following two methods: EC50 constrained refers to the value obtained when the top of the curve was fitted to 100% (wherein $E_{max}$ = 100% was the activity in the HEK assay obtained with the positive control BAY 41-2272 at 10 μM in the presence of 100 μM SNP); $EC_{50}$ unconstrained here repored refer to the value obtained from a full concentration-response curve when the top of the curve is not fitted to 100%. The EC50 code definitions in micromolar (μM) are:
0.01 ≤ EC50 < 0.1 = A
0.1 ≤ EC50 < 0.5 = B
0.5 ≤ EC50 < 1.0 = C
1.0 ≤ EC50 < 5.0 = D
5.0 ≤ EC50 < 10.0 = E
EC50 ≥ 10.0 = F Example 2B, HEK whole cell assay using HTRF procedure (Assay Run with SNP Incubation)

Human embryonic kidney cells (HEK293), endogenously expressing soluble guanylate cyclase (sGC), were used to evaluate the activity of test compounds. Compounds stimulating the sGC enzyme should cause an increase in the intracellular concentration of cGMP. HEK 293 cells were seeded in Dulbecco's Modification of Eagle's Medium supplemented with fetal bovine serum (10% final) and L-glutamine (2 mM final) in a 200 μL volume at a density of $1 \times 10^5$ cells/well in a poly-D-lysine coated 96 well flat bottom plate and grown overnight at 37° C. Medium was aspirated and cells were washed with 1× Hank's Buffered Saline Salt Solution (200 μL). Cells were then incubated for 15 minutes at 37° C. with 200 μL of a 0.5 mM 3-isobutyl-1-methylxanthine (IBMX) solution. Test article and sodium nitroprusside solutions (x μM concentration for test article solution and 10 μM concentration for SNP solution; wherein x is one of the following concentrations);

30 μM

10 μM

3 μM

1 μM 0.3 μM 0.1 μM 0.03 μM 0.01 μM 0.003 μM 0.001 μM 0.0003 μM 0.01 μM were then added to the assay mixture (2 μL each) and the resulting mixture incubated at 37° C. for 10 minutes. After the 10 minute incubation, the assay mixture was aspirated and 0.1M HCl (200 μL) was added to the cells. The plate was incubated at 4° C. for 30 minutes in the 0.1M HCl to stop the reaction and lyse the cells. The plates were then centrifuged at 1,200 g for 5 minutes at room temperature.

cGMP levels were determined using a cGMP HTRF assay (Cisbio Product #62GM2PEC). For each sample, 5 uL of HEK assay supernatant was diluted 1:5 in HTRF kit assay diluent and transferred to a well of the assay plate, and the HTRF assay was performed according to the HTRF kit manufacturer's instructions. Sample calculations were performed using high and low controls, where high control was supernatant from HEK assay performed in the presence of 10 uM Bay 41-2272+100 uM SNP, and the low control was the supernatant from the HEK assay performed in the presence of vehicle. A cGMP standard solution was prepared in 0.1 M HCl and diluted in order to perform a cGMP standard curve using the HTRF assay. Using Mean Ratio data from the HTRF assay, sample date were normalized according to the equation: 100*(Sample−Low Control)/(High Control−Low Control). Data were fit to a 3-parameter log agonist dose response (Top (% EMax), Bottom, log EC50) using Graphpad (Prism Software). Data in Table 3C was obtained using this modified assay procedure.

TABLE 3C

| Compound No. | HEK assay EC50-unconstrained (μM)# | HEK assay Emax-unconstrained (Percent)+ |
|---|---|---|
| I-5 | B | F |
| I-6 | B | F |
| I-7 | B | F |

EC$_{50}$ values were obtained from the full concentration response curve following two methods: EC50 constrained refers to the value obtained when the top of the curve was fitted to 100% (wherein E$_{max}$ = 100% was the activity in the HEK assay obtained with the positive control BAY 41-2272 at 10 μM in the presence of 100 μM SNP); EC$_{50}$ unconstrained here repored refer to the value obtained from a full concentration-response curve when the top of the curve is not fitted to 100%. The EC50 code definitions in micromolar (μM) are:
0.01 ≤ EC50 < 0.1 = A
0.1 ≤ EC50 < 0.5 = B
0.5 ≤ EC50 < 1.0 = C
1.0 ≤ EC50 < 5.0 = D
5.0 ≤ EC50 < 10.0 = E
EC50 ≥ 10.0 = F
+ % E$_{max}$ in the presence of 10 μM of SNP (wherein E$_{max}$ = 100% was the activity in the HEK assay obtained with the positive control BAY 41-2272 at 10 μM in the presence of 100 μM SNP) are:
A = 0 to <10%
B = 10 to <20%
C = 20 to <40%
D = 40 to <60
E = 60 or <80%
F = 80 to <100%
G = 100 to <120%
H = 120% or higher
— = not determined
wherein Emax unconstrained is defined as the maximum activity value obtained from the full concentration-response curve for the compound, relative to the positive control value of 100% obtained as above. Here, the term "unconstrained" means that, during analysis of the sGC enzyme activity data, the top portion of the concentration-response curve was not fitted to 100%.

Example 3A

Biological Activity Measurements by the Purified Human sGC Enzyme Activity Assay Human soluble guanylate cyclase enzyme (hsGC) obtained from Enzo Inc. (P/N: ALX-201-177) was used to evaluate the activity of test compounds. The assay reactions contained 0.1 M Tris (pH 8.0), 0.5 mg/mL BSA (pH 8.0), 2 mM DTT, 2 mM MgCl$_2$, 300 μM GTP, 1 mM 3-isobutyl-1-methylxanthine (IBMX) and 5 ng human soluble guanylate cyclase enzyme. Test compounds in DMSO were then added (2 μL, 10 or 30 μM final concentration) and incubated (water, 200 μL, 96-well plate format) at 37° C. for 30 minutes. The controls were carried out using 2 μL DMSO. After the 30 minute incubation, the reaction was stopped with the addition of 200 μL of cold methanol. The plate was then centrifuged at 3,200 rpm for 10 minutes at room temperature. Supernatants (200 μL) were collected and transferred to a new 96 well plate for analysis by HPLC LC/MS/MS.

An 8 point cGMP (Sigma-Aldrich P/N: G6129) standard curve was prepared in assay buffer ranging from 0.156-20 μM. Samples for the cGMP standard curve were then diluted with an equal volume of methanol resulting in final cGMP concentrations of 0.078-10 μM.

cGMP concentrations in all samples were determined using LC/MS/MS analysis, using the conditions listed in Table 4 below. The cGMP standard curve was generated using GraphPad Prism Software.

Calculations: Specific Activity was determined by the amount of cGMP formed (nmoles) per mg of sGC per min. Enzyme "fold-change" was calculated by dividing Specific Activity for test compounds by Specific Activity of DMSO controls.

TABLE 4

LC/MS/MS method for detection of cGMP

Inlet Method:

| | |
|---|---|
| HPLC: | Waters Acquity |
| Column: | Thermo Hypersile Gold PFP, 2.1 × 30 mm, 3 μm |
| Guard Column: | Thermo Hypersile Gold, 2.1 × 10 mm |
| Column Temp: | 25° C. |
| Flow Rate: | 0.4 mL/min |
| Auto sampler: | Acquity; 6° C. |
| Injection Volume: | 10 uL |
| Mobile Phases: | A = 0.1% Acetic Acid (v/v) in 100% water |
| | B = 0.1% Acetic Acid (v/v) in 100 methanol |

| Gradient: | Time (min) | % A | % B | Curve |
|---|---|---|---|---|
| | 0 | 95 | 5 | 6 |
| | 0.5 | 95 | 5 | 6 |
| | 0.6 | 10 | 90 | 6 |
| | 2.0 | 10 | 90 | 6 |
| | 2.1 | 95 | 5 | 6 |
| | 4 | (end) | | |

MS File: eGmF.exp

| | |
|---|---|
| Mass Spectrum: | Waters Quattro micro |
| Ionization: | ES + |
| Source, Desolvation: | 150° C., 450° C. |
| MS Function: | MRM |

| Compound | Transition | Dwell (sec) | Cone (V) | Collision Energy (eV) |
|---|---|---|---|---|
| cGMP | 346 > 152 | 0.1 | 35 | 20 |

Example 3B

Biological Measurement by the Purified Human sGC Enzyme Synergy Performed in the Presence of Sodium Nitroprusside (SNP), a Nitric Oxide Donor Enzyme assays were performed as described above, but the assay was done in the presence of 1 μM sodium nitroprusside (SNP). Data for compounds of Table 1 is summarized in Table 5 below.

TABLE 5

Enzyme Data With and without SNP.*

| Compound No. | Enzyme Activity (increase at 30 μM without SNP)* | Enzyme Activity (increase at 30 μM with SNP)* |
|---|---|---|
| I-2 | C | D |
| I-8 | C | E |

*The compounds were tested at a concentration of 30 μM in the presence of 1 μM SNP. The code for the fold increase in enzyme activity is:
A = no increase to <2 fold increase
B = 2 to <5 fold increase
C = 5 to <10 fold increase
D = 10 or <20 fold increase
E = 20 to 30 fold increase
F = >30 fold increase

Example 4

Biological Activity Measurement by the Thoracic Aortic Rings Assay

Thoracic aortic rings were dissected from anesthetized (isoflurane) male Sprague-Dawley rats weighing 275-299 g. Tissues were immediately transferred to ice-cold Krebs-Henseleit solution, which had been aerated with 95% $O_2$ and 5% $CO_2$ for 30 minutes. Following removal of connective tissue, aortic sections were cut into 4 rings (~2 mm each) and suspended on 2 L-shaped hooks, with one hook fixed at the bottom of the tissue bath (Schuler Organ Bath, Harvard Apparatus) and the other connected to a force transducer (F30 Force Transducer, Harvard Apparatus). Baths contained Krebs Henseleit solution (10 mL) heated to 37° C. and aerated with 95% $O_2$ and 5% $CO_2$. Rings were brought to an initial tension of 0.3-0.5 g and gradually raised to a resting tension of 1.0 g over 60 minutes. Rings were rinsed with Krebs Henseleit solution (heated to 37° C. and aerated with 95% 02 and 5% $CO_2$) at 15 minute intervals until a stable baseline was obtained. Rings were considered to be stable after a resting tension of 1.0 g was maintained (for approximately 10 minutes) without need for adjustment. Rings were then contracted with 100 ng/mL phenylephrine by adding 100 uL of a 10 g/mL phenylephrine stock solution. Tissues achieving a stable contraction were then treated in a cumulative, dose dependent manner with test compounds prepared in dimethylsulfoxide (DMSO). In some cases, tissues were rinsed three times over a 5 minute period with Krebs-Heinseleit's solution (heated to 37° C. and aerated with 95% 02 and 5% $CO_2$), allowed to stabilize at baseline, and then used for characterization of other test articles or DMSO effects. All data were collected using the HSE-ACAD software provided by Harvard Apparatus. Percent relaxation effects were calculated in Microsoft Excel using the recorded tension value of 100 ng/mL phenylephrine treatment as 0% inhibition and treatment with 100 μM 3-isobutyl-1-methylxanthine as 100% inhibition. $EC_{50}$ values were calculated from concentration-response curves generated with GraphPad Prism Software.

Example 5

Biological Activity Measurement by the Thoracic Aortic Rings Assay

As an alternative thoracic aortic rings assay, the procedure of Example 5 was used except that percent relaxation effects were calculated in Microsoft Excel using the recorded tension value of 100 ng/mL phenylephrine treatment as 0% inhibition and, after washing the tissue with buffer, the original resting tension of the tissue was used as 100% inhibition.

The biological data for some of the compounds of Formula I or Formula Ib, in comparison with the known compound, BAY 41-2272, as the reference compound, determined by the thoracic aorta ring assay of Example 5 are presented in Table 6 below.

TABLE 6

Thoracic Aortic Ring Assay Results.

| Compound No. | Aortic Ring Percent Relaxation at 1 μM* | Aortic Ring Percent Relaxation at 3 μM* | Aortic Ring Percent Relaxation at 10 μM* | Aortic Ring EC50 (μM)** |
|---|---|---|---|---|
| I-1 | — | — | — | — |
| I-2 | E | F | G | A |

*The compounds were tested at a concentration of 1, 3 or 10 μM to obtain data using the method described in Example 5. The code for the percent relaxation of the aotic ring is:
A = 0 to <10%
B = 10 to <20%
C = 20 to <40%
D = 40 to <60%
E = 60 or <80%
F = 80 to <100%
G = 100 to <120%
H = higher than 120%
**The code for the $EC_{50}$ value obtained is:
A = 0 to <2 μM
B = 2 to <4 μM
C = 4 to <8 μM
D = 8 to <12 μM A number of embodiments have been described. Nevertheless, it will be understood that various modifications may be made without departing from the spirit and scope of the invention.

Example 6

Animal Models Descriptions

Lamb Model of Pulmonary Hemodynamics Using Inhaled sGC Stimulator ("Inhaled Agonists of Soluble Guanylate Cyclase Induce Selective Pulmonary Vasodilation", Oleg V. et al, American J of Resp and Critical Care Medicine, Vol 176, 2007, p 1138)

It is possible to test whether inhalation of novel dry-powder microparticle formulations containing sGC stimulators would produce selective pulmonary vasodilation in lambs with acute pulmonary hypertension by following a published procedure. It is also possible to evaluate the combined administration of the microparticles of sGC stimulator and inhaled nitric oxide (iNO) in this system. Finally, it is possible to examine whether inhaling microparticles of an sGC stimulator would produce pulmonary vasodilation when the response to iNO (inducible nitric oxide synthase) is impaired.

Protocol: In awake, spontaneously breathing lambs instrumented with vascular catheters and a tracheostomy tube, U-46619 is infused intravenously to increase mean pulmonary arterial pressure to 35 mm Hg. Inhalation of microparticles composed of either BAY 41-2272, BAY 41-8543, or BAY 58-2667 and excipients (dipalmitoylphosphatidylcholine, albumin, lactose) produced dose dependent pulmonary vasodilation and increased transpulmonary cGMP release without significant effect on mean arterial pressure. Inhalation of microparticles containing BAY 41-8543 or BAY 58-2667 increased systemic arterial oxygenation. The magnitude and duration of pulmonary vasodilation induced by iNO were augmented after inhaling BAY 41-8543 microparticles. Intravenous administration of 1H-[1,2,4]oxadiazolo[4,3-a]quinoxalin-1-one (ODQ), which oxidizes the prosthetic heme group of sGC, markedly reduced the pulmonary vasodilator effect of iNO. In contrast, pulmonary vasodilation and transpulmonary cGMP release induced by inhaling BAY 58-2667 microparticles were greatly enhanced after treatment with ODQ. Thus, inhalation of microparticles containing agonists of sGC may provide an effective novel treatment for patients with pulmonary hypertension, particularly when responsiveness to iNO is impaired by oxidation of sGC. Note: BAY 41-2272, BAY 41-8543 are sGC stimulators whereas BAY 58-2667 is an sGC activator.

Electrical Field Stimulated Guinea Pig Tracheal Smooth Muscle In Vitro (Ex Vivo) Model for the Assessment of Bronchodilation.

It is possible to assess the bronchodilating effects of sGC stimulators by using the system described below. This system allowed us to determine potency, efficacy and duration of action of several sGC stimulators, as well as to assess potential side effects such as blood pressure, or heart rate changes.

Animals: Guinea pig, Dunkin Hartley, male, Full barrier-bred and certified free of specific micro-organisms on receipt 525-609 g on the experimental day, Harlan UK Ltd. Guinea pigs were housed in a group of 4 in solid-bottomed cages with Gold Flake bedding in a controlled environment (airflow, temperature and humidity). Food (FD1, Special Diet Services) and water were provided ad libitum.

Guinea Pig Tracheal Smooth Muscle Contraction in Response to EFS. Assessment of Compound Potency and Efficacy:

On each experimental day, a guinea pig was killed by exposure to a rising concentration of CO2 and the trachea removed. The trachea was cleaned of extraneous tissue and cut open longitudinally in a line opposite the muscle, opened out and cut into strips 2-3 cartilage rings wide. A cotton loop was attached to one end of each tracheal strip and a length of cotton to the other end. Tracheal strips were then suspended between two platinum electrodes, using tissue holders, in a Myobath system (World Precision Instruments Stevenage, UK). The loop was attached over the hook at the bottom of the tissue holder and the other end attached to the arm of a FORT 10 force transducer (World Precision Instruments Stevenage, UK) ensuring that the tissue was positioned between the two platinum electrodes. The whole assembly was then lowered into a 10 ml tissue bath containing modified Kreb's-Henseleit buffer, at 37° C., bubbled with Carbogen. A 1 g tension was applied to each piece of tissue and the tissue washed, followed by a 1 hour stabilization period. Once the tissues had been allowed to stabilize, the apparatus for electrical field stimulation was set to deliver a stimulation of frequency 80 Hz pulse width 0.1 ms, with a gated, uni-polar pulse, every 2 minutes using a DS8000 8 channel digital stimulator (World Precision Instruments Stevenage, UK). A voltage response curve was carried out on each tracheal strip at 2, 4, 6, 7, 8, 10, 12 V and a sub-maximal voltage then selected to apply to each tissue during the remainder of the experiment. Guinea pig tracheal smooth muscle (GPTSM) contraction was induced using sub-maximal Electrical Field Stimulation (EFS) (It is also possible to induce contraction by using a spasmogen substance, such as methacholine or histamine as described in Coleman et al.*). Compounds were dissolved in 100% DMSO at 3×10-2M and aliquots stored at –200 C. A separate aliquot was used for each experiment. Tissues were washed with Kreb's buffer and stimulated using the previously determined sub-maximal voltage for 1 hour to establish a stable baseline contraction prior to assessment of compound activity.

A cumulative dose response curve (DRC) to each test substance was then performed and changes in smooth muscle contraction measured. The effect of each test substance in each experiment was expressed as a percentage inhibition of the baseline contraction, normalized to the relevant vehicle controls. The experiment was performed three times, using tissue from three different animals. The data from all three experiments was pooled, the DRC plotted, and the test substance potency and efficacy determined. The potency of Ipratropium bromide was assessed alongside the test compounds and the IC50 determined to be 0.86 nM (95% Cl, 0.78-0.94), in agreement with data previously produced in the system.

*"Novel and Versatile Superfusion System. Its use in the Evaluation of Some Spasmogenic and Spasmolytic Agents Using Guinea pig isolated Tracheal Smooth Muscle.", R. A. Coleman et al., J. Pharmacol. Methods, 21, 71-86, 1989.

The invention claimed is:

1. A compound represented by Formula I, or a pharmaceutically acceptable salt thereof:

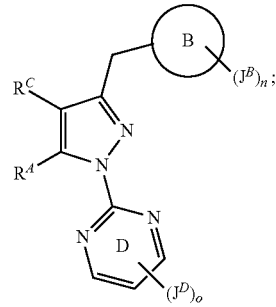

Formula I wherein, ring B is a phenyl or a 5 or 6-membered heteroaryl ring, containing 1 or 2 ring heteroatoms selected from N, O or S;

n is an integer selected from 0 to 3;

each $J^B$ is independently selected from halogen, —CN, a $C_{1-6}$ aliphatic, $OR^B$ or a $C_{3-8}$ cycloaliphatic group; wherein each said $C_{1-6}$ aliphatic and each said $C_{3-8}$ cycloaliphatic group is optionally and independently substituted with up to 3 instances of $R^3$;

each $R^B$ is independently selected from hydrogen, a $C_{1-6}$ aliphatic or a $C_{3-8}$ cycloaliphatic;

wherein each said $C_{1-6}$ aliphatic and each said $C_{3-8}$ cycloaliphatic ring is optionally and independently substituted with up to 3 instances of $R^{3a}$;

each $R^3$ is independently selected from halogen, —CN, $C_{1-4}$ alkyl, $C_{1-4}$ haloalkyl, —O($C_{1-4}$ alkyl) or —O($C_{1-4}$ haloalkyl);

each $R^{3a}$ is independently selected from halogen, —CN, $C_{1-4}$ alkyl, $C_{1-4}$ haloalkyl, —O($C_{1-4}$ alkyl) or —O($C_{1-4}$ haloalkyl);

o is an integer selected from 0 to 3;

each $J^D$ is independently selected from halogen, —NO$_2$, —OR$^D$, —SR$^D$, —C(O)R$^D$, —C(O)OR$^D$, —C(O)N(R$^D$)$_2$, —CN, —N(R$^D$)$_2$, —N(R$^d$)C(O)R$^D$, —N(R$^d$)C(O)OR$^D$, —SO$_2$R$^D$, —SO$_2$N(R$^D$)$_2$, —N(R$^d$)SO$_2$R$^D$, a $C_{1-6}$ aliphatic, —($C_{1-6}$ aliphatic)-R$^D$, a $C_{3-8}$ cycloaliphatic ring, a 6 to 10-membered aryl ring, a 4 to 8-membered heterocyclic ring or a 5 to 10-membered heteroaryl ring; wherein each said 4 to 8-membered heterocyclic ring and each said 5 to 10-membered heteroaryl ring contains between 1 and 3 heteroatoms independently selected from O, N or S; and wherein each said $C_{1-6}$ aliphatic, each said $C_{3-8}$ cycloaliphatic ring, each said 6 to 10-membered aryl ring, each said 4 to 8-membered heterocyclic ring and each said 5 to 10-membered heteroaryl ring is optionally and independently substituted with up to 3 instances of $R^5$;

each $R^D$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said 4 to 8-membered heterocylic ring and each said 5 to 6-membered heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted with up to 3 instances of $R^{5a}$;

each $R^d$ is independently selected from hydrogen, a $C_{1-6}$ aliphatic, —($C_{1-6}$ aliphatic)-$R^f$, a $C_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said $C_{1-6}$ aliphatic, each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^{5b}$;

each $R^f$ is independently selected from a $C_{3-8}$ cycloaliphatic ring, a 4 to 8-membered heterocyclic ring, phenyl or a 5 to 6-membered heteroaryl ring; wherein each said heterocylic ring and each said heteroaryl ring contains between 1 and 3 heteroatoms independently selected from O, N or S; and wherein each said $C_{3-8}$ cycloaliphatic ring, each said 4 to 8-membered heterocyclic ring, each said phenyl and each said 5 to 6-membered heteroaryl ring is optionally and independently substituted by up to 3 instances of $R^{5c}$;

when $J^D$ is —C(O)N($R^D$)$_2$, —N($R^D$)$_2$ or —SO$_2$N($R^D$)$_2$, the two $R^D$ groups together with the nitrogen atom attached to the $R^D$ groups alternatively form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;

when $J^D$ is —N($R^d$)C(O)$R^D$, the $R^D$ group together with the carbon atom attached to the $R^D$ group, with the nitrogen atom attached to the $R^d$ group, and with the $R^d$ group alternatively form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;

when $J^D$ is —N($R^d$)C(O)O$R^D$, the $R^D$ group together with the oxygen atom attached to the $R^D$ group, with the carbon atom of the —C(O)— portion of the —N($R^d$)C(O)O$R^D$ group, with the nitrogen atom attached to the $R^d$ group, and with the $R^d$ group alternatively form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;

when $J^D$ is —N($R^d$)SO$_2$RD, the $R^D$ group together with the oxygen atom attached to the $R^D$ group, with the sulfur atom attached to said oxygen atom in the —SO$_2$$R^D$ portion of the —N($R^d$)SO$_2$$R^D$ group, with the nitrogen atom attached to the $R^d$ group, and with the $R^d$ group alternatively form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of $R^5$;

each $R^5$ is independently selected from halogen, —CN, —NO$_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, —O$R^6$, —S$R^6$, —OCO$R^6$, —CO$R^6$, —C(O)O$R^6$, —C(O)N($R^6$)$_2$, —N($R^6$)C(O)$R^6$, —N($R^6$)$_2$, —SO$_2$$R^6$, —SO$_2$N($R^6$)$_2$, —N($R^6$)SO$_2$$R^6$, phenyl or an oxo group; wherein each said phenyl group is optionally and independently substituted with up to 3 instances of halogen, —OH, —NH$_2$, —NH($C_{1-4}$ alkyl), —N($C_{1-4}$ alkyl)$_2$, —NO$_2$, —CN, $C_{1-4}$ alkyl, $C_{1-4}$ haloalkyl, —O($C_{1-4}$ alkyl) or —O($C_{1-4}$ haloalkyl); and wherein each said $C_{7-12}$ aralkyl and each said cycloalkyl group is optionally and independently substituted with up to 3 instances of halogen;

each $R^{5a}$ is independently selected from halogen, —CN, —NO$_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, —O$R^6$, —S$R^6$, —OCO$R^6$, —CO$R^6$, —C(O)O$R^6$, —C(O)N($R^6$)$_2$, —N($R^6$)C(O)$R^6$, —N($R^6$)$_2$, —SO$_2$$R^6$, —SO$_2$N($R^6$)$_2$, —N($R^6$)SO$_2$$R^6$, phenyl or an oxo group; wherein each said phenyl group is optionally and independently substituted with up to 3 instances of halogen, —OH, —NH$_2$, —NH($C_{1-4}$ alkyl), —N($C_{1-4}$ alkyl)$_2$, —NO$_2$, —CN, $C_{1-4}$ alkyl, $C_{1-4}$ haloalkyl, —O($C_{1-4}$ alkyl) or —O($C_{1-4}$ haloalkyl); and wherein each said $C_{7-12}$ aralkyl and each said cycloalkyl group is optionally and independently substituted with up to 3 instances of halogen;

each $R^{5b}$ is independently selected from halogen, —CN, —NO$_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, —O$R^6$, —S$R^6$, —OCO$R^6$, —CO$R^6$, —C(O)O$R^6$, —C(O)N($R^6$)$_2$, —N($R^6$)C(O)$R^6$, —N($R^6$)$_2$, —SO$_2$$R^6$, —SO$_2$N($R^6$)$_2$, —N($R^6$)SO$_2$$R^6$, phenyl or an oxo group; wherein each said phenyl group is optionally and independently substituted with up to 3 instances of halogen, —OH, —NH$_2$, —NH($C_{1-4}$ alkyl), —N($C_{1-4}$ alkyl)$_2$, —NO$_2$, —CN, $C_{1-4}$ alkyl, $C_{1-4}$ haloalkyl, —O($C_{1-4}$ alkyl) or —O($C_{1-4}$ haloalkyl); and wherein each said $C_{7-12}$ aralkyl and each said cycloalkyl group is optionally and independently substituted with up to 3 instances of halogen;

each $R^{5c}$ is independently selected from halogen, —CN, —NO$_2$, $C_{1-4}$ alkyl, a $C_{7-12}$ aralkyl, $C_{3-8}$ cycloalkyl ring, $C_{1-4}$ haloalkyl, $C_{1-4}$ cyanoalkyl, —O$R^6$, —S$R^6$, —OCO$R^6$, —CO$R^6$, —C(O)O$R^6$, —C(O)N($R^6$)$_2$, —N($R^6$)C(O)$R^6$, —N($R^6$)$_2$, —SO$_2$$R^6$, —SO$_2$N($R^6$)$_2$, —N($R^6$)SO$_2$$R^6$, phenyl or an oxo group; wherein each said phenyl group is optionally and independently substituted with up to 3 instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl); and wherein each said C$_{7-12}$ aralkyl and each said cycloalkyl group is optionally and independently substituted with up to 3 instances of halogen;

each R$^6$ is independently selected from hydrogen, a C$_{1-4}$ alkyl, a C$_{2-4}$ alkenyl, phenyl, a C$_{7-12}$ aralkyl or a C$_{3-8}$ cycloalkyl ring; wherein each said C$_{1-4}$ alkyl, each said C$_{2-4}$ alkenyl, each said phenyl, each said C$_{7-12}$ aralkyl and each said cycloalkyl group is optionally and independently substituted with up to 3 instances of halogen;

alternatively, two instances of R$^6$ linked to the same nitrogen atom of R$^5$, together with said nitrogen atom of R$^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; or alternatively, one instance of R$^6$ linked to a nitrogen atom of R$^5$ and one instance of R$^6$ linked to a carbon or sulfur atom of the same R$^5$, together with said nitrogen and said carbon or sulfur atom of the same R$^5$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S;

or, alternatively, two J$^D$ groups attached to two vicinal ring D atoms, taken together with said two vicinal ring D atoms, form a 5 to 7-membered heterocycle resulting in a fused ring D wherein said 5 to 7-membered heterocycle contains from 1 to 3 heteroatoms independently selected from N, O or S; and wherein said 5 to 7-membered heterocycle is optionally and independently substituted by up to 3 instances of halogen, —OH, —NH$_2$, —NH(C$_{1-4}$ alkyl), —N(C$_{1-4}$ alkyl)$_2$, —CN, C$_{1-4}$ alkyl, C$_{1-4}$ haloalkyl, —O(C$_{1-4}$ alkyl), —O(C$_{1-4}$ haloalkyl), oxo or phenyl; wherein said phenyl is optionally and independently substituted by up to three instances of halogen, —OH, —NH$_2$, —NH(C$_{1-4}$ alkyl), —N(C$_{1-4}$ alkyl)$_2$, —NO$_2$, —CN, C$_{1-4}$ alkyl, C$_{1-4}$ haloalkyl, —O(C$_{1-4}$ alkyl) or —O(C$_{1-4}$ haloalkyl);

R$^C$ is a ring C; ring C is a phenyl ring, a monocyclic 5 or 6-membered heteroaryl ring, a bicyclic 8 to 10-membered heteroaryl ring, a monocyclic 3 to 10-membered cycloaliphatic ring, or a monocyclic 4 to 10-membered heterocycle; wherein said monocyclic 5 or 6-membered heteroaryl ring, said bicyclic 8 to 10-membered heteroaryl ring, or said monocyclic 4 to 10-membered heterocycle contain between 1 and 4 heteroatoms selected from N, O or S; wherein said monocyclic 5 or 6-membered heteroaryl ring is not a 1,3,5-triazinyl ring; and wherein said phenyl, monocyclic 5 to 6-membered heteroaryl ring, bicyclic 8 to 10-membered heteroaryl ring, monocyclic 3 to 10-membered cycloaliphatic ring, or monocyclic 4 to 10-membered heterocycle is optionally and independently substituted with up to 3 instances of J$^C$;

each J$^C$ is independently selected from halogen, —CN, —NO$_2$, a C$_{1-6}$ aliphatic, —OR$^H$, —SR$^H$, —N(R$^H$)$_2$, a C$_{3-8}$ cycloaliphatic ring or a 4 to 8-membered heterocyclic ring; wherein said 4 to 8-membered heterocyclic ring contains 1 or 2 heteroatoms independently selected from N, O or S; wherein each said C$_{1-6}$ aliphatic, each said C$_{3-8}$ cycloaliphatic ring and each said 4 to 8-membered heterocyclic ring, is optionally and independently substituted with up to 3 instances of R$^7$; or alternatively, two J$^C$ groups attached to two vicinal ring C atoms, taken together with said two vicinal ring C atoms, form a 5 to 7-membered heterocycle resulting in a fused ring C; wherein said 5 to 7-membered heterocycle contains from 1 to 2 heteroatoms independently selected from N, O or S;

each R$^H$ is independently selected from hydrogen, a C$_{1-6}$ aliphatic, a C$_{3-8}$ cycloaliphatic ring or a 4 to 8-membered heterocyclic ring; wherein each said 4 to 8-membered heterocyclic ring contains between 1 and 3 heteroatoms independently selected from O, N or S; and wherein each said C$_{1-6}$ aliphatic, each said C$_{3-8}$ cycloaliphatic ring, each said 4 to 8-membered heterocyclic ring, is optionally and independently substituted with up to 3 instances of R$^{7a}$;

alternatively, two instances of R$^H$ linked to the same nitrogen atom of J$^C$, together with said nitrogen atom of J$^C$, form a 4 to 8-membered heterocyclic ring or a 5-membered heteroaryl ring; wherein each said 4 to 8-membered heterocyclic ring and each said 5-membered heteroaryl ring optionally contains up to 2 additional heteroatoms independently selected from N, O or S, and wherein each said 4 to 8-membered heterocyclic ring and each said 5-membered heteroaryl ring is optionally and independently substituted by up to 3 instances of R$^{7b}$;

each R$^7$ is independently selected from halogen, —CN, —NO$_2$, C$_{1-4}$ alkyl, C$_{1-4}$ haloalkyl, C$_{3-8}$ cycloalkyl ring, —OR$^8$, —SR$^8$, —N(R$^8$)$_2$, or an oxo group; wherein each said cycloalkyl group is optionally and independently substituted with up to 3 instances of halogen;

each R$^{7a}$ is independently selected from halogen, —CN, —NO$_2$, C$_{1-4}$ alkyl, C$_{1-4}$ haloalkyl, C$_{3-8}$ cycloalkyl ring, —OR$^8$, —SR$^8$, —N(R$^8$)$_2$, or an oxo group; wherein each said cycloalkyl group is optionally and independently substituted with up to 3 instances of halogen;

each R$^{7b}$ is independently selected from halogen, —CN, —NO$_2$, C$_{1-4}$ alkyl, C$_{1-4}$ haloalkyl, C$_{3-8}$ cycloalkyl ring, —OR$^8$, —SR$^8$, —N(R$^8$)$_2$, or an oxo group; wherein each said cycloalkyl group is optionally and independently substituted with up to 3 instances of halogen;

each R$^8$ is independently selected from hydrogen, a C$_{1-4}$ alkyl, C$_{1-4}$ haloalkyl or a C$_{3-8}$ cycloalkyl ring; wherein each said cycloalkyl group is optionally and independently substituted with up to 3 instances of halogen;

alternatively, two instances of R$^8$ linked to the same nitrogen atom of R$^7$, R$^{7a}$ or R$^{7b}$, together with said nitrogen atom of R$^7$, R$^{7a}$ or R$^{7b}$, form a 5 to 8-membered heterocyclic ring or a 5-membered heteroaryl ring; wherein each said 5 to 8-membered heterocyclic ring and each said 5-membered heteroaryl ring optionally contains up to 2 additional heteroatoms independently selected from N, O or S; and R$^A$ is selected from hydrogen, halogen, C$_{1-4}$ alkyl or C$_{1-4}$ haloalkyl.

2. The compound of claim 1, or a pharmaceutically acceptable salt thereof, wherein ring B is phenyl or a 6-membered heteroaryl ring.

3. The compound of claim 2, or a pharmaceutically acceptable salt thereof, wherein n is an integer selected from 1 to 3, and wherein each $J^B$ is independently selected from halogen atoms.

4. The compound of claim 2, or a pharmaceutically acceptable salt thereof, wherein n is 1 and wherein each $J^B$ is independently selected from halogen, a C1.6 aliphatic or —ORB.

5. The compound of claim 2, or a pharmaceutically acceptable salt thereof, wherein n is an integer selected from 1 to 3, each $J^B$ is independently selected from halogen, a $C_{1-6}$ aliphatic or —$OR^B$, and at least one $J^B$ is ortho to the attachment of the methylene linker between ring B and the pyrazolyl ring.

6. The compound of claim 5, or a pharmaceutically acceptable salt thereof, wherein n is 1 and the $J^B$ ortho to the attachment of the methylene linker between ring B and the pyrazolyl ring is fluoro.

7. The compound of claim 1, or a pharmaceutically acceptable salt thereof, wherein ring B is a 6-membered heteroaryl ring.

8. The compound of claim 7, or a pharmaceutically acceptable salt thereof, wherein ring B is a pyridyl ring.

9. The compound of claim 7, or a pharmaceutically acceptable salt thereof, wherein ring B is a pyrimidinyl ring.

10. The compound of claim 1, or a pharmaceutically acceptable salt thereof, wherein o is an integer selected between 1 and 3, and each $J^D$ is independently selected from halogen, a $C_{1-6}$ aliphatic, —$N(R^D)_2$, —$N(R^d)C(O)R^D$, —$N(R^d)C(O)OR^D$, —$N(R^d)C(O)N(RD)_2$, —$SO_2RD$, —$SO_2N(RD)_2$, —$N(R^d)SO_2RD$, —SRS, —$OR^D$ or an optionally substituted $C_{3-8}$ cycloaliphatic ring.

11. The compound of claim 1, or a pharmaceutically acceptable salt thereof, wherein o is an integer selected between 1 and 3, and each JD is independently selected from methyl, chloro, fluoro, —$N(RD)_2$, $N(R^d)C(O)RD$, oxo or —$OR^D$.

12. The compound of claim 11, or a pharmaceutically acceptable salt thereof, wherein each $R^d$ is independently selected from hydrogen or $C_{1-4}$ alkyl.

13. The compound of claim 1, or a pharmaceutically acceptable salt thereof, wherein ring C is a phenyl, a monocyclic 5 or 6-membered heteroaryl ring, a monocyclic 3 to 6-membered cycloaliphatic ring or a monocyclic 4 to 6-membered heterocycle; each of them optionally and independently substituted with up to 3 instances of $J^C$.

14. The compound of claim 1, or a pharmaceutically acceptable salt thereof, wherein ring C is phenyl, optionally and independently substituted by up to 3 instances of $J^C$.

15. The compound of claim 1, or a pharmaceutically acceptable salt thereof, wherein ring C is a 5 to 6-membered heteroaryl ring, optionally substituted by up to 3 instances of $J^C$, and each $J^C$ is independently selected from fluoro, methyl, —CN or —$OCH_3$.

16. The compound of claim 15, or a pharmaceutically acceptable salt thereof, wherein ring C is a 5 to 6-membered heteroaryl ring and it is unsubstituted.

17. The compound of claim 15, or a pharmaceutically acceptable salt thereof, wherein ring C is an oxazolyl or isoxazolyl ring and it is unsubstituted.

18. The compound of claim 1, or a pharmaceutically acceptable salt thereof, wherein the compound has structural Formula IIA, IIB or IIC:

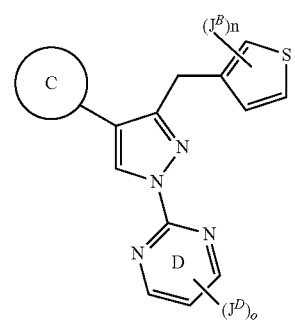

Formula IIA

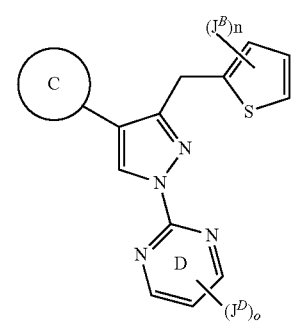

Formula IIB

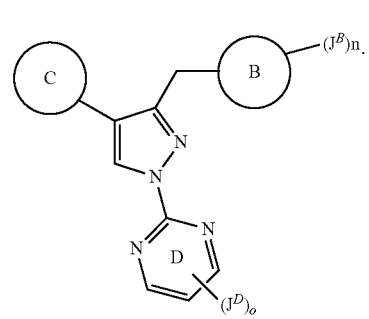

Formula IIC

19. The compound of claim 18, or a pharmaceutically acceptable salt thereof, wherein o is 2 and each $J^D$ is independently selected from a halogen atom or —$N(RD)_2$, —$N(R^d)COR^D$, —OH or oxo.

20. The compound of claim 18, or a pharmaceutically acceptable salt thereof, wherein $R^C$ is a 5 to 6-membered heteroaryl ring and is optionally and independently substituted by up to 3 instances of $J^C$.

21. The compound of claim 20, or a pharmaceutically acceptable salt thereof, wherein the 5 to 6-membered heteroaryl ring is selected from thienyl, thiazolyl, oxadiazolyl, oxazolyl, isoxazolyl, tetrazolyl, pyrrolyl, triazolyl, furanyl, pyridinyl, pyrimidinyl, pyrazinyl or pyridazinyl.

22. The compound of claim 21, or a pharmaceutically acceptable salt thereof, wherein the heteroaryl ring C is selected from isoxazolyl or oxazolyl.

23. The compound of claim 1 selected from those depicted in the table below or a pharmaceutically acceptable salt thereof I-1 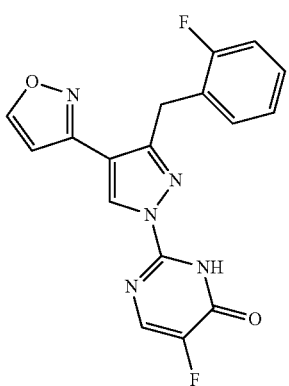
I-2 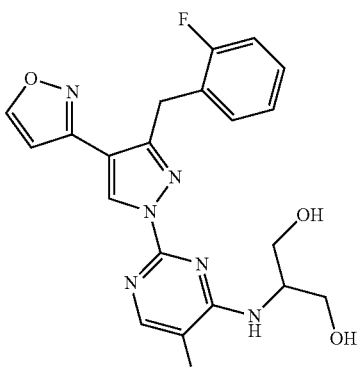
I-3 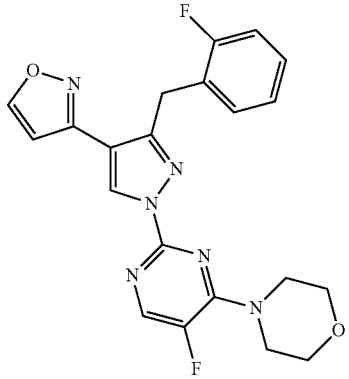
I-4 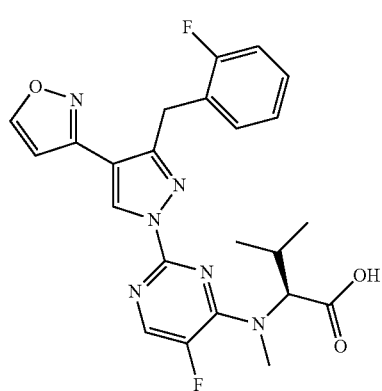
-continued
I-5 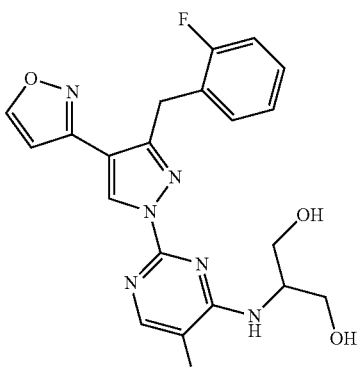
I-6 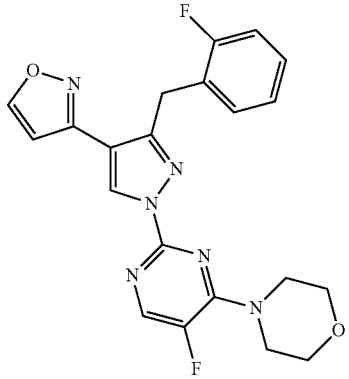
I-7 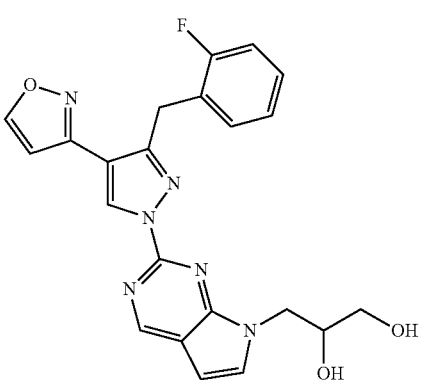
I-8 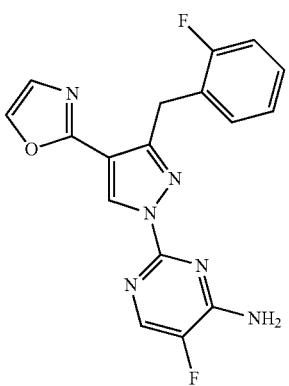

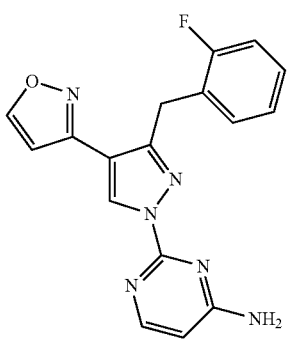
I-9
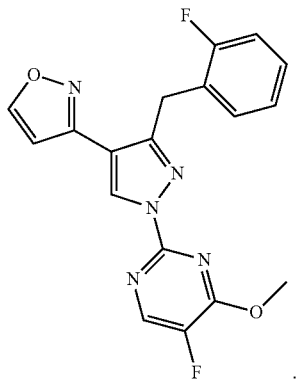
I-10
24. A pharmaceutical composition comprising the compound of claim 1, or a pharmaceutically acceptable salt thereof, and at least one pharmaceutically acceptable excipient.
* * * * *

UNITED STATES PATENT AND TRADEMARK OFFICE
CERTIFICATE OF CORRECTION

PATENT NO. : 9,487,508 B2  
APPLICATION NO. : 14/429028  
DATED : November 8, 2016  
INVENTOR(S) : Nakai et al.

Page 1 of 1

It is certified that error appears in the above-identified patent and that said Letters Patent is hereby corrected as shown below:

In the Claims

Column 127, Line 32: Claim 10, Delete ", $-N(R^d)C(O)N(RD)_2$, $-SO_2RD$, $-SO_2N(RD)_2$, $-N(R^d)SO_2RD$, $-SRS$," and insert -- $-N(R^d)C(O)N(R^D)_2$, $-SO_2R^D$, $-SO_2N(R^D)_2$, $-N(R^d)SO_2R^D$, $-SR^D$, --

Column 127, Line 38: Claim 11, "$-N(RD)_2$, $N(R^d)C(O)RD$," and insert -- $-N(R^D)_2$, $N(R^d)C(O)R^D$, --

Column 128, Line 50: Claim 19, Delete "$-N(RD)_2$," and insert -- $-N(R^D)_2$, --

Signed and Sealed this  
Seventh Day of February, 2017

Michelle K. Lee  
*Director of the United States Patent and Trademark Office*